(12) United States Patent
Cumming et al.

(10) Patent No.: US 8,278,334 B2
(45) Date of Patent: Oct. 2, 2012

(54) CYCLIC AMINE BACE-1 INHIBITORS HAVING A BENZAMIDE SUBSTITUENT

(75) Inventors: Jared N. Cumming, Garwood, NJ (US); Ulrich Iserloh, Hoboken, NJ (US); Andrew Stamford, Chatham Township, NJ (US); Corey Strickland, Martinsville, NJ (US); Johannes H. Voigt, Union, NJ (US); Yusheng Wu, New York, NY (US); Ying Huang, East Brunswick, NJ (US); Yan Xia, Edison, PA (US); Samuel Chackalamannil, Califon, NJ (US); Tao Guo, Dayton, NJ (US); Douglas W. Hobbs, Yardley, PA (US); Thuy X. H. Le, Monmouth Junction, NJ (US); Jeffrey F. Lowrie, Pennington, NJ (US); Kurt W. Saionz, Cranford, NJ (US); Suresh D. Babu, Plainsboro, NJ (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 12/641,952

(22) Filed: Dec. 18, 2009

(65) Prior Publication Data
US 2010/0152138 A1    Jun. 17, 2010

Related U.S. Application Data

(62) Division of application No. 10/910,987, filed on Aug. 4, 2004, now Pat. No. 7,662,816.

(60) Provisional application No. 60/493,987, filed on Aug. 8, 2003.

(51) Int. Cl.
| | |
|---|---|
| *A61K 31/4439* | (2006.01) |
| *A61K 31/40* | (2006.01) |
| *A61K 31/4025* | (2006.01) |
| *C07D 207/12* | (2006.01) |
| *C07D 401/06* | (2006.01) |
| *C07D 403/12* | (2006.01) |

(52) U.S. Cl. ..... 514/340; 514/422; 514/424; 546/276.4; 546/278.4; 548/518; 548/556

(58) Field of Classification Search ........................ None
See application file for complete search history.

(56) References Cited

U.S. PATENT DOCUMENTS

| | | | |
|---|---|---|---|
| 6,683,091 | B2 | 1/2004 | Asberom et al. |
| 7,585,885 | B2 * | 9/2009 | Shepherd et al. ............. 514/408 |
| 7,618,978 | B2 * | 11/2009 | Bueno Melendo et al. ... 514/278 |
| 2010/0222581 | A1 * | 9/2010 | Thompson et al. ........... 544/169 |

FOREIGN PATENT DOCUMENTS

| | | |
|---|---|---|
| WO | 9518104 | 6/1995 |
| WO | 0007995 | 2/2000 |
| WO | 00/50391 | 8/2000 |
| WO | 0202505 | 1/2002 |
| WO | 0202506 | 1/2002 |
| WO | 0202512 | 1/2002 |
| WO | 0202518 | 1/2002 |
| WO | 0202520 | 1/2002 |
| WO | 02088101 | 11/2002 |
| WO | 03013527 | 2/2003 |
| WO | 03018543 | 3/2003 |
| WO | 03066592 | 8/2003 |

OTHER PUBLICATIONS

Vippagunta et al. Advanced Drug Delivery Reviews, vol. 48, p. 3-26 (2001).*
Hom, Expert Opin.Ther. Patents, vol. 17,p. 737-740 (2007).*
Philip L. Gould, Salt Selection for Basic Drugs, International Journal of Pharmaceutics, 33(1986) 201-217.
George R. Pettit, et al., The Dolastatins; 18: Stereospecific Synthesis of Dolaproine, Synthesis, (1996) 719-725.
Ugo Pfeiffer, et al., A Short Synthesis of 4-Imidazolidinone, Liebigs Ann. Chem., (1988) 993-995.
Bruno Bellier, et al., Synthesis and Biological Properties of New Constrained CCK-B Antagonists: Discrimination of Two Affinity States of the CCK-B Receptor on Transfected CHO Cells, J. Med. Chem., (1997) 40:3947-3956.
Thomas R. Webb, et al., Conformationally Restricted Arginine Analogues, J. Org. Chem., (1991) 56:3009-3016.
Stephen Hanessian, et al., The Power of Visual Imagery in Synthesis Planning. Stereocontrolled Approaches to CGP-60536B, a Potent Renin Inhibitor, J. Org. Chem., (2002) 67:4261-4274.
Samuel Chackalamannil, et al., Total Synthesis of (+)-Himbacine and (+)-Himbeline, J. Org. Chem. (1999) 64:1932-1940.
Christoph Hock, et al., Generation of Antibodies Specific for β-amyloid by Vaccination of Patients with Alzheimer Disease, Nature Medicine, (2002) 8:1270-1275.
Toshimasa Itoh et al., Asymmetric Synthesis of (−)-Adaline, Organic Letters, (2002) 4:2469-2472.
Christopher J. Dinsmore, et al., 3,8-Diazabicyclo[3.2.1]octan-2-one Peptide Mimetics: Synthesis of a Conformationally Restricted Inhibitor of Farnesyltransferase, Organic Letters, (2001) 3:865-868.
Lawrence I. Kruse, et al., Multisubstrate Inhibitors of Dopamine β-Hydroxylase. 2.1 Structure-Activity Relationships at the Phenethylamine Binding Site, J. Med. Chem., (1987) 30:486-494.
Zhenping Tian et al., An Efficient Scalable Process for the Synthesis of N-Boc-2-tert-butyldimethylsiloxypyrrole, Organic Process Research & Development, (2002) 6:416-418.
Gordon Lowe et al., Amino Acid Bearing Nucleobases for the Synthesis of Novel Peptide Nucleic Acids, J. Chem. Soc., Perkin Trans.1, (1997) 539-546.
Stephen M. Berge, et al., Pharmaceutical Salts, Journal of Pharmaceutical Sciences (1977) 66:1-19.
McGaughey, et. al., Expert Opin. Drug Discov. vol. 2 (8), pp. 1129-1138 (2007).
Melnikova, Nature Reviews Drug Discovery, vol. 6, p. 341-342 (2007).
International Search Report for International Application No. PCT/US2004/025018 mailed Aug. 22, 2005 (5 pages).

* cited by examiner

*Primary Examiner* — Emily Bernhardt
(74) *Attorney, Agent, or Firm* — Keith D. MacMillan; Gerard M. Devlin

(57) ABSTRACT

Disclosed are compounds of the formula

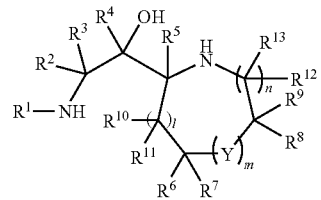

or a pharmaceutically acceptable salt or solvate thereof, wherein
R¹ is

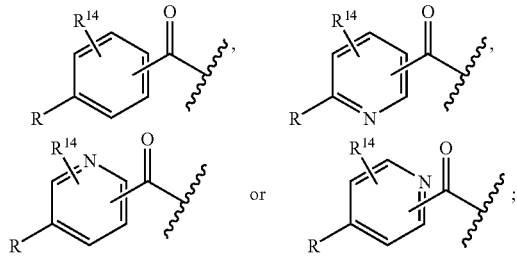

R is —C(O)—N(R²⁷)(R²⁸) or

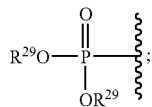

and the remaining variables are as defined in the specification. Also disclosed are pharmaceutical compositions comprising the compounds of formula I.

Also disclosed are methods of treating cognitive or neurodegenerative diseases such as Alzheimer's disease.

Also disclosed are pharmaceutical compositions and methods of treating cognitive or neurodegenerative diseases comprising the compounds of formula I in combination with a β-secretase inhibitor other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody.

10 Claims, No Drawings

CYCLIC AMINE BACE-1 INHIBITORS HAVING A BENZAMIDE SUBSTITUENT

CROSS-REFERENCE TO RELATED APPLICATIONS

The present application is a divisional of co-pending application U.S. Ser. No. 10/910,987, filed Aug. 4, 2004, which claims the benefit of priority to U.S. Provisional Application No. 60/493,987, filed Aug. 8, 2003, each of which is incorporated herein by reference.

FIELD OF THE INVENTION

This invention relates to substituted cyclic amine BACE-1 inhibitors having a benzamide or pyridine carboxamide substituent, pharmaceutical compositions comprising said compounds, and their use in the treatment of Alzheimer's disease.

BACKGROUND

Alzheimer's disease (AD) is a progressive neurodegenerative disease that is ultimately fatal. Disease progression is associated with gradual loss of cognitive function related to memory, reasoning, orientation and judgment. Behavioral changes including confusion, depression and aggression also manifest as the disease progresses. The cognitive and behavioral dysfunction is believed to result from altered neuronal function and neuronal loss in the hippocampus and cerebral cortex. The currently available AD treatments are palliative, and while they ameliorate the cognitive and behavioral disorders, they do not prevent disease progression. Therefore there is an unmet medical need for AD treatments that halt disease progression.

Pathological hallmarks of AD are the deposition of extracellular β-amyloid (Aβ) plaques and intracellular neurofibrillary tangles comprised of abnormally phosphorylated protein tau. Individuals with AD exhibit characteristic Aβ deposits, in brain regions known to be important for memory and cognition. It is believed that Aβ is the fundamental causative agent of neuronal cell loss and dysfunction which is associated with cognitive and behavioral decline. Amyloid plaques consist predominantly of Aβ peptides comprised of 40-42 amino acid residues, which are derived from processing of amyloid precursor protein (APP). APP is processed by multiple distinct protease activities. Aβ peptides result from the cleavage of APP by β-secretase at the position corresponding to the N-terminus of Aβ, and at the C-terminus by γ-secretase activity. APP is also cleaved by α-secretase activity resulting in the secreted, non-amyloidogenic fragment known as soluble APP.

An aspartyl protease known as BACE-1 has been identified as the β-secretase responsible for cleavage of APP at the position corresponding to the N-terminus of Aβ peptides.

Accumulated biochemical and genetic evidence supports a central role of Aβ in the etiology of AD. For example, Aβ has been shown to be toxic to neuronal cells in vitro and when injected into rodent brains. Furthermore inherited forms of early-onset AD are known in which well-defined mutations of APP or the presenilins are present. These mutations enhance the production of Aβ and are considered causative of AD.

Since Aβ peptides are formed as a result β-secretase activity, inhibition of the BACE-1 enzyme should inhibit formation of Aβ peptides. Thus inhibition of BACE-1 is a therapeutic approach to the treatment of AD and other cognitive and neurodegenerative diseases caused by Aβ plaque deposition.

Substituted amine BACE-1 inhibitors are disclosed in WO 02/02505, WO 02/02506, WO 02/02512, WP 02/02518 and WO 02/02520. Renin inhibitors comprising a (1-amino-2 hydroxy-2-heterocyclic)ethyl moiety are disclosed in WO 89/03842. WO 02/088101 discloses BACE inhibitors functionally described as being comprised of four hydrophobic moieties, as well as series of compounds preferably comprising a heterocyclic or heteroaryl moiety.

SUMMARY OF THE INVENTION

The present invention relates to compounds having the structural formula I

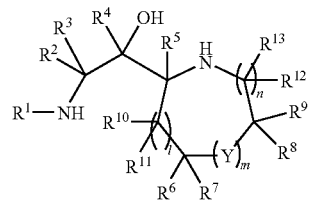

or a pharmaceutically acceptable salt or solvate thereof, wherein
R$^1$ is

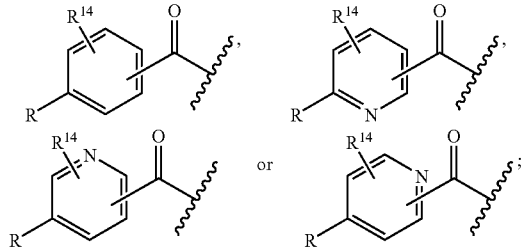

R is —C(O)—N(R$^{27}$)(R$^{28}$) or

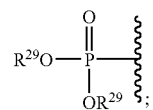

R$^2$ is H, alkyl, cycloalkyl, heterocycloalkyl, cycloalkylalkyl, heterocycloalkylalkyl, aryl, heteroaryl, arylalkyl, heteroarylalkyl, alkenyl or alkynyl;

R$^3$ is H or alkyl;

R$^4$ is H or alkyl;

R$^5$ is H, alkyl, cycloalkyl, cycloalkylalkyl, aryl, arylalkyl, heteroaryl, heteroarylalkyl, heterocycloalkyl or heterocycloalkylalkyl;

R$^{14}$ is 1 to 4 substituents independently selected from the group consisting of H, alkyl, alkenyl, alkynyl, halo, —CN, haloalkyl, cycloalkyl, cycloalkylalkyl, aryl, heteroaryl, heterocycloalkyl, arylalkyl, heteroarylalkyl, heterocycloalkylalkyl, —OR$^{35}$, —N(R$^{24}$)(R$^{25}$) and —SR$^{35}$;

R$^{27}$ and R$^{28}$ are independently selected from alkyl, cycloalkyl, cycloalkylalkyl, aryl, arylalkyl, heteroaryl, heteroarylalkyl, heterocycloalkyl, heterocycloalkylalkyl, hydroxyalkyl, and alkoxyalkyl;

or $R^{27}$ and $R^{28}$ together with the nitrogen to which they are attached, form an unsubstituted 3-7 membered heterocycloalkyl ring, or a 3-7 membered heterocycloalkyl ring substituted by 1-3 substituents independently selected from the group consisting of alkyl, alkoxyalkyl, haloalkoxyalkyl, cycloalkyl, cycloalkylalkyl and cycloalkyl-alkoxyalkyl;

each $R^{29}$ is independently selected from H, alkyl, cycloalkyl, cycloalkylalkyl, aryl, arylalkyl, heteroaryl, heteroarylalkyl, heterocycloalkyl, heterocycloalkylalkyl, hydroxyalkyl, and alkoxyalkyl;

and wherein l, n, m, Y, and $R^6$, $R^7$, $R^8$, $R^9$, $R^{10}$, $R^{11}$, $R^{12}$ and $R^{13}$ are as defined in the following groups (A) to (C):

(A) when l is 0-3; n is 0-3; m is 0 or m is 1 and Y is —C($R^{30}$)($R^{31}$)—; and the sum of l and n is 0-3:
  (i) $R^6$, $R^7$, $R^8$, $R^9$, $R^{10}$ and $R^{11}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl, alkynyl, halo, —$NO_2$, —CN, —N($R^{15}$)($R^{16}$), —$OR^{17}$, —$SR^{17}$, —C(O)$R^{18}$, —N($R^{15}$)—C(O)$R^{17}$, —C(O)$OR^{17}$, —C(O)N($R^{15}$)($R^{16}$), —O—C(O)$R^{17}$ and —S(O)$_{1-2}R^{18}$; and
  $R^{12}$ and $R^{13}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl, alkynyl, —C(O)$R^{18}$ and —C(O)$OR^{17}$;
or (ii) $R^7$ and $R^9$, together with the ring carbons to which they are attached, form a fused cycloalkyl or fused heterocycloalkyl group and $R^6$, $R^8$, $R^{10}$, $R^{11}$, $R^{12}$ and $R^{13}$ are as defined in (A)(i); or $R^{10}$ and $R^{11}$, together with the ring carbon to which they are attached, form —C(O)—; or $R^{12}$ and $R^{13}$, together with the ring carbon to which they are attached, form —C(O)—;
or (iii) $R^6$ and $R^7$, together with the ring carbon to which they are attached, form —C(=O)—, and $R^8$, $R^9$, $R^{10}$, $R^{11}$, $R^{12}$ and $R^{13}$ are as defined in (A)(i);
or (iv) $R^8$ and $R^9$, together with the ring carbon to which they are attached, form —C(=O)—, and $R^6$, $R^7$, $R^{10}$, $R^{11}$, $R^{12}$ and $R^{13}$ are as defined in (A)(i);

(B) when l is 1; n is 0-2; and m is 0:
  $R^6$ and $R^8$, together with the ring carbons to which they are attached, form a fused aryl group or a fused heteroaryl group, $R^7$ and $R^9$ form a bond, and $R^{10}$, $R^{11}$, $R^{12}$ and $R^{13}$ are as defined in (A)(i);

(C) when l is 0-3; n is 0-3; m is 1 and Y is —O—, —$NR^{19}$—, —S—, —SO— or $SO_2$—; and the sum of l and n is 0-3:
  $R^6$, $R^7$, $R^8$, $R^9$, $R^{12}$ and $R^{13}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl, alkynyl, —C(O)N($R^{15}$)($R^{16}$), —C(O)$R^{18}$, —C(O)$OR^{17}$ and —O—C(O)$R^{17}$; and $R^{10}$ and $R^{11}$ are as defined in (A)(i), or $R^{19}$ and $R^{11}$, together with the ring carbon to which they are attached, form —C(O)—; or $R^{12}$ and $R^{13}$, together with the ring carbon to which they are attached, form —C(O)—; or when Y is —O— or —$NR^{19}$—, $R^6$ and $R^7$, together with the ring carbon to which they are attached, form —C(O)—; or when Y is —O— or —$NR^{19}$—, $R^8$ and $R^9$, together with the ring carbon to which they are attached, form —C(O)—;

wherein $R^{15}$ is H or alkyl;

$R^{16}$ is H, alkyl, cycloalkyl, cycloalkylalkyl, aryl, heteroaryl, heterocycloalkyl, arylalkyl, heteroarylalkyl, heterocycloalkylalkyl, alkenyl or alkynyl;

or $R^{15}$ and $R^{16}$, together with the nitrogen to which they are attached, form a heterocycloalkyl ring;

$R^{17}$ is H, alkyl, cycloalkyl, aryl, heteroaryl, cycloalkylalkyl, arylalkyl, heteroarylalkyl, heterocycloalkyl, heterocycloalkylalkyl, alkenyl or alkynyl;

$R^{18}$ is H, alkyl, cycloalkyl, aryl, heteroaryl, cycloalkylalkyl, arylalkyl, heteroarylalkyl, heterocycloalkyl, heterocycloalkylalkyl, alkenyl, alkynyl or —N($R^{24}$)($R^{25}$);

$R^{19}$ is H, alkyl, cycloalkyl, cycloalkylalkyl, aryl, heteroaryl, heterocycloalkyl, arylalkyl, heteroarylalkyl, heterocycloalkylalkyl, —$COR^{18}$, —C(O)$OR^{49}$, —$SOR^{18}$, —$SO_2R^{18}$ or —CN;

$R^{24}$ and $R^{25}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl and alkynyl;

or $R^{24}$ and $R^{25}$ together with the nitrogen to which they are attached, form a 3-7 membered heterocycloalkyl ring;

$R^{30}$ is H, alkyl, cycloalkyl, cycloalkylalkyl, aryl, heteroaryl, heterocycloalkyl, arylalkyl, heteroarylalkyl, heterocycloalkylalkyl, alkenyl, alkynyl, halo, —$NO_2$, —CN, —N($R^{15}$)($R^{16}$), —$OR^{17}$, —$SR^{17}$, —C(O)$R^{18}$, —N($R^{15}$)—C(O)$R^{17}$, —C(O)$OR^{17}$, —C(O)N($R^{15}$)($R^{16}$), —O—C(O)$R^{17}$ or —S(O)$_{1-2}R^{18}$;

$R^{31}$ is H or alkyl;

and wherein each of the alkyl, cycloalkyl, cycloalkylalkyl, heterocycloalkyl, heterocycloalkylalkyl, aryl, arylalkyl, heteroaryl, heteroarylalkyl, alkenyl and alkynyl groups in $R^2$, $R^3$, $R^4$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{24}$, $R^{25}$ and $R^{30}$ are independently unsubstituted or substituted by 1 to 5 $R^{32}$ groups independently selected from the group consisting of halo, alkyl, cycloalkyl, cycloalkylalkyl, heterocycloalkyl, heterocycloalkylalkyl, aryl, arylalkyl, heteroaryl, heteroarylalkyl, —$NO_2$, —CN, haloalkyl, haloalkoxy, —N($R^{33}$)($R^{34}$), —NH(cycloalkyl), acyloxy, —$OR^{35}$, —$SR^{35}$, —C(O)$R^{36}$, —C(O)$OR^{35}$, —PO($OR^{35}$)$_2$, —$NR^{35}$C(O)$R^{36}$, —$NR^{35}$C(O)$OR^{39}$, —$NR^{35}$S(O)$_{0-2}R^{39}$, and —S(O)$_{0-2}R^{39}$; or two $R^{32}$ groups on the same ring carbon atom in cycloalkyl, cycloalkylalkyl, heterocycloalkyl or heterocycloalkylalkyl together form =O;

$R^{33}$ and $R^{34}$ are independently selected from the group consisting of H and alkyl;

$R^{35}$ is H, alkyl, cycloalkyl, aryl, heteroaryl, cycloalkylalkyl, arylalkyl, heteroarylalkyl, heterocycloalkyl, heterocycloalkylalkyl, alkenyl or alkynyl;

$R^{36}$ is H, alkyl, cycloalkyl, aryl, heteroaryl, cycloalkylalkyl, arylalkyl, heteroarylalkyl, heterocycloalkyl, heterocycloalkylalkyl, alkenyl, alkynyl or —N($R^{37}$)($R^{38}$);

$R^{37}$ and $R^{38}$ are independently selected from the group consisting of H, alkyl, cycloalkyl, cycloalkylalkyl, aryl, heteroaryl, heterocycloalkyl, arylalkyl, heteroarylalkyl, heterocycloalkylalkyl, alkenyl and alkynyl;

or $R^{37}$ and $R^{38}$ together with nitrogen to which they are attached, form a 3-7 membered heterocycloalkyl ring;

$R^{39}$ is alkyl, aryl, heteroaryl, arylalkyl, heteroarylalkyl, heterocycloalkyl, heterocycloalkylalkyl, alkenyl or alkynyl; and $R^{40}$ is alkyl, cycloalkyl, aryl, heteroaryl, cycloalkylalkyl, arylalkyl, heteroarylalkyl, heterocycloalkyl, heterocycloalkylalkyl, alkenyl or alkynyl.

In another aspect, the invention relates to a pharmaceutical composition comprising at least one compound of formula I and a pharmaceutically acceptable carrier.

In another aspect, the invention comprises the method of inhibiting BACE-1 comprising administering at least one compound of formula I to a patient in need of such treatment. Also claimed is the method of inhibiting the formation, or formation and deposition, of β-amyloid plaques in, on or around neurological tissue (e.g., the brain) comprising administering at least one compound of formula I to a patient in need of such treatment.

More specifically, the invention comprises the method of treating a cognitive or neurodegenerative disease comprising administering at least one compound of formula I to a patient in need of such treatment. In particular, the invention comprises the method of treating Alzheimer's disease comprising administering at least one compound of formula I to a patient in need of such treatment.

In another aspect, the invention comprises the method of treating a cognitive or neurodegenerative disease comprising administering to a patient I need of such treatment a combination of at least one compound of formula I and at least one compound selected from the group consisting of β-secretase inhibitors other than those of formula I, HMG-CoA reductase inhibitors, gamma-secretase inhibitors, non-steroidal anti-inflammatory agents, N-methyl-D-aspartate receptor antagonists, cholinesterase inhibitors and anti-amyloid antibodies.

In a final aspect, the invention relates to a kit comprising in separate containers in a single package pharmaceutical compositions for use in combination, in which one container comprises a compound of formula I in a pharmaceutically acceptable carrier and a second container comprises a β-secretase inhibitors other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody in a pharmaceutically acceptable carrier, the combined quantities being an effective amount to treat a cognitive disease or neurodegenerative disease such as Alzheimer's disease.

DETAILED DESCRIPTION

Referring to formula I, above, preferred compounds of the invention are those wherein $R^3$, $R^4$ and $R^5$ are hydrogen and $R^2$ is arylalkyl; more preferred are compounds wherein $R^2$ is substituted benzyl, especially di-fluorobenzyl.

In compounds of formula I, R is preferably —C(O)—N($R^{27}$)($R^{28}$) wherein $R^{27}$ and $R^{28}$ are each alkyl, more preferably n-propyl. Also preferred are compounds wherein $R^{27}$ and $R^{28}$, together with the nitrogen to which they are attached, form an optionally substituted heterocycloalkyl, ring, preferably piperidinyl or pyrrolidinyl, especially pyrrolidinyl, and preferably substituted by alkoxyalkyl, especially methoxymethyl. In another preferred embodiment, R is

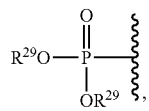

wherein each $R^{29}$ is alkyl, more preferably n-propyl. R is more preferably —C(O)—N($R^{27}$)($R^{28}$). $R^{14}$ is preferably H, alkyl or alkoxy, especially methyl.

The "$R^1$—NH—" portion of the compounds of formula I preferably has the structure:

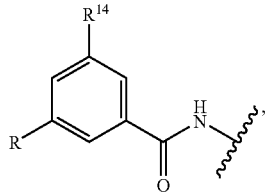

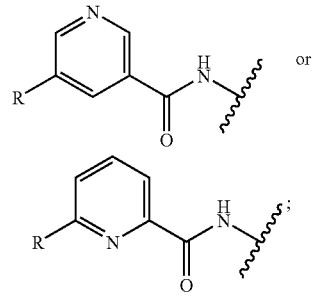

benzamides are more preferred.

Preferred $R^{32}$ substituents are selected from the group consisting of halo, alkyl, OH, alkoxy, alkoxyalkyl, alkoxyalkoxy, haloalkyl, haloalkoxy, CN, cycloalkyl, cycloalkoxy, cycloalkylalkyl, cycloalkylalkoxy, phenyl and benzyl. Also preferred are compounds wherein two $R^{32}$ substituents on the same ring carbon in a cycloalkyl, cycloalkylalkyl, heterocycloalkyl or heterocycloalkylalkyl group form =O.

The following are additional preferred embodiments of the invention:
1) compounds of formula I wherein $R^1$ to $R^5$ are as defined above in the summary of the invention and $R^6$ to $R^{13}$, 1, m, n, and Y are as defined in (A);
2) compounds of formula I wherein $R^1$ to $R^5$ are the preferred definitions defined above and $R^6$ to $R^{13}$, 1, m, n, and Y are as defined in (A);
3) compounds of formula I wherein $R^1$ to $R^5$ are as defined above in the summary of the invention and $R^6$ to $R^{13}$, 1, m, n, and Y are as defined in (B);
4) compounds of formula I wherein $R^1$ to $R^5$ are the preferred definitions defined above and $R^6$ to $R^{13}$, 1, m, n, and Y are as defined in (B);
5) compounds of formula I wherein $R^1$ to $R^5$ are as defined above in the summary of the invention and $R^6$ to $R^{13}$, 1, m, n, and Y are as defined in (C);
6) compounds of formula I wherein $R^1$ to $R^5$ are the preferred definitions defined above and $R^6$ to $R^{13}$, 1, m, n, and Y are as defined in (C).

In another embodiment, preferred are compounds of formula I, definition (A), wherein m is zero; the sum of 1 and n is 1 or 2; and $R^6$, $R^7$, $R^8$, $R^9$, $R^{10}$, $R^{11}$, $R^{12}$ and $R^{13}$ are each hydrogen; or wherein $R^6$, $R^7$, $R^8$, $R^9$, $R^{10}$, $R^{11}$, and $R^{13}$ are each hydrogen and $R^{12}$ is methyl; or wherein $R^6$, $R^7$, $R^8$, $R^9$, $R^{10}$ and $R^{11}$ are each hydrogen and $R^{12}$ and $R^{13}$ together are =O; or wherein $R^6$, $R^7$, $R^8$, $R^9$, $R^{12}$ and $R^{13}$ are each hydrogen and $R^{10}$ and $R^{11}$ are =O.

In another embodiment, preferred are compounds of formula I, definition (A), wherein m is zero; n is 1 and the sum of n and l is 1 or 2; $R^6$, $R^9$, $R^{10}$, $R^{11}$, $R^{12}$ and $R^{13}$ are each hydrogen; and $R^7$ and $R^8$ are as defined in the summary of the invention. More preferred are compounds of formula I, definition (A), wherein m is zero; n is 1 and the sum of n and l is 1 or 2; $R^6$, $R^9$, $R^{10}$, $R^{11}$, $R^{12}$ and $R^{13}$ are each hydrogen; and $R^7$ and $R^8$ are independently selected from the group consisting of H and —$OR^{17}$ wherein $R^{17}$ is H, alkyl, aryl, heteroaryl, arylalkyl or heteroarylalkyl; A preferred definition for $R^{17}$ is arylalkyl, especially benzyl, wherein the aryl portion is optionally substituted with one or two substituents independently selected from the group consisting of halo and alkoxy.

In another embodiment, preferred are compounds of formula I, definition (A), wherein m is zero; l is 1; n is 1 or 2; $R^7$ and $R^9$ form a fused cycloalkyl group; and $R^6$, $R^8$, $R^{10}$, $R^{11}$, $R^{12}$ and $R^{13}$ are each hydrogen. Preferably, $R^7$, $R^9$ and the carbons to which they are attached form a cyclopropyl ring.

In another embodiment, preferred are compounds of formula I, definition (A), wherein m is 1; Y is —C($R^{30}$)($R^{31}$)—; l is 0; n is 1; $R^6$, $R^7$, $R^8$, $R^9$, $R^{12}$ and $R^{13}$ are each hydrogen; and $R^{30}$ and $R^{31}$ are as defined in the summary of the invention.

In another embodiment, preferred are compounds of formula I, definition (B), wherein m is zero; l is 1 and n is 1 or 2; $R^6$ and $R^8$ form a fused aryl group; $R^7$ and $R^9$ form a bond; and $R^{10}$, $R^{11}$, $R^{12}$ and $R^{13}$ are each hydrogen.

In another embodiment, preferred are compounds of formula I, definition (C), wherein m is 1; l is 0-3 and n is 0-3, provided that the sum of l and n is 1-3; Y is —O—, —$NR^{19}$—, —S—, —SO— or $SO_2$—, wherein $R^{19}$ is alkyl, arylalkyl or $SO_2R^{18}$, with preferred arylalkyl groups being benzyl and fluorobenzyl and preferred $R^{18}$ groups being aryl and heteroaryl, especially phenyl, pyridyl, thienyl and imidazolyl; and $R^6$, $R^7$, $R^8$, $R^9$, $R^{10}$, $R^{11}$, $R^{12}$ and $R^{13}$ are each hydrogen, or $R^8$, $R^9$, $R^{10}$, $R^{11}$, $R^{12}$ and $R^{13}$ are each hydrogen and $R^6$ and $R^7$ together are =O, or $R^8$, $R^9$, $R^{10}$, $R^{11}$, $R^{12}$ and $R^{13}$ are each hydrogen and $R^8$ and $R^{12}$ are as defined in the summary of the invention. More preferably, Y is —$NR^{19}$— or —O—, with —$NR^{19}$— being most preferred. In an especially preferred embodiment, m is 1; Y is —$NR^{19}$—; l is 0; n is 1; $R^8$, $R^9$, $R^{12}$, and $R^{13}$ are H; and $R^6$ and $R^7$ together are =O. In another especially preferred embodiment, m is 1; Y is —$NR^{19}$—; l is 0; n is 0; $R^8$ and $R^9$ are H; and $R^6$ and $R^7$ together are =O.

Specific preferred embodiments of the cycloamino ring portion are:

(all A(i))

(A(ii))

(A(iv))

(B)

and (all C)

wherein:
$R^8$ is H, OH, alkoxy, phenoxy or optionally substituted benzyloxy;
$R^{12}$ is H, alkyl, alkenyl or di-hydroxyalkyl;
$R^{19}$ is H, alkyl, optionally substituted benzyl, benzoyl, —$SO_2$alkyl, —$SO_2$ (optionally substituted phenyl), —$SO_2$N(alkyl)$_2$, phenyl, —C(O)alkyl, —C(O)-heteroaryl, —C(O)—NH (optionally substituted phenyl), —C(O)—O-benzyl, —C(O)—$CH_2$—O-alkyl, —$SO_2$— (optionally substituted heteroaryl), —C(O)-morpholinyl or cycloalkylalkyl;
$R^{19a}$ is optionally substituted benzyl; and
$R^{30}$ is —OC(O)-alkyl, optionally substituted phenyl, optionally substituted phenylalkyl, alkyl, alkoxy, cycloalkylalkyl, cycloalkylalkoxy, hydroxyalkoxy, dialkylaminoalkoxy, alkoxyalkoxy, optionally substituted heterocycloalkyl, heterocycloalkylalkyl, heterocycloalkylalkoxy, or —C(O)—O-alkyl;
wherein the optional substituents on phenyl or benzyl are $R^{32}$ substituents selected from the group consisting of halo, alkyl, alkoxy, cyano and phenyl; wherein heteroaryl is selected from the group consisting of pyridyl, oxazolyl, pyrazinyl, thienyl and imidazolyl and the optional substituents on heteroaryl are selected from alkyl and halo.

More preferred specific embodiments of the cyclic amino portion are and wherein the substituents are as defined in the paragraph immediately above.

The preferred stereochemistry of compounds of formula I is that shown in formula IA:

IA

As used above, and throughout the specification, the following terms, unless otherwise indicated, shall be understood to have the following meanings:

"Patient" includes both human and animals.

"Mammal" means humans and other mammalian animals.

"Alkyl," means an aliphatic hydrocarbon group which may be straight or branched and comprising 1 to 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having 1 to 6 carbon atoms in the chain which may be straight or branched. Non-limiting examples of suitable alkyl groups include methyl, ethyl, n-propyl, isopropyl, n-butyl, t-butyl, n-pentyl, heptyl, nonyl and decyl. $R^{32}$-substituted alkyl groups include fluoromethyl, trifluoromethyl and cyclopropylmethyl.

"Alkenyl" means an aliphatic hydrocarbon group containing at least one carbon-carbon double bond and which may be straight or branched and comprising 2 to 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means 2 to 6 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising 2 to 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means 2 to 6 carbon atoms in the chain which may be straight or branched. Non-limiting examples of suitable alkynyl groups include ethynyl, propynyl, 2-butynyl, 3-methylbutynyl, n-pentynyl, and decynyl.

"Aryl" (sometimes abbreviated "ar") means an aromatic monocyclic or multicyclic ring system comprising 6 to 14 carbon atoms, preferably 6 to 10 carbon atoms. The aryl group can be optionally substituted with one or more $R^{32}$ substituents which may be the same or different, and are as defined herein. Non-limiting examples of suitable aryl groups include phenyl and naphthyl.

"Heteroaryl" means an aromatic monocyclic or multicyclic ring system comprising 5 to 14 ring atoms, preferably 5 to 10 ring atoms, in which one to four of the ring atoms is an element other than carbon, for example nitrogen, oxygen or sulfur, alone or in combination. Preferred heteroaryls contain 5 to 6 ring atoms. The "heteroaryl" can be optionally substituted by one or more $R^{32}$ substituents which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like.

"Arylalkyl" means an aryl-alkyl- group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Cycloalkyl" means a non-aromatic mono- or multicyclic ring system comprising 3 to 10 carbon atoms, preferably about 5 to about 10 carbon atoms. Preferred cycloalkyl rings contain about 5 to about 7 ring atoms. The cycloalkyl can be optionally substituted with one or more $R^{32}$ substituents which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalin, norbornyl, adamantyl and the like.

"Halo" means fluoro, chloro, bromo, or iodo groups. Preferred are fluoro, chloro or bromo, and more preferred are fluoro and chloro.

"Haloalkyl" means an alkyl as defined above wherein one or more hydrogen atoms on the alkyl is replaced by a halo group defined above.

Substituents on the rings defined above also include a cyclic ring of 3 to 7 ring atoms of which 1-2 may be a heteroatom, attached to an aryl, heteroaryl or heterocyclyl ring by simultaneously substituting two ring hydrogen atoms on said aryl, heteroaryl or heterocyclyl ring. Non-limiting examples include:

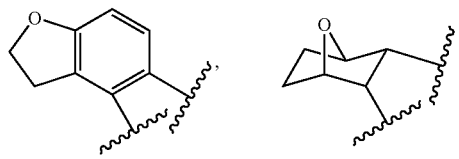

and the like.

"Heterocyclyl" (or heterocycloalkyl) means a non-aromatic saturated monocyclic or multicyclic ring system comprising 3 to 10 ring atoms, preferably about 5 to about 10 ring atoms, in which 1-3, preferably 1 or 2 of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. The heterocyclyl can be optionally substituted by one or more $R^{32}$ substituents which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

"Heteroarylalkyl" means a heteroaryl-alkyl- group in which the heteroaryl and alkyl are as previously described. Preferred heteroarylalkyls contain a lower alkyl group. Non-limiting examples of suitable heteroarylalkyl groups include pyridylmethyl, 2-(furan-3-yl)ethyl and quinolin-3-ylmethyl. The bond to the parent moiety is through the alkyl.

"Acyl" means an H—C(O)—, alkyl-C(O)—, alkenyl-C(O)—, alkynyl-C(O)— or cycloalkyl-C(O)— group in which the various groups are as previously described. The bond to the parent moiety is through the carbonyl. Preferred acyls contain a lower alkyl. Non-limiting examples of suitable acyl groups include formyl, acetyl, propanoyl, 2-methylpropanoyl, butanoyl and cyclohexanoyl.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

In the summary of the invention, in parts A(ii), B and C, where alternative definitions are given, the definitions are cumulative. For example in A(ii), where "$R^7$ and $R^9$, ... form a fused cycloalkyl or fused heterocycloalkyl group and $R^6$, $R^8$, $R^{10}$, $R^{11}$, $R^{12}$ and $R^{13}$ are as defined in (A)(i); or $R^{10}$ and $R^{11}$, ... form —C(O)—; or $R^{12}$ and $R^{13}$, ... form —C(O)—" it means that $R^7$ and $R^9$ form a ring, while the remaining "R" groups can be individual substituents, or $R^6$, $R^8$, $R^{12}$ and $R^{13}$ are individual substituents and $R^{10}$ and $R^{11}$ form =O, or $R^6$, $R^8$, $R^{10}$ and $R^{11}$ are individual substituents and $R^{12}$ and $R^{13}$ form =O, or $R^6$ and $R^8$ are individual substituents, $R^{19}$ and $R^{11}$ form =O and $R^{12}$ and $R^{13}$ form =O.

"Fused cycloalkyl" means that a cycloalkyl ring is fused to the cyclic amino portion of compounds of formula I, e.g., a compound having the structure

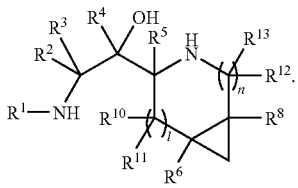

Similarly, "fused heterocycloalkyl" means that a heterocycloalkyl group is fused to the cyclic amino portion of compounds of formula I, e.g., a compound having the structure

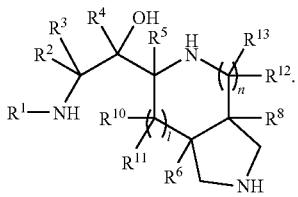

When "Y" is a heteroatom, $R^7$, $R^9$ and the carbons to which they are attached can form a fused ring wherein "Y" is the only heteroatom, or $R^7$, $R^9$ and the carbons to which they are attached can form a ring comprising one or two additional heteroatoms, e.g.,

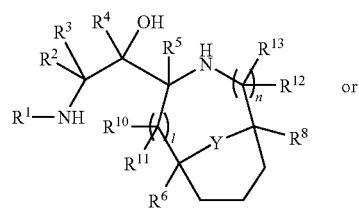

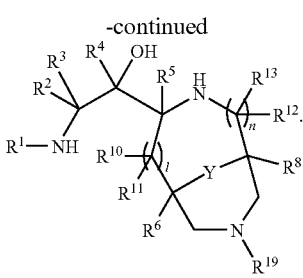

"Fused aryl" means that an aryl group is fused to the cyclic amino portion of compounds of formula I, e.g., a compound having the structure

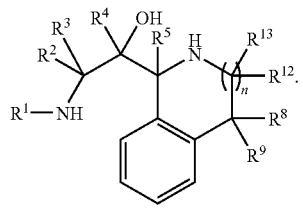

"Fused heteroaryl" means a similar structure, wherein, for example, the phenyl ring is replaced by pyridyl.

The cycloamino ring portion of the compounds of formula I, i.e., the portion of the compound having the structure

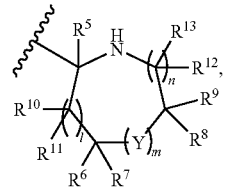

can have multiple oxo substituents, that is, where $R^{19}$ and $R^{11}$, or $R^6$ and $R^7$, or $R^8$ and $R^9$, or $R^{12}$ and $R^{13}$ form —C(O)— groups with the carbons to which they are attached, several such groups can be present on the ring as long the conditions in (C) are met (i.e., a —C(O)— group is not adjacent to Y=—S(O)$_{0-2}$—). For example, $R^6$ and $R^7$, and $R^{12}$ and $R^{13}$ can each form —C(O)— groups with the carbons to which they are attached when m is 0 and $R^8$, $R^9$, $R^{10}$ and $R^{11}$ are hydrogen. Preferably, when compound of formula I comprise —C(O)— group(s) on the cycloamino ring, only 1 or 2 such groups are present, and they are not present on adjacent carbon atoms.

The term "optionally substituted" means optional substitution with the specified groups, radicals or moieties, in available position or positions.

With reference to the number of moieties (e.g., substituents, groups or rings) in a compound, unless otherwise defined, the phrases "one or more" and "at least one" mean that there can be as many moieties as chemically permitted, and the determination of the maximum number of such moieties is well within the knowledge of those skilled in the art. With respect to the compositions and methods comprising the use of "at least one compound of formula I," one to three compounds of formula I can be administered at the same time, preferably one.

As used herein, the term "composition" is intended to encompass a product comprising the specified ingredients in the specified amounts, as well as any product which results, directly or indirectly, from combination of the specified ingredients in the specified amounts.

The wavy line ∿∿ as a bond generally indicates a mixture of, or either of, the possible isomers, e.g., containing (R)- and (S)- stereochemistry. For example,

means containing both

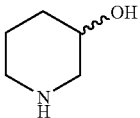

Lines drawn into the ring systems, such as, for example:

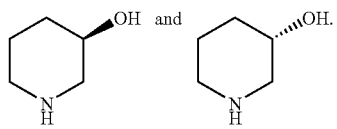

indicate that the indicated line (bond) may be attached to any of the substitutable ring carbon atoms.

As well known in the art, a bond drawn from a particular atom wherein no moiety is depicted at the terminal end of the bond indicates a methyl group bound through that bond to the atom, unless stated otherwise. For example:

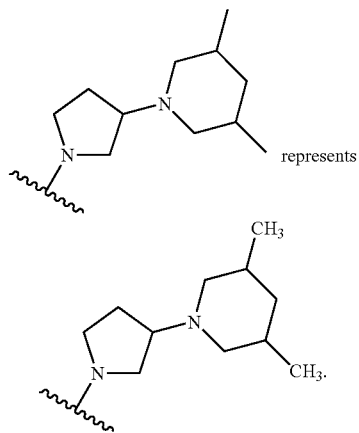

represents

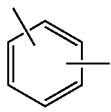

It should also be noted that any heteroatom with unsatisfied valences in the text, schemes, examples, structural formulae, and any Tables herein is assumed to have the hydrogen atom or atoms to satisfy the valences.

Prodrugs and solvates of the compounds of the invention are also contemplated herein. The term "prodrug", as employed herein, denotes a compound that is a drug precursor which, upon administration to a subject, undergoes chemical conversion by metabolic or chemical processes to yield a compound of formula I or a salt and/or solvate thereof. A discussion of prodrugs is provided in T. Higuchi and V. Stella, *Pro-drugs as Novel Delivery Systems* (1987) Volume 14 of the A.C.S. Symposium Series, and in *Bioreversible Carriers in Drug Design*, (1987) Edward B. Roche, ed., American Pharmaceutical Association and Pergamon Press, both of which are incorporated herein by reference thereto.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting BACE-1 and thus producing the desired therapeutic effect in a suitable patient.

The compounds of formula I form salts which are also within the scope of this invention. Reference to a compound of formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the formula I may be formed, for example, by reacting a compound of formula I with an amount of acid or base, such as an equivalent amount, in a medium such as one in which the salt precipitates or in an aqueous medium followed by lyophilization. Acids (and bases) which are generally considered suitable for the formation of pharmaceutically useful salts from basic (or acidic) pharmaceutical compounds are discussed, for example, by S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; in *The Orange Book* (Food & Drug Administration, Washington, D.C. on their website); and P. Heinrich Stahl, Camille G. Wermuth (Eds.), *Handbook of Pharmaceutical Salts: Properties, Selection, and Use*, (2002) Int'l. Union of Pure and Applied Chemistry, pp. 330-331. These disclosures are incorporated herein by reference thereto.

Exemplary acid addition salts include acetates, adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides, hydrobromides, hydroiodides, 2-hydroxyethanesulfonates, lactates, maleates, methanesulfonates, methyl sulfates, 2-naphthalenesulfonates, nicotinates, nitrates, oxalates, pamoates, pectinates, persulfates, 3-phenylpropionates, phosphates, picrates, pivalates, propionates, salicylates, succinates, sulfates, sulfonates (such as those mentioned herein), tartarates, thiocyanates, toluenesulfonates (also known as tosylates) undecanoates, and the like.

Exemplary basic salts include ammonium salts, alkali metal salts such as sodium, lithium, and potassium salts, alkaline earth metal salts such as calcium and magnesium salts, aluminum salts, zinc salts, salts with organic bases (for example, organic amines) such as benzathines, diethylamine, dicyclohexylamines, hydrabamines (formed with N,N-bis(dehydroabietyl)ethylenediamine), N-methyl-D-glucamines, N-methyl-D-glucamides, t-butyl amines, piperazine, phenylcyclohexylamine, choline, tromethamine, and salts with amino acids such as arginine, lysine and the like. Basic nitrogen-containing groups may be quarternized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Compounds of formula I, and salts, solvates and prodrugs thereof, may exist in their tautomeric form (for example, as an amide or imino ether). All such tautomeric forms are contemplated herein as part of the present invention.

All stereoisomers (for example, geometric isomers, optical isomers and the like) of the present compounds (including those of the salts, solvates and prodrugs of the compounds as well as the salts and solvates of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate" "prodrug" and the like, is intended to equally apply to the salt, solvate and prodrug of enantiomers, stereoisomers, rotamers, tautomers, racemates or prodrugs of the inventive compounds.

For the combination aspect, the use of any β-secretase inhibitor other than those of formula I is contemplated; β-secretase inhibitory activity can be determined by the procedures described below. Typical β-secretase inhibitors include, but are not limited to, those disclosed in WO 02/02505, WO 02/02506, WO 02/02512, WO 02/02518, WO 02/02520 and WO 02/088101.

Gamma-secretase inhibitors for use in the combination of this invention can be determined by procedures known in the art. Typical gamma-secretase inhibitors include, but are not limited to, those described in WO 03/013527, U.S. Pat. No. 6,683,091, WO 03/066592, U.S. Ser. No. 10/663,042, filed Sep. 16, 2003, WO 00/247671, WO 00/050391, WO 00/007995 and WO 03/018543.

HMG-CoA reductase inhibitors for use in combination with compounds of formula I include the "stains," e.g., atorvastatin, lovastatin. simvistatin, pravastatin, fluvastatin and rosuvastatin.

Cholinesterase inhibitors for us in the combination include acetyl- and/or butyrylchlolinesterase inhibitors. Examples of cholinesterase inhibitors are tacrine, donepezil, rivastigmine, galantamine, pyridostigmine and neostigmine.

Non-steroidal anti-inflammatory agents for use in combination with compounds of formula I include ibuprofen, naproxen, diclofenac, diflunisal, etodolac, flurbiprofen, indomethacin, ketoprofen, ketorolac, nabumetone, oxaprozin, piroxicam, sulindac, tolmetin, celecoxib and rofecoxib. A suitable N-methyl-D-aspartate receptor antagonist is, for example, memantine. Anti amyloid antibodies are described, for example, in Hock et al, *Nature Medicine,* 8 (2002), p. 1270-1275.

Compounds of formula I can be made using procedures known in the art. The following reaction schemes show typical procedures, but those skilled in the art will recognize that other procedures can also be suitable. In the Schemes and in the Examples below, the following abbreviations are used methyl: Me; ethyl: Et; propyl: Pr; butyl: Bu; benzyl: Bn
high pressure liquid chromatography: HPLC
liquid chromatography mass spectrometry: LCMS
thin layer chromatography: TLC
preparative thin layer chromatography: PTLC
room temperature: RT
hour: h
minute: min
retention time: $t_R$
1-hydroxybenzotriazole: HOBt
1-(3-dimethylaminopropyl)-3-ethylcarbodiimide methiodide: EDCI
1-(3-dimethylaminopropyl)-3-ethylcarbodiimide hydrochloride: EDC
ethyl acetate: EtOAc
tetrahydrofuran: THF
N,N-dimethylformamide: DMF
n-butyllithium: n-BuLi
1-hydroxy-1-oxo-1,2-benzodioxol-3(1H)-one: IBX
triethylamine: $NEt_3$ or $Et_3N$
dibutylboron triflate: $Bu_2BOTf$
methanol: MeOH
diethyl ether: $Et_2O$
acetic acid: AcOH
diphenylphosphoryl azide: DPPA
isopropanol: iPrOH
benzyl alcohol: BnOH
1-hydroxy-7-azabenzotriazole: HOAt
O-(7-azabenzotriazol-1-yl)-N,N,N',N'-tetramethyluronium hexafluorophosphate: HATU
benzotriazole-1-yl-oxy-trispyrrolidinophosphonium hexafluorophosphate: PyBOP
trifluoroacetic acid: TFA
tertiary butyloxycarbonyl: Boc
benzyloxycarbonyl: Cbz
dimethylsulfoxide: DMSO
diisopropylethylamine: DIEA
lithium diisopropylamide: LDA
tris-(2-aminoethyl)aminomethyl polystyrene (PS-trisamine)
methylisocyanate polystyrene (PS-NCO)
tetrabutylammonium iodide: TBAI
para-toluenesulfonic acid: pTSA
trimethylsilyl chloride: TMSCl General Schemes:

In Schemes 1 to 4, the variable "$R^x$" is used in place of variables $R^6$-$R^{13}$ in order to simplify the structures. "PG" refers to an amine protecting group. Examples of suitable amine protecting groups are Boc and Cbz; Bn can also be used for secondary amines, and (Bn)$_2$ can also be used for primary amines (in which case, the PG-NH— portion of the structures shown in the schemes below would become (PG)$_2$-N—, i.e., (Bn)$_2$-N—).

In Scheme 1, an asymmetric aldol condensation affords an adduct II. Hydrolysis of the chiral auxiliary gives a carboxylic acid III. Curtius rearrangement of III affords an oxazolidinone IV, which can be hydrolyzed to an amino alcohol V. N-derivatization of V to introduce a benzoyl substituent followed by deprotection gives the product. Alternatively, IV can be converted to VIII by N-derivatizion prior to hydrolysis. In cases where hydroxyl group protection is required, benzylation of III gives the intermediate VI. This intermediate can be converted through the sequence of Curtius rearrangement to give VII, deprotection to V, N-derivatization to give VIII and deprotection to give product. Alternatively, hydroxyl protection of II gives an intermediate IX which is transformed into the product by an analogous sequence.

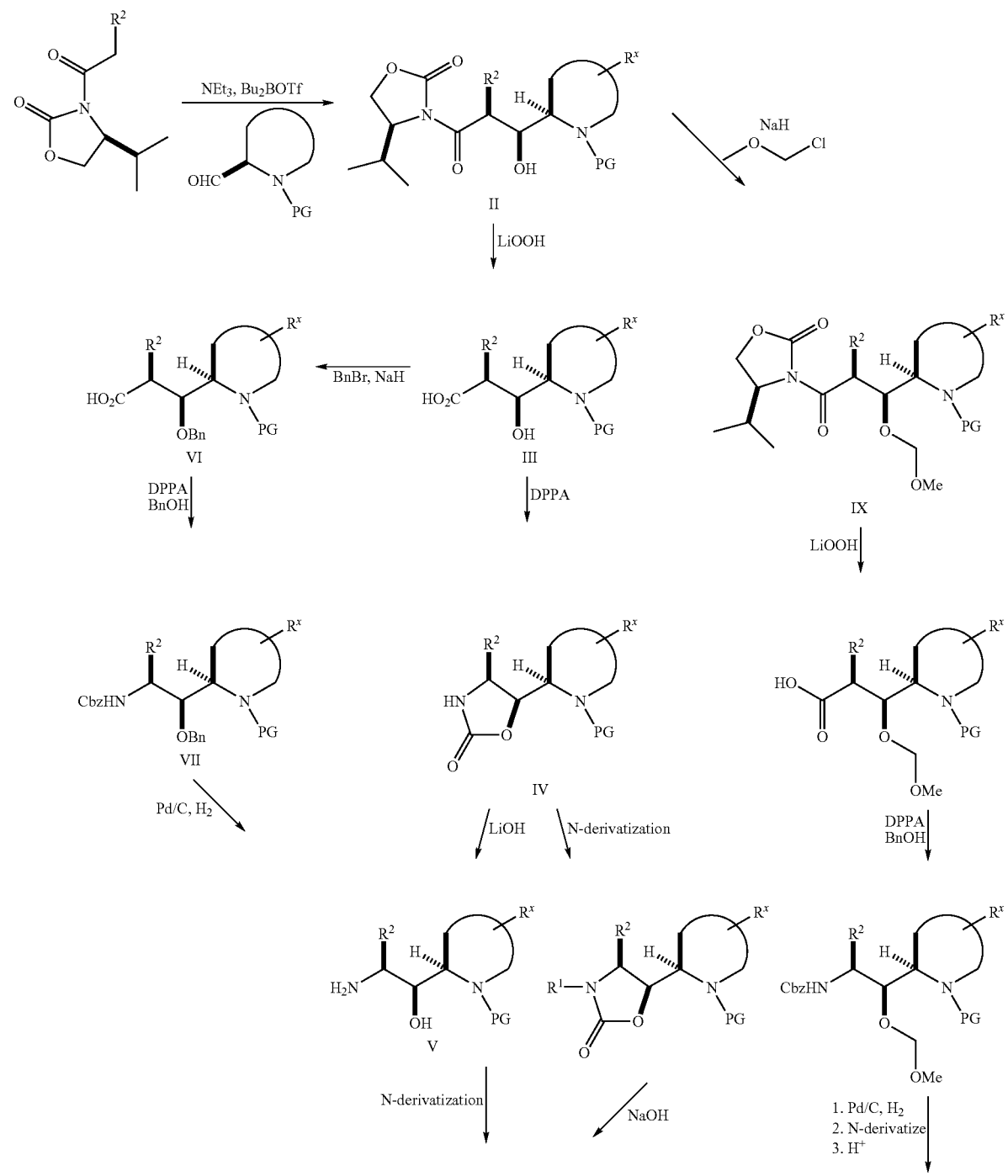

Scheme 1

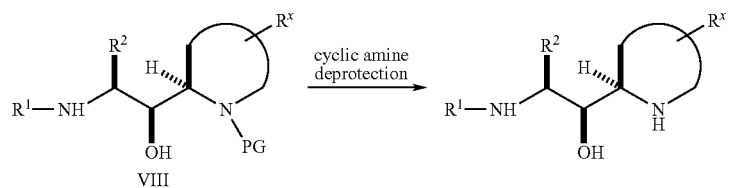

In Scheme 2, a lithio derivative of a 2-halopyridine is added to a protected α-amino aldehyde derivative to give an adduct X. The protected primary amine of X is deprotected and the resultant amine is acylated to the desired derivative XI. Hydrogenation of the pyridine ring affords a piperidine derivative, the nitrogen of which can be protected for ease of purification to give XII. Deprotection of the cyclic amine XII gives the desired product.

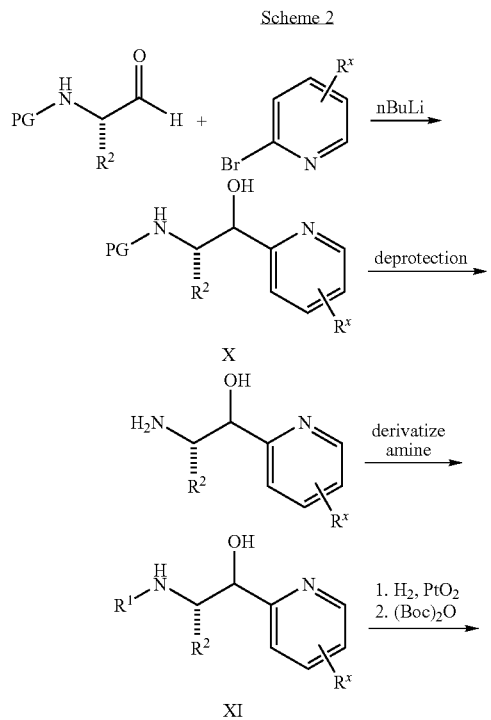

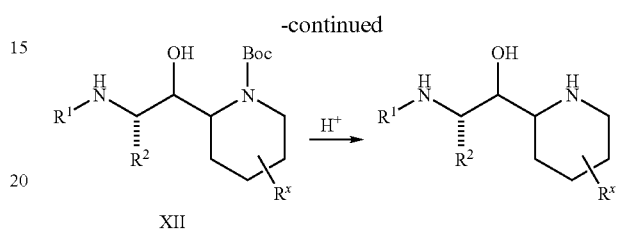

In Scheme 3, a 2-lithio derivative of 4-chloropyridine is added to a protected amino aldehyde to give the intermediate XIII. The chloro substituent of XIII can be displaced by an alkoxide ($R^{17x}$—OH, wherein $R^{17x}$ is as defined for $R^{17}$, but not H) to give an ether XIV. Deprotection and derivatization of the primary amine, followed by reduction of the pyridine ring gives the corresponding piperidine product. Alternatively, the chloro substituent of XIII can be cross-coupled with an organozinc reagent under palladium catalysis to give a coupled product XV. Deprotection and derivatization of the primary amine, followed by reduction of the pyridine ring gives the corresponding piperidine product. The chloro substituent of XIII can be displaced by an amide ($NH(R^{15})C(O)R^{17x}$, wherein $R^{17x}$ is as defined above) under copper (I) catalysis to form a pyridine substituted by a nitrogen-linked substituent, XVI. Intermediate XVI can be subsequently transformed to the product by deprotection and derivatization of the primary amine and reduction of the pyridine ring. Reaction of chloro intermediate XIII with carbon monoxide and methanol under palladium catalysis in the presence of a base gives a methyl ester XVII. Intermediate XVII can be subsequently transformed to the product by deprotection and derivatization of the primary amine, and reduction of the pyridine ring to give a piperidine.

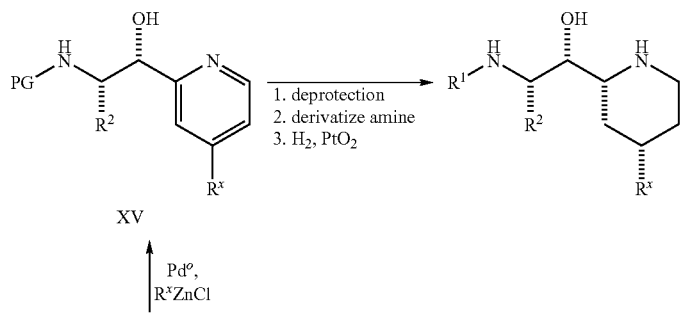

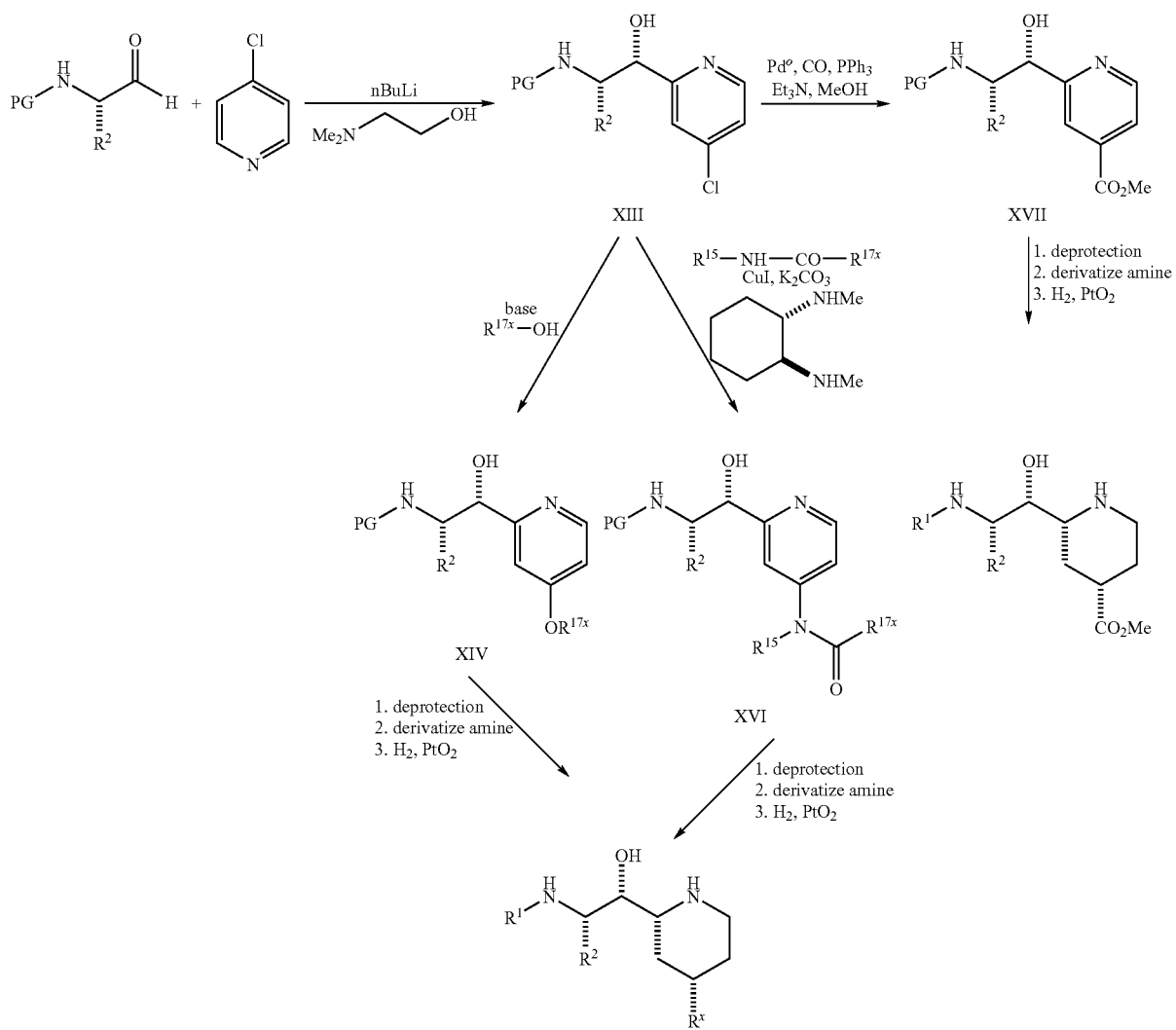

In Scheme 4, The 2-lithio derivative of 2,5-dibromopyridine is added to a protected amino aldehyde to give the intermediate XVIII. Deprotection to give a primary amine is followed by amine derivatization to give XIX. The bromo substituent of XIX is then transformed to a carbon-substituted product XX by a cross-coupling reaction under palladium catalysis. Hydrogenation of the pyridine ring of XX affords a substituted piperidine product. XIX can also be coupled to terminal alkynes ($R^{xa}$=H, wherein $R^{xa}$ is selected from the substituents as defined for $R^6$-$R^{11}$ suitable for preparing an alkyne) and the acetylenic intermediate XXI can be reduced to the product.

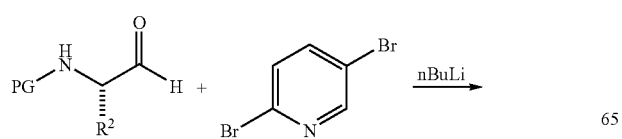

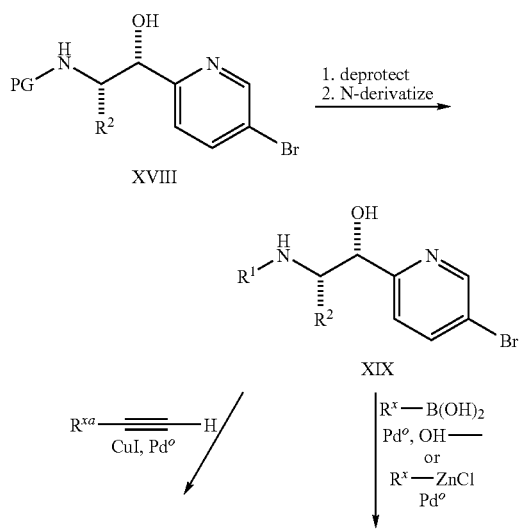

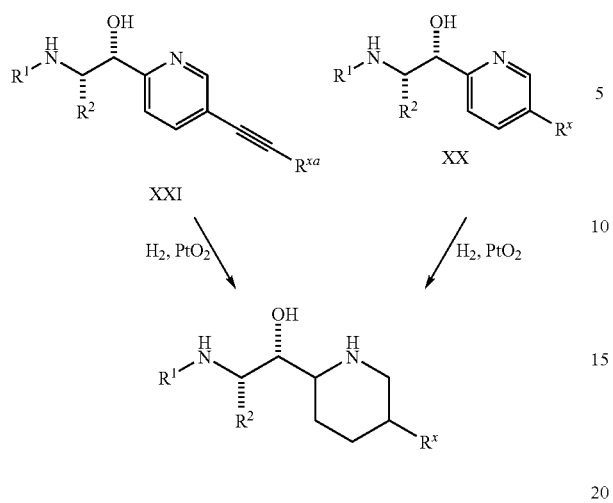

In Scheme 5, the anion generated from a 3-oxo cyclic amine derivative is added to a protected α-amino aldehyde derivative to give an adduct XXII. Deprotection of XXII followed by derivatization of the primary amine affords the desired product.

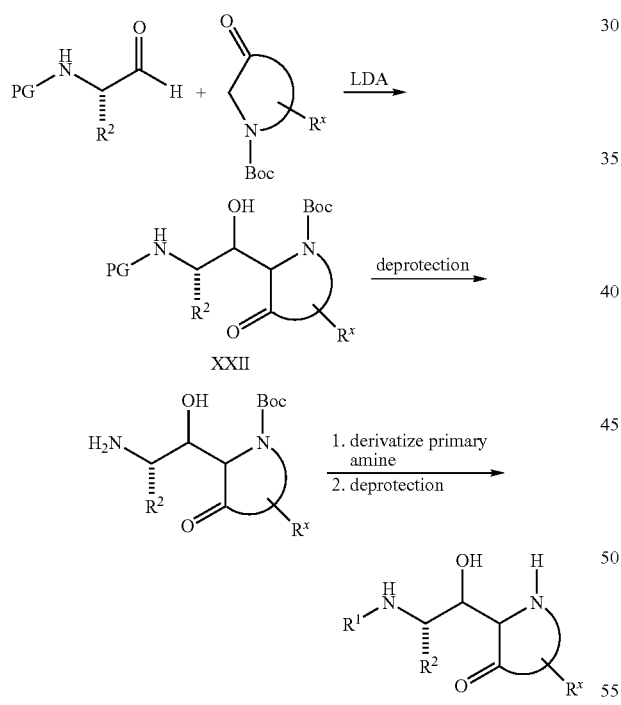

In Scheme 6, lithiated XXIII is added to a protected N,N-dibenzyl aminoaldehyde to give a product XXIV. Removal of the N,N-dibenzyl protecting group from XXIV by hydrogenolysis followed by reduction of the piperazinone oxo group with borane-dimethylsulfide gives a piperazine product XXV. Derivatization of the primary amine of XXV and hydrogenolysis of the piperazine benzyl group gives intermediate XXVI. Derivatization of the piperazine nitrogen of XXVI followed by deprotection gives the piperazine product.

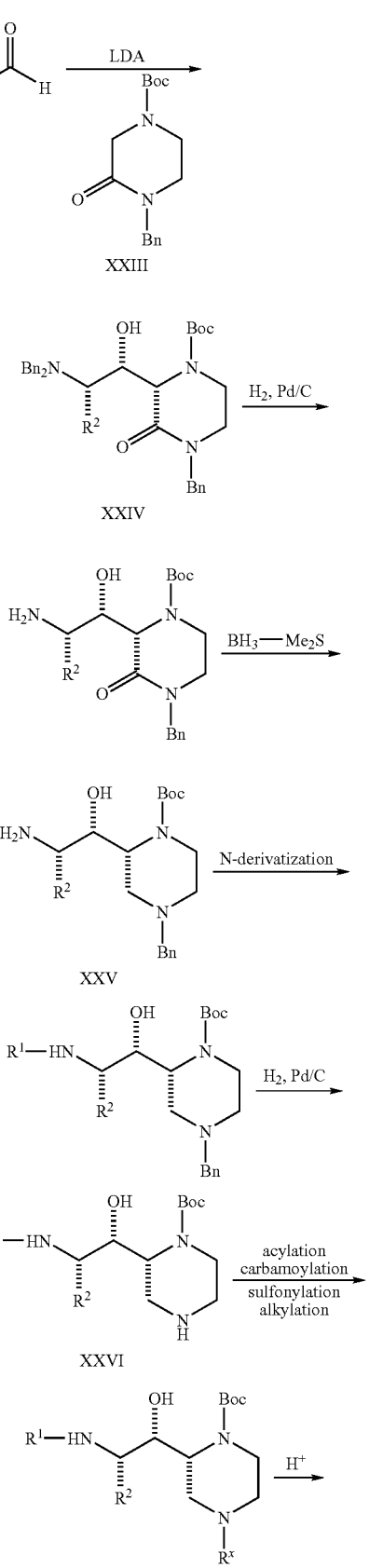

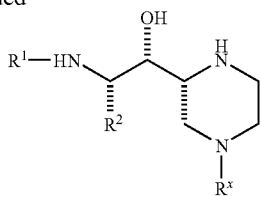

In Scheme 7, N-Boc-2-tert-butyldimethylsilyloxypyrrole is added to a protected α-amino aldehyde in the presence of an appropriate Lewis acid, for example boron trifluoride etherate, to give an unsaturated lactam XXVII. Reduction of the olefin, deprotection and derivatization of the primary amine affords oxo-substituted products. Alternatively, following saturation of the double bond of XXVII, protection of the alcohol gives XXVIII. Intermediate XXVIII can be subjected to reduction of the lactam carbonyl group by DIBALH, which upon treatment with acidic methanol gives XXIX. Treatment XXIX with an organometallic reagent in the presence of a Lewis acid affords a substituted pyrrolidine XXX. Deprotection to give the primary amine, N-derivatization and deprotection give the product. Alternatively, cyclopropanation of XXVII gives a fused product that is subsequently deoxygenated, deprotected and derivatized to afford the desired compounds.

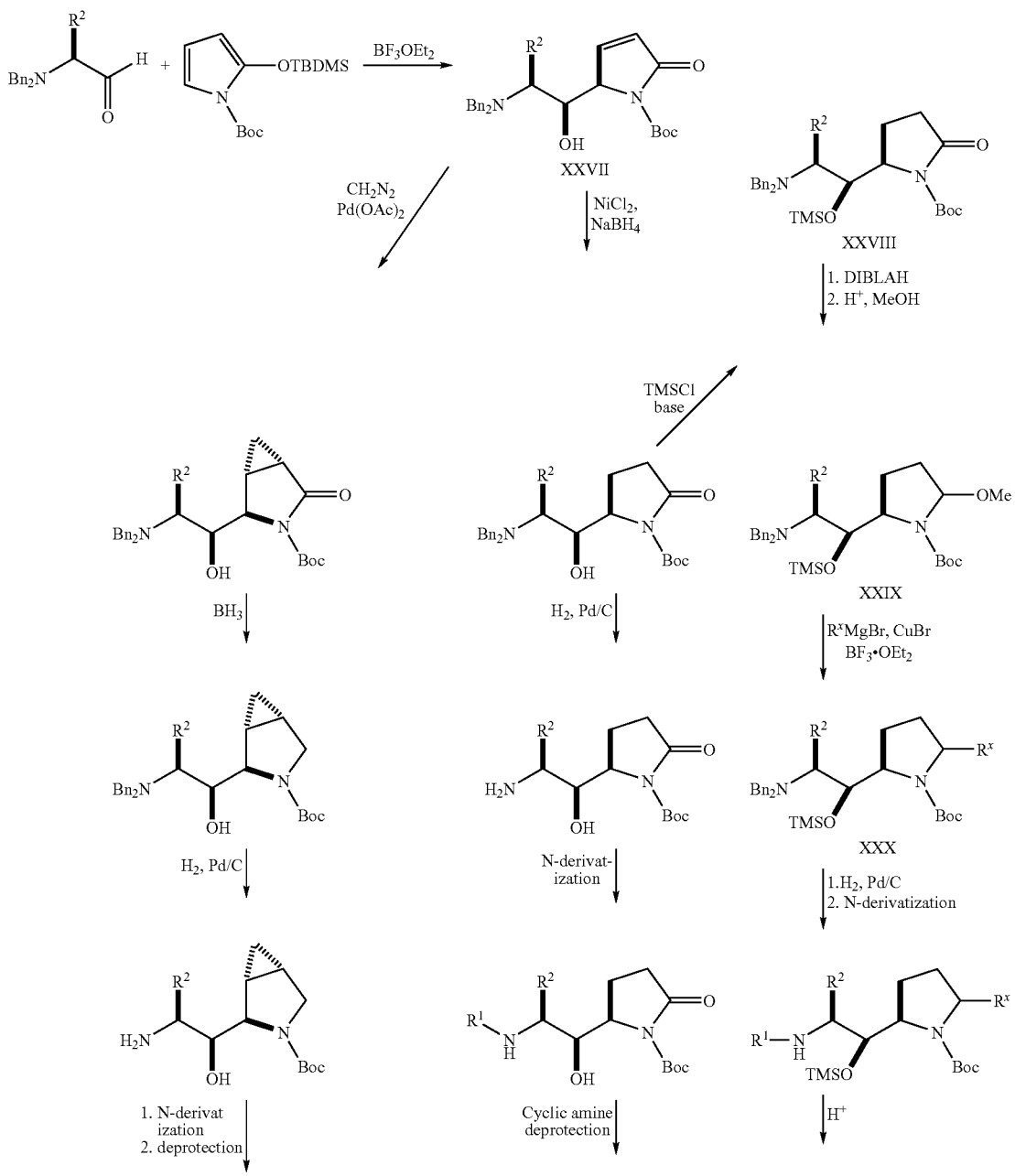

Scheme 7

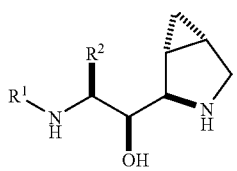 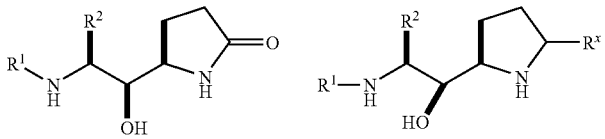

The conditions for the LCMS and RP-HPLC analyses in the preparations and examples below are as follows:

Conditions A: 5 minute gradient from 10%→95% CH₃CN/H₂O with 0.1% TFA, then 2 min isocratic at 95% CH₃CN/H₂O with 0.1% TFA, 1.0 ml/min flow rate on an analytical C18 reverse-phase column.

Conditions B: 3 minute gradient from 5%→95% CH₃CN/H₂O with 0.1% TFA, then 1 min isocratic at 95% CH₃CN/H₂O with 0.1% TFA, 0.8 ml/min flow rate on an analytical C18 reverse-phase column.

Conditions C: gradient from 10%→95% CH₃CN/H₂O with 0.1% HCO₂H, 25 ml/min flow rate on a preparative C18 reverse-phase column.

Conditions D: gradient from 5%→95% CH₃CN/H₂O with 0.1% HCO₂H, 20 ml/min flow rate on a preparative C18 reverse-phase column.

Conditions E: 5 minute gradient from 10%→90% CH₃CN/H₂O with 0.1% TFA, 0.4 ml/min flow rate on an analytical C18 reverse-phase column.

Preparation 1

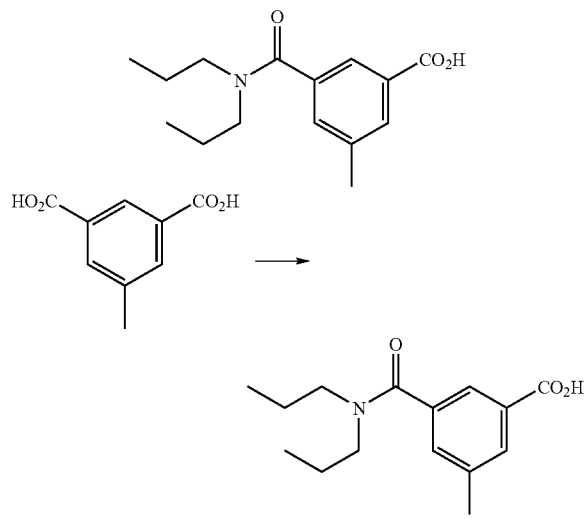

To a RT solution of 5-methylisophthalic acid (6.68 g, 37.1 mmol) and DIEA (19.7 ml, 14.4 g, 111 mmol) in CH₂Cl₂ (74 ml) were added sequentially di-n-propyl-amine (5.1 ml, 3.75 g, 37.1 mmol), HOBt (5.01 g, 37.1 mmol) in two portions, and EDCI (7.11 g, 37.1 mmol) in four portions. The reaction mixture was stirred for 24 h, then diluted with 1N HCl. The mixture was stirred vigorously for 15 min, and the copious solid that precipitated was removed by filtration. The filtrate was diluted with water, and the aqueous phase was adjusted to pH ~1. The phases were separated and the aqueous layer extracted twice with CH₂Cl₂. The combined organics were dried (MgSO₄), filtered, and concentrated. This crude residue was purified by column chromatography (silica, 0→100% EtOAc/hexanes) to give a semi-solid that was further recrystallized from 15% EtOAc/hexanes to give the product (4.5 g). Additional product (2.4 g) was obtained by a second column chromatography of the crystallization mother liquor. These two samples were combined (6.9 g total mass, 26.2 mmol, 71%). LCMS (Conditions A): $t_R$=3.9 min; (M+H)⁺=264.

Preparation 2

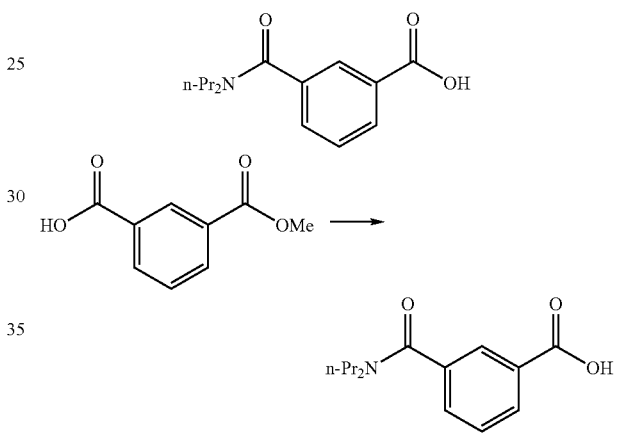

To a solution of isophthalic acid monomethyl ester (1.00 g, 5.55 mmol) in DMF (10 ml) were added sequentially di-n-propylamine (0.77 ml, 0.56 g, 5.6 mmol), HOBt (1.12 g, 8.32 mmol), and EDCI (1.60 g, 8.32 mmol). The resulting mixture was stirred for 3 h and then diluted with water and EtOAc. The phases were separated, and the aqueous portion was extracted with EtOAc (2×). The combined organic fractions were washed with 1 N HCl and brine, dried over MgSO₄, filtered, and concentrated. The residue was purified by column chromatography (silica, 5%→25% EtOAc/hexanes) to give a product (1.34 g, 5.09 mmol, 92%).

To a solution of the above material (1.34 g, 5.09 mmol) in MeOH (10 ml) was added a 1 N aq. LiOH solution (7.63 ml, 7.63 mmol). After 18 h, the mixture was adjusted to pH ~1 with 1 N HCl, and EtOAc was added. The phases were separated, and the aqueous layer was extracted with EtOAc (2×). The combined organic portions were washed with brine, dried over MgSO₄, filtered, and concentrated. The crude residue was purified by column chromatography (silica, 0%→50% EtOAc/hexanes) to give the desired product (1.02 g, 4.09 mmol, 80%). LCMS (Conditions A): $t_R$=3.98 min; (M+H)⁺=250; ¹H NMR (CDCl₃, 400 MHz) δ 12.00 (br s, 1H), 8.08 (m, 2H), 7.60 (m, 1H), 7.48 (apparent t, J=8.0 Hz, 1H), 3.47 (br t, J=72 Hz, 2H), 3.14 (br t, J=7.2 Hz, 2H), 1.70 (m, 2H), 1.52 (m, 2H), 0.97 (br t, J=7.2 Hz, 3H), 0.72 (br t, J=7.2 Hz, 3H).

Preparation 3

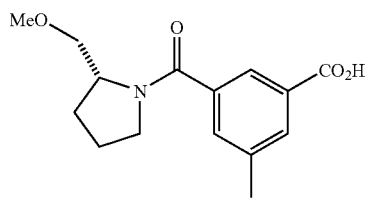

By essentially the same procedure set forth in Preparation 1, the above compound was prepared from 5-methylisophthalic acid and (R)-2-(methoxymethyl)pyrrolidine.

Preparation 4

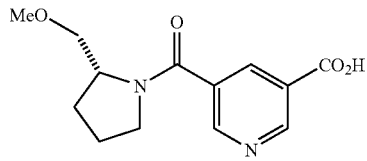

By essentially the same procedure set forth in Preparation 1, the above compound was prepared from pyridine-3,5-dicarboxylic acid and (R)-2-(methoxymethyl)pyrrolidine.

Preparation 5

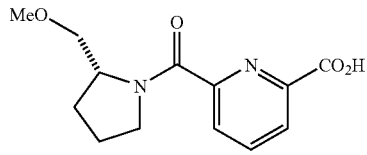

By essentially the same procedure set forth in Preparation 1, the above compound was prepared from pyridine-2,6-dicarboxylic acid and (R)-2-(methoxymethyl)pyrrolidine.

Preparation 6

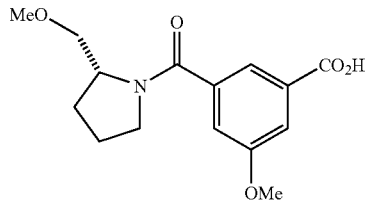

By essentially the same procedure set forth in Preparation 1, the above compound was prepared from 5-methoxyisophthalic acid and (R)-2-(methoxymethyl)pyrrolidine.

Preparation 7

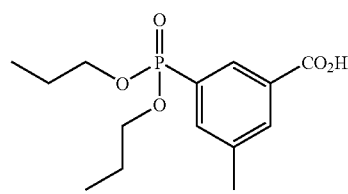

Step 1

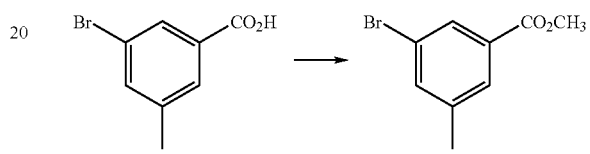

To a RT solution of 3-bromo-5-methylbenzoic acid (1 g, 4.6 mmol) in MeOH/toluene (1/5, 12 ml) was added slowly (trimethysilyl)diazomethane (2.0 M in hexanes, 2.76 ml, 5.527 mmol). The mixture was stirred for 2 h at RT. The solvent was evaporated under reduced pressure and the residue was diluted with EtOAc and water. The organic layer was separated and the aqueous layer was extracted twice with EtOAc. The combined organic layers were dried over $Na_2SO_4$ and concentrated. The crude material was purified by chromatography over silica gel (100% hexane) to give the product (1.1 g, 100%). MS m/e 230 (M+H)$^+$.

Step 2

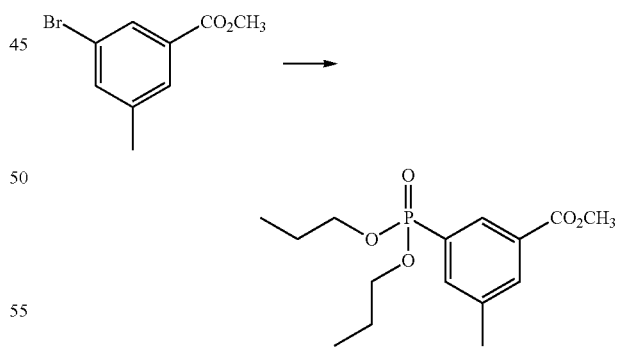

A mixture of the product of Step 1 (283 mg, 1.24 mmol), dipropyl phosphite (303 μL, 1.85 mmol), tetrakis(triphenylphosphine) palladium (289 mg, 0.25 mmol), and $Et_3N$ (10 ml) were added to a sealed tube. The mixture was heated at 100° C. for 3.5 h. After the reaction mixture had cooled to RT, the mixture was poured into water (10 ml). After extraction with EtOAc (3×25 ml), the combined organic layers were dried over $Na_2SO_4$, and concentrated. The crude material was purified by chromatography over silica gel (35% EtOAc/hexanes) to give the product (328 mg, 85%). MS m/e 315 (M+H)+.

Step 3

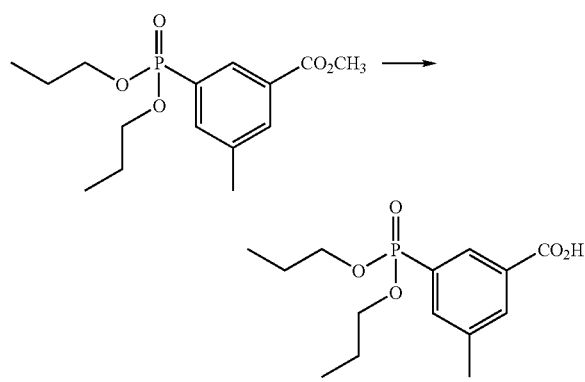

To a solution of the product of Step 2 (100 mg, 0.32 mmol) in MeOH (5 ml) was added 1N LiOH (2 ml, 2 mmol). The mixture was stirred for 2 h at RT. After evaporation of the solvent, the residue was dissolved in EtOAc, and acidified to pH ~2 with 1 N HCl. The organic layer was separated and the aqueous layer was extracted twice with EtOAc. The combined organic layers were dried over Na$_2$SO$_4$ and concentrated to give the product. MS m/e 301 (M+H)+.

Preparation 8

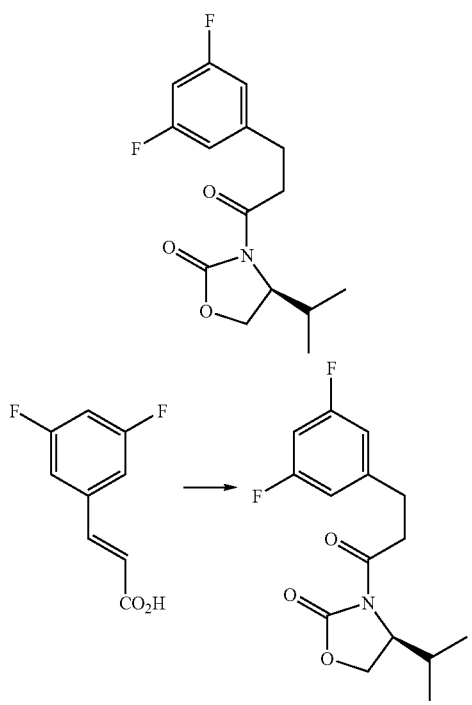

According to the literature (Kruse et al., *J. Med. Chem.* (1987), 30, 486-494), a solution of 3,5-difluorocinnamic acid (9.94 g, 53.9 mmol) in THF (100 ml) was hydrogenated over 10% Pd/C (1.50 g) at 50 psi of H$_2$ pressure for 5 h at RT. The mixture was filtered and concentrated under reduced pressure to yield the 3-(3,5-difluoro-phenyl)propionic acid (10.9 g, 100%). Oxalyl chloride (13 ml, 150 mmol) was slowly added to a solution of the acid (10.9 g, 53.9 mmol) in THF (220 ml) at 23° C., followed by the addition of a catalytic amount of DMF (1 drop). After 90 min at RT, the volatiles were removed under reduced pressure and the resulting residue was twice coevaporated with dry benzene to yield 3-(3,5-difluorophenyl)-propionyl chloride as a yellow oil (11.91 g, 100%). The acid chloride was used in the ensuing step without further purification. The acylation was carried out in analogy to the literature (Pettit et al. *Synthesis* (1996), 719-725). A solution of (S)-(-)-4-isopropyl-2-oxazolidinone (6.46 g, 50 mmol) in THF (150 ml) was stirred under argon and cooled to −78° C. n-BuLi (2.45 M in hexanes, 20.8 ml, 50.96 mmol) was added dropwise, followed by a solution of the previously prepared 3-(3,5-difluorophenyl)-propionyl chloride in THF (8 ml). After warming the reaction to 23° C. over 15 h, the reaction was quenched with saturated aq. NH$_4$Cl (30 ml), followed by removal of the volatiles in vacuo. The slurry was extracted with CH$_2$Cl$_2$ (2×), and the combined organic layers washed with 1M NaOH (2×) and brine, dried (Na$_2$SO$_4$) and concentrated in vacuo Purification of the residue by chromatography over silica gel (15→30% EtOAc/hexanes) gave the product (14.27 g, 48 mmol, 96%). $^1$H NMR (400 MHz, CDCl$_3$) δ 6.73 (m, 2H), 6.59 (m, 1H), 4.37 (m, 1H), 4.17-4.25 (m, 2H), 3.24 (m, 1H), 3.16 (m, 1H), 2.93 (m, 2H), 2.30 (m, 1H), 0.86 (d, 3H, J=6.8 Hz), 0.80 (d, 3H, J=6.8 Hz); LCMS (Conditions A): t$_R$=4.47 min: 595 (2M+H)+, 298 (M+H)+.

Preparation 9

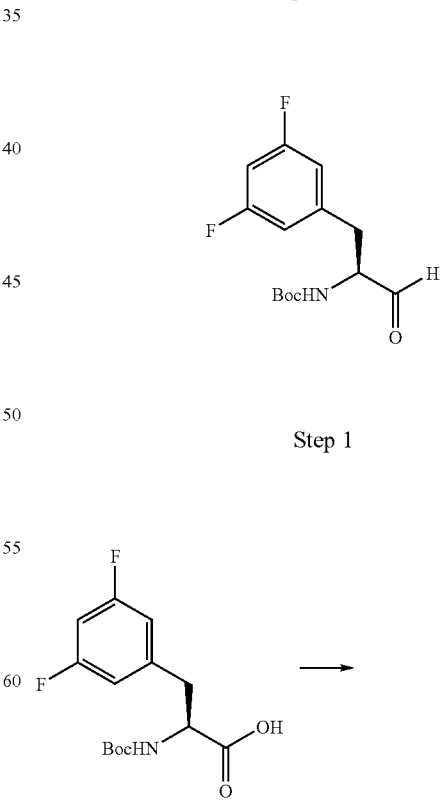

Step 1

Step 1

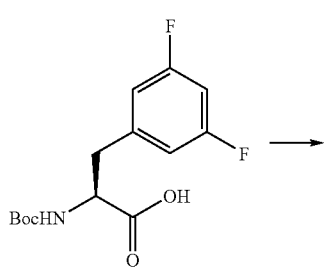

Trimethylsilyldiazomethane (2.0 M Hexanes, 95 ml, 190 mmol) was added to a solution of Boc-(L)-3,5-difluorophenylalanine (40 g, 133 mmol) in MeOH (50 ml) and toluene (250 ml) at 0° C. After 60 min at RT, AcOH was added to quench the excess trimethylsilyldiazomethane, and the reaction mixture was concentrated under vacuum to give the methyl ester in quantitative yield (42.3 g). 4 M HCl/dioxane (150 ml, 600 mmol) was added to a solution of the methyl ester (42.3 g) in 20% MeOH/CH$_2$Cl$_2$ (130 ml) at 0° C., and the reaction was stirred for 4 h at RT. The reaction was concentrated under vacuum to give the HCl salt in quantitative yield (33.4 g, 133 mmol). LCMS (Conditions A): 2.62 min; 431 (2M+H)$^+$, 216 (M+H)$^+$

Step 2

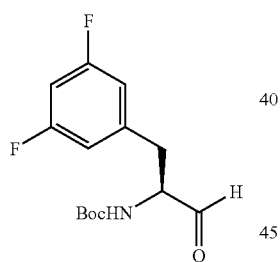

NaHCO$_3$ (55.9 g, 665 mmol) and BnBr (68.2 g, 399 mmol) were added to a solution of the product of Step 1 (33.4 g, 133 mmol) in THF (600 ml) and DMSO (150 ml) at RT. The reaction mixture was stirred for 24 h at 70° C., then cooled to RT and diluted with water (400 ml). After stirring for 1 h at RT, the layers were separated and the aqueous layer extracted

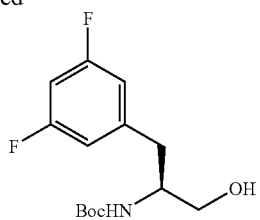

To a stirred mixture of (S)-Boc-3,5-difluorophenylalanine (20.00 g, 66.4 mmol) in MeOH (50 ml) and toluene (250 ml) at 0° C. was added (trimethylsilyl)diazo-methane (2.0 M in hexane, 53 ml, 106 mmol) in portions. After the addition, the reaction was stirred for about 0.5 h at RT, quenched with glacial AcOH (1 ml) and concentrated in vacuo. The residue was dissolved in anhydrous THF (200 ml), cooled to 0° C., and LiAlH$_4$ (2.52 g, 66.4 mmol) was added in portions. After the addition, the reaction was allowed to stir at 0° C. for 20 min, then quenched with of 15% aq. NaOH (2.0 ml) and H$_2$O (8.0 ml). The resulting slurry was filtered, the residue washed with THF, and the combined filtrate and washings were concentrated in vacuo to give the product as a white solid (17.65 g, 93%). $^1$H NMR (CDCl$_3$) δ 6.73 (m, 2H), 6.62 (m, 1H), 4.75 (s, br, 1H), 3.80 (s, br, 1H), 3.61 (m, 1H), 3.52 (m, 1H), 2.80 (m, 2H), 1.37 (s, 9H). MS m/e 288 (M+H)$^+$.

Step 2

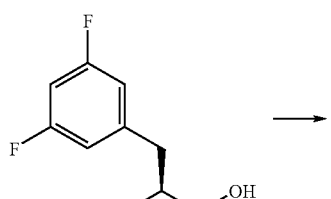

The product of Step 1 (3.00 g, 10.5 mmol), EtOAc (150 ml) and IBX (8.78 g, 31.4 mmol) was stirred at 95° C. for 3.5 h. The reaction mixture was allowed to cool to RT, filtered and concentrated in vacuo to provide the product as white solid (2.98 g, 100%). $^1$H NMR (CDCl$_3$) δ 9.59 (s, 1H), 6.65 (m, 3H), 5.03 (m, 1H), 4.35 (m, 1H), 3.13 (m, 1H), 3.01 (m, 1H), 1.39 (s, 9H).

Preparation 10

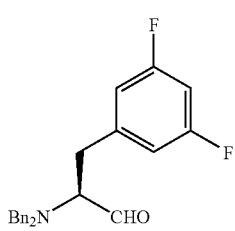

with EtOAc (3×). The combined organic layers were washed (NaHCO$_3$), dried (MgSO$_4$) and concentrated, and the residue chromatographed (SiO$_2$, 0% to 30% EtOAc/Hexanes) to give the intermediate N,N-dibenzylated methyl ester in 75% yield (39.4 g, 99.6 mmol). LCMS (Conditions A) 5.90 min; 396 (M+H)$^+$ LiAlH$_4$ (6.49 g, 171 mmol) was added to a solution of the methyl ester (45.0 g, 114 mmol) in THF (500 ml) at 0° C. After the addition was completed, the reaction mixture was stirred at RT for 5 h, then carefully quenched with water (5 ml), 15% NaOH (10 ml) and an additional amount of water (7 ml). After vigorously stirring the suspension, the mixture was filtered, and the filtrate concentrated. The resulting residue was chromatographed over silica (0% to 50% EtOAc/Hexanes) to give the product in 71% yield (34.8 g, 94.7 mmol). LCMS (Conditions A) 4.53 min; 368 (M+H)$^+$ Step 3

DMSO (4.45 ml, 62.7 mmol) in CH$_2$Cl$_2$ (10 ml) was added to a solution of oxalylchloride (2.70 ml, 31.3 mmol) in CH$_2$Cl$_2$ (60 ml) at −78° C. After 10 min, a solution of the product of Step 2 (10.0 g, 27.2 mmol) in CH$_2$Cl$_2$ (40 ml) was added. The reaction mixture was stirred for 90 min at −78° C., followed by addition of DIEA (18.8 ml, 108 mmol). The reaction mixture was stirred for 2 h at RT, then quenched with water. The aqueous layer was extracted with CH$_2$Cl$_2$, and the combined organic layers washed (2× water, 2×NH$_4$Cl, 1× brine), dried (MgSO$_4$), and concentrated to give the product (10.32 g, >theoretical yield). $^1$H NMR (400 MHz, CDCl$_3$) δ=9.72 (s, 1 H), 7.33-7.24 (m, 10H), 6.65-6.61 (m, 3H), 3.82 (d, J=13.6 Hz, 2H), 3.68 (d, J=14 Hz, 2H), 3.51 (m, 1H), 3.10 (m, 1H), 2.86 (m, 1H).

Preparation 11

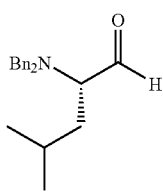

Step 1

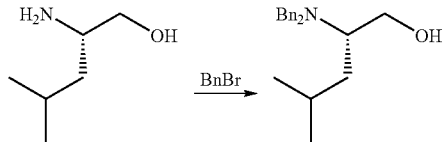

L-Leucinol (5.27 g, 45.0 mmol) was added to a stirred solution of K$_2$CO$_3$ (17.76 g, 128.5 mmol) in water (25 ml) at RT and the mixture was heated to 65° C. A solution of benzyl bromide (15.44 g, 90.27 mmol) in EtOH (12 ml) was added and the mixture was stirred at 65° C. for 1 h. The mixture was diluted with CH$_2$Cl$_2$ (50 ml) and water (25 ml), the aqueous layer was extracted with CH$_2$Cl$_2$ (50 ml) and the combined organic layers were dried (MgSO$_4$), concentrated, and purified by column chromatography (SiO$_2$, gradient EtOAc/Hexanes 0-8%) to give the product (12.63 g, 94%). MS m/e 298 (M+H)$^+$.

Step 2

The product of Step 1 was converted to the aldehyde by essentially the procedure of Preparation 10, Step 3, and was used directly.

Preparation 12

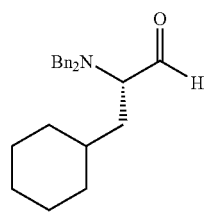

Step 1

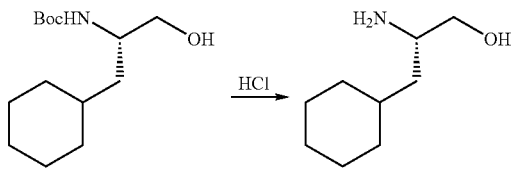

A mixture of (S)-2-t-butoxycarbonylamino-3-cyclohexyl-1-propanol (4.00 g, 15.5 mmol) in CH$_2$Cl$_2$ (10 ml) and 4N HCl in dioxane (10 ml) was stirred at RT for 16 h. The mixture was diluted with CH$_2$Cl$_2$ (40 ml) and washed with aqueous NH$_4$OH (30 ml). The aqueous layer was extracted with CH$_2$Cl$_2$ (40 ml) and the combined organic layer was dried (MgSO$_4$) and concentrated to give the product (2.78 g, 100%). MS m/e 158 (M+H)$^+$ Step 2

The product of Step 1 was dibenzylated in analogy to the procedure of Preparation 11, Step 1. The dibenzylated product was converted to the desired aldehyde in analogy to the procedure of Preparation 10, Step 3.

Example 1

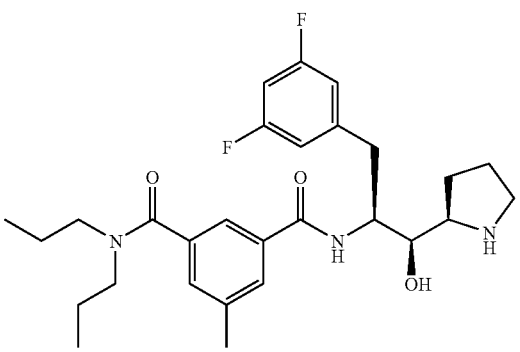

Step 1

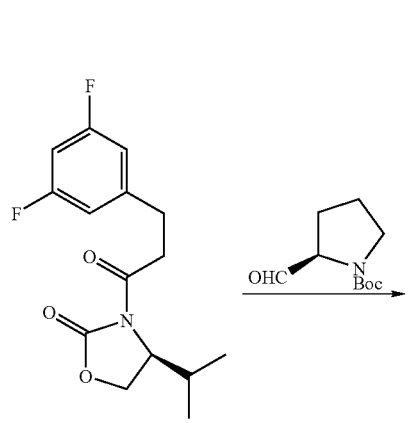

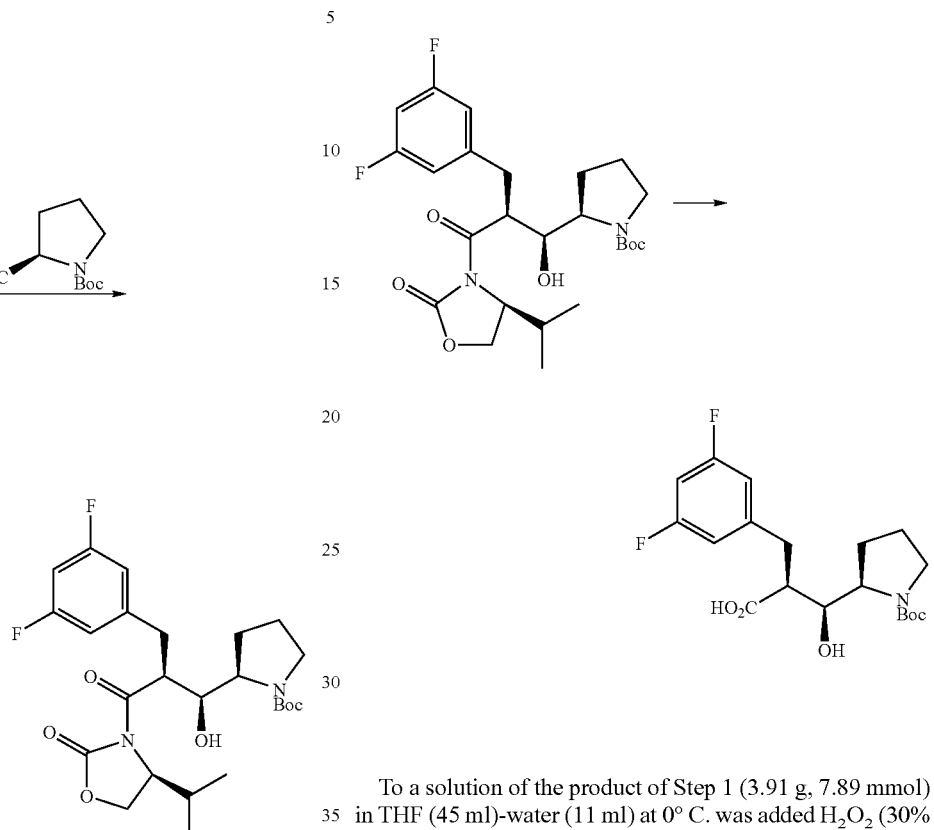

Step 2

The aldol reaction was carried out in analogy to the literature (Pettit et al. *Synthesis* (1996), 719-725). NEt$_3$ (2.0 ml, 14.44 mmol) was added to a solution of Preparation 8 (3.31 g, 11.16 mmol) in CH$_2$Cl$_2$ (46 ml) at 0° C., followed by dropwise addition of Bu$_2$BOTf (1.0 M in CH$_2$Cl$_2$, 12.0 ml, 12 mmol). After 45 min at 0° C., the yellow solution was cooled to −78° C., and a solution of N-(tert-butoxy-carbonyl)-D-prolinal (2.46 g, 12.34 mmol) in CH$_2$Cl$_2$ (5 ml) was added. The reaction was stirred for 1 h at −78° C., 2 h at 0° C. and 1 h at 23° C., and was quenched with MeOH (75 ml)—phosphate buffer (pH 7.0, 25 ml). After cooling the solution to −10° C., a solution of H$_2$O$_2$ (30% in water, 25 ml)—MeOH (50 ml) was added such that the internal temperature remained below 4° C. After stirring for 60 min at 23° C., the volatiles were removed in vacuo, and the aqueous residue was extracted with Et$_2$O (3×), dried (Na$_2$SO$_4$) and concentrated under reduced pressure. Purification of the residue by chromatography over silica gel (20→30% EtOAc/hexanes) gave the title compound (3.03 g, 6.1 mmol, 61%) along with recovered imide (1.98 g, 6.66 mmol). $^1$H NMR (400 MHz, CDCl$_3$) δ 6.83 (m, 2H), 6.51 (m, 1H), 4.57 (m, 1H), 4.33 (m, 1H), 3.94-4.15 (m, 3H), 3.80 (m, 1H), 3.23-3.39 (m, 4H), 2.99 (t, 1H, J=12.8 Hz), 1.98 (m, 1 H), 1.97 (m, 1H), 1.76 (m, 3H), 1.48 (s, 9H), 0.73 (d, 3H, J=6.8 Hz), 0.29 (d, 3H, J=8.8 Hz); LCMS (Conditions A): t$_R$=4.65 min, 497 (M+H)$^+$, 441 (M−Bu+H)$^+$, 397 (M−Boc+H)$^+$.

To a solution of the product of Step 1 (3.91 g, 7.89 mmol) in THF (45 ml)-water (11 ml) at 0° C. was added H$_2$O$_2$ (30% in water, 3.9 ml), followed by an aqueous solution of LiOH (378 mg, 15.78 mmol in 24 ml water, sonicated to completely dissolve LION). After 18 h at 0° C., the reaction was quenched with saturated aqueous Na$_2$SO$_3$ and stirred at 23° C. for 2 h. After removal of all volatiles, the residue was diluted with NaHCO$_3$, extracted with CH$_2$Cl$_2$ (3×), acidified to pH 2 (1 N HCl), salted out with NaCl (s) and extracted with Et$_2$O (3×). The combined organic layers were washed with water (1×) and brine (1×), dried (Na$_2$SO$_4$) and concentrated in vacuo to yield the product (2.24 g, 5.80 mmol, 74%); $^1$H NMR (400 MHz, CDCl$_3$) δ 6.71 (m, 2H), 6.57 (m, 1H), 4.09 (m, 1H), 3.90 (m, 1H), 3.49 (m, 1H), 3.10-3.23 (m, 2H), 2.86 (m, 1H), 2.64 (m, 1H), 1.47-2.00 (m, 4H), 1.48 (s, 9H); LCMS (Conditions A): t$_R$=3.93 min, 386 (M+H)$^+$, 330 (M−Bu+H)$^+$, 286 (M−Boc+H)$^+$.

Step 3

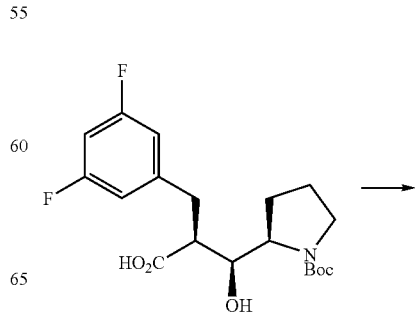

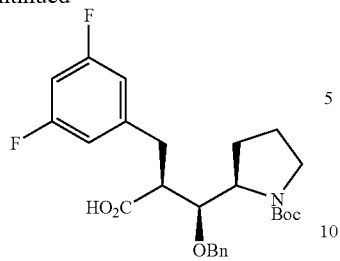

To a solution of the product of Step 2 (2.23 g, 5.80 mmol) in DMF (20 ml) at −78° C. was added NaH (60%, 510 mg, 12.75 mmol), followed by benzyl bromide (810 μl, 6.81 mmol). The reaction was warmed to 23° C. over 18 h. The volatiles were removed in vacuo, and the residue was taken up in water-Et$_2$O. The aqueous layer was extracted with Et$_2$O (2×), adjusted to pH 3 (1 M HCl), extracted with EtOAc (3×), and the combined organic layers were dried (MgSO$_4$) and concentrated under reduced pressure. Purification of the residue by chromatography over silica gel (10-450% EtOAc/hexanes containing 1% AcOH) gave recovered starting material (372 mg, 0.97 mmol) and the product (616 mg, 1.30 mmol, 22%); $^1$H NMR (400 MHz, CDCl$_3$, complicated by the presence of rotamers) δ 8.0-9.0 (bs, 1H), 7.21 (m, 5H), 6.68 (m, 2H), 6.60 (m, 1H), 4.50-4.64 (m, 2H), 3.60-3.83 (m, 1H), 3.37-3.60 (m, 2H), 3.07-3.24 (m, 2H), 2.82 (m, 1H), 2.60 (m, 1H), 1.96-2.08 (m, 1H), 1.79-1.96 (m, 2H), 1.66 (m, 1H), 1.40 (m, 9H); LRMS 498 (M+Na)$^+$, 420 (M−Bu+H)$^+$, 376 (M−Boc+H)$^+$.

Step 4

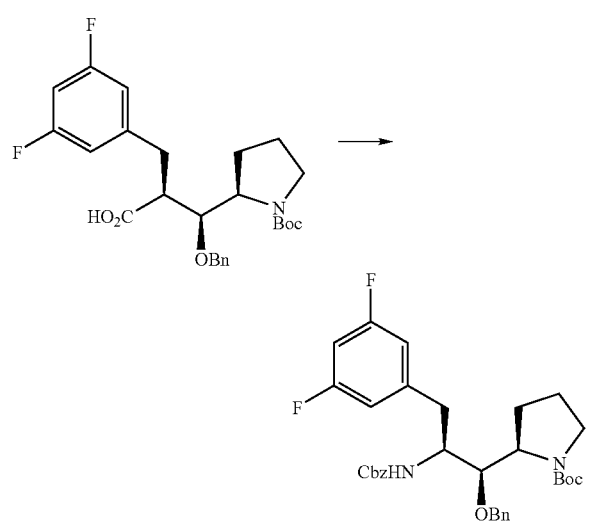

NEt$_3$ (155 μL, 1.12 mmol) and DPPA (145 μL, 0.67 mmol) were added to the product of Step 3 (265 mg, 0.56 mmol) in toluene (3 ml) at 23° C. After 3 h at 95° C., BnOH (240 μl, 2.24 mmol) was added, followed by stirring at 80° C. for 18 h. After removing the volatiles in vacuo, the residue was purified by chromatography over silica gel (5→10% EtOAc/hexanes) and normal-phase HPLC (1→10% iPrOH/hexanes) to give the product (103 mg, 0.18 mmol, 32%) $^1$H NMR (400 MHz, CDCl$_3$) δ 7.17-7.30 (m, 10H), 6.57-6.70 (m, 3H), 5.30 (m, 1 NH), 4.85-5.05 (m, 2H), 4.40-4.56 (m, 2H), 4.05 (m, 1H), 3.65-3.95 (m, 2H), 3.00-3.60 (m, 3H), 2.40-2.60 (m, 1H), 2.05 (m, 1H), 1.55-1.95 (m, 3H), 1.41 (s, 9H); LCMS (Conditions A): t$_R$=5.18 min, 581 (M+H)$^+$, 525 (M−Bu+H)$^+$, 481 (M−Boc+H)$^+$.

Step 5

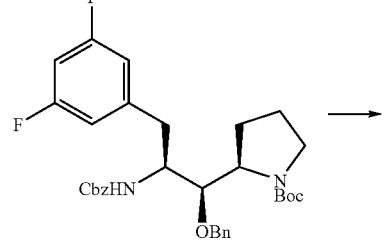

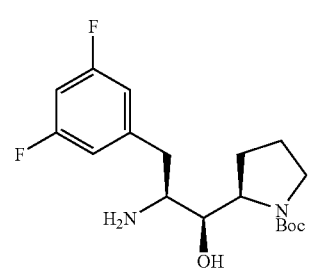

A solution of the product of Step 4 (100 mg, 172 μmol) in MeOH (4 ml) was hydrogenated over 20% Pd(OH)$_2$/C (40 mg) at 1 atm of H$_2$ pressure for 18 h. The mixture was filtered and concentrated under reduced pressure to yield the product (61 mg, 171 mmol, 100%) which was used without further purification in the next step.

Step 6

The product of Step 5 (25 mg, 71 μmol), Preparation 1 (21 mg, 78 μmol), NEt$_3$ (60 μL, 427 μmol and HOAt (22 mg, 157 μmol) were dissolved in DMF (2.0 ml), and HATU (55 mg, 142 μmol) was added. After stirring for 21 h at RT, the reaction was quenched with water. The aqueous layer was extracted with EtOAc (3×), and the combined organic layers were washed with water (2×) and brine (1×), dried (Na$_2$SO$_4$) and concentrated under reduced pressure. The residue was purified by chromatography over silica gel (20→60% EtOAc/hexanes) followed by normal-phase HPLC (20→60% EtOAc/hexanes). The intermediate (20 mg) was treated with 20% TFA/CH$_2$Cl$_2$ (1 ml) for 1 h at 23° C., followed by removal of volatiles under vacuum. Subsequently, the residue was dissolved in 1 M HCl/MeOH, stirred for 15 min, then concentrated under vacuum to give the hydrochloride salt of the product as an oil (18 mg, 33 μmol, 46% for three steps). LCMS (Conditions A): t$_R$=4.28 min, 502 (M+H)$^+$.

Example 1A

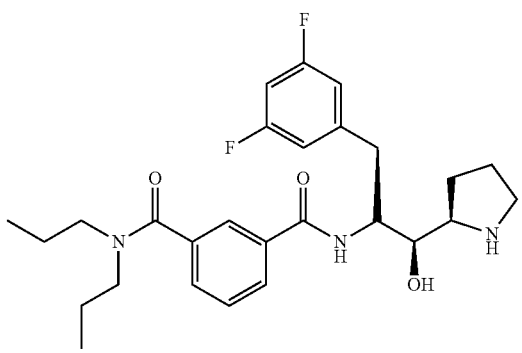

The product was obtained by using a procedure analogous to that of Example 1, Step 6, except that Preparation 2 was used in place of Preparation 1. LCMS (Conditions A): $t_R$=4.17 min, 488 (M+H)$^+$.

Example 1B

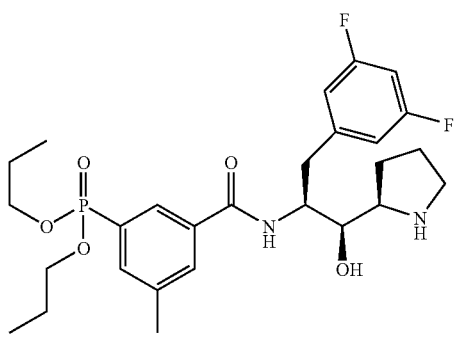

The product was obtained by using a procedure analogous to that of Example 1, Step 6, except that Preparation 7 was used in place of Preparation 1. $^1$H NMR (400 MHz, CD$_3$OD) δ 7.77 (m, 1H), 7.67 (m, 2H), 6.82 (m, 2H), 6.66 (m, 1H), 4.09 (m, 1H), 4.04 (m, 1H), 3.97 (m, 4H), 3.71 (m, 1H), 3.36 (m, 1H), 3.29 (m, 1H), 2.85 (m, 1H), 2.40 (s, 3H), 1.94-2.16 (m, 4H), 1.66 (m, 4H), 1.23 (m, 1H), 0.90 (m, 6H); LCMS (Conditions A): $t_R$=4.45 min, 539 (+H), 522 (M-H$_2$O+H)$^+$.

Example 2

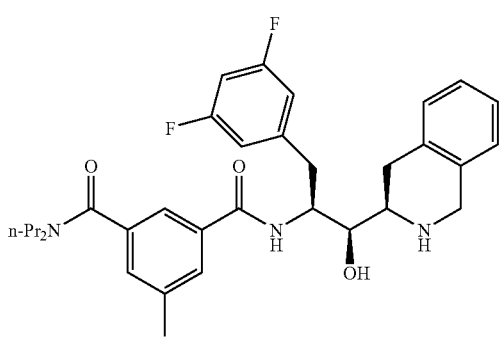

Step 1

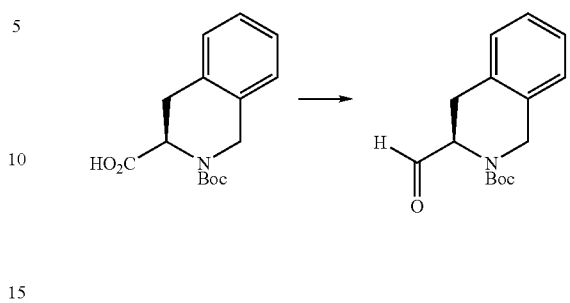

To a solution of N-Boc-D-1,2,3,4-tetrahydroisoquinoline-3-carboxylic acid (2.60 g, 9.38 mmol) in toluene/MeOH (5/1, 50 ml) at RT was added (trimethysilyl)-diazomethane (2 M in hexanes) until a bright yellow color persisted in the reaction. The reaction was stirred for 5 min at RT, then AcOH was added dropwise until the yellow color faded completely. The solution was concentrated, and the methyl ester was used without purification.

To a 0° C. solution of a portion of the methyl ester (2.30 g, 7.90 mmol) in THF (40 ml) was added solid LiAlH$_4$ (600 mg, 15.8 mmol) in two portions. The reaction was allowed to warm to RT. After 18 h, the reaction was quenched by slow addition of water (1 ml), followed by 25% w/v aq. NaOH (1.5 ml), and finally more water (2 ml). The resulting mixture was stirred vigorously for 1 h at RT and then filtered and concentrated. The residue was purified by column chromatography (silica, 0-+65% EtOAc/hexanes) to give the product (500 mg, 1.89 mmol, 24%). LCMS (Conditions A): $t_R$=4.2 min; (M+H)$^+$=264.

To a -78° C. solution of oxalyl chloride (215 μl, 318 mg, 2.51 mmol) in CH$_2$Cl$_2$ (5.5 ml) was added DMSO (222 μl, 245 mg, 3.13 mmol). After 5 min, a -78° C. solution of the product of the previous transformation (550 mg, 2.09 mmol) in CH$_2$Cl$_2$ (5 ml) was added via cannula. After 40 min at -78° C., DIEA (1.1 ml, 810 mg, 6.3 mmol) was added, and the reaction was removed from the cooling bath. After 10 min at RT, the mixture was diluted with water and additional CH$_2$Cl$_2$. The phases were separated, and the aqueous phase was extracted once with CH$_2$Cl$_2$. The organic portions were combined, washed with brine, dried over MgSO$_4$, filtered, and concentrated. The crude product was used in subsequent steps without further purification.

Step 2

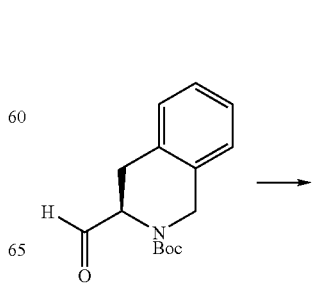

-continued

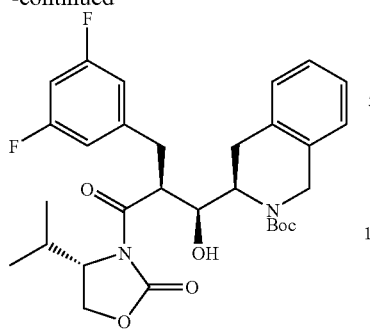

To a −20° C. solution of Preparation 8 (745 mg, 2.51 mmol) in CH$_2$Cl$_2$ (10.5 ml) was added Et$_3$N (0.43 ml, 320 mg, 3.1 mmol). After 5 min, di-n-butylboron triflate (1 M in CH$_2$Cl$_2$, 2.72 ml, 2.72 mmol) was added via syringe over 2 min. The reaction was transferred to an ice/brine bath, stirred for 2 h, and then cooled to −78° C. At that time, a 0° C. solution of the final product of Step 1 (assumed 2.09 mmol) in CH$_2$Cl$_2$ (3 ml) was added dropwise via cannula over 5 min, followed by a CH$_2$Cl$_2$ rinse (1 ml). The resulting mixture was treated in a manner similar to that in Example 1, Step 2, through the extraction with Et$_2$O. The combined organic fractions were washed with sat. aq. NaHCO$_3$ and brine, then dried over MgSO$_4$, filtered, and concentrated. The crude material was purified by column chromatography (silica, 0→75% EtOAc/hexanes) to give the product (668 mg, 1.20 mmol, 57%). LCMS (Conditions A): t$_R$=5.3 min; (M+H)$^+$=559.

Step 3

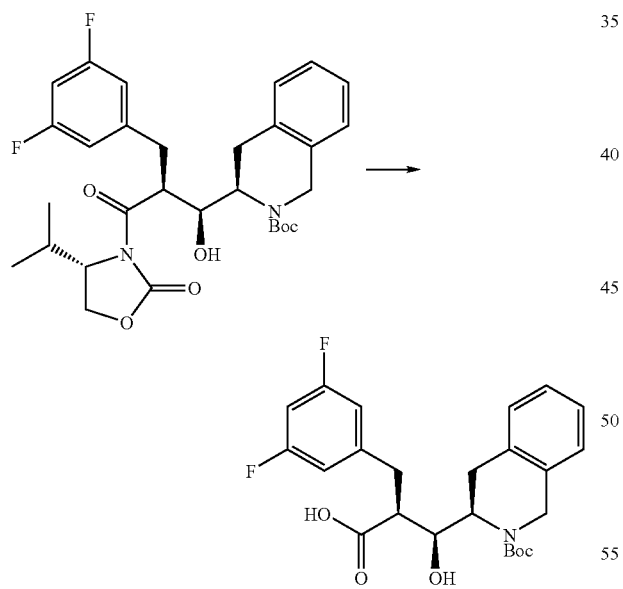

To a 0° C. solution of the product of Step 2 (610 mg, 1.09 mmol) in THF/water (5/1, 6 ml) was added 35% aq. H$_2$O$_2$ (0.44 ml) followed by a sonicated mixture of LiOH (77 mg, 1.8 mmol) in water (2 ml). The reaction was stirred at 0° C. for 8 h, and was then diluted with an aq. Na$_2$SO$_3$ solution (1 g in 5 ml water) and warmed to RT. After 18 h, the mixture was diluted with 1 N HCl and CH$_2$Cl$_2$. The phases were separated and the aqueous layer extracted three times with CH$_2$Cl$_2$. The combined organic fractions were washed with brine, dried over MgSO$_4$, filtered, and concentrated. The crude residue was purified by column chromatography (silica, 0→100% EtOAc/hexanes) to give the product (305 mg, 0.682 mmol, 63%). LCMS (Conditions A): t$_R$=4.5 min; (M+H)$^+$=448.

Step 4

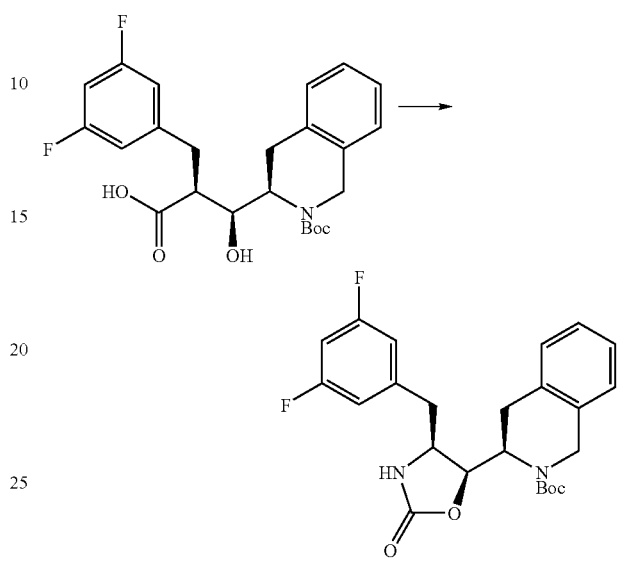

To a RT suspension of the product of Step 3 (305 mg, 0.682 mmol) in toluene (3.5 ml) at RT was added Et$_3$N (0.19 ml, 140 mg, 1.4 mmol) followed by DPPA (0.18 ml, 225 mg, 0.82 mmol). The mixture became homogeneous. After 5 min at RT, the mixture was placed in a pre-heated oil bath (80° C.). After 4 h, the reaction was cooled to RT and concentrated directly without workup. This crude material was purified by column chromatography (silica, 0→100% EtOAc/hexanes) to give the product (300 mg, 0.68 mmol, 99%). LCMS (Conditions A): t$_R$=4.9 min; (M+H)$^+$=445.

Step 5

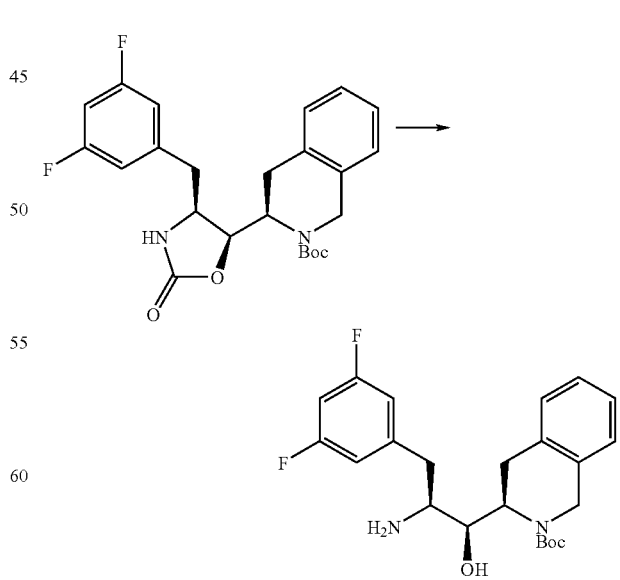

To a solution of the product of Step 4 (180 mg, 0.405 mmol) in ethanol (2 ml) was added 1 N aq. LiOH (2.0 ml, 2.0 mmol).

The resulting mixture was heated to 85° C. After 4 h, the reaction was cooled to RT and diluted with water and EtOAc. The phases were separated and the aqueous fraction was extracted four times with EtOAc. The organic portions were combined, washed with brine, dried over MgSO$_4$, filtered, and concentrated. The crude residue was purified by HPLC (Conditions C) to give the product (138 mg, 0.297 mmol, 73%). LCMS (Conditions A): $t_R$=4.6 min; (M+H)$^+$=419.

Step 6

To a RT solution of the product of Step 5 (30 mg, 0.065 mmol) in DMF (0.75 ml) were added sequentially Preparation 1 (18 mg, 0.068 mmol), Et$_3$N (18 μl, 13 mg, 0.13 mmol), HOBt (11 mg, 0.081 mmol), and EDCI (15 mg, 0.081 mmol). The reaction was stirred for 18 h at RT, then diluted with H$_2$O and EtOAc. The resulting mixture was stirred vigorously until both phases became clear. The phases were separated, and the aqueous phase was extracted with EtOAc (3×). The combined organic portions were washed with 1 N HCl and brine, dried over MgSO$_4$, filtered, and concentrated. The residue was purified by HPLC (Conditions C) to give the desired compound (31 mg, 0.047 mmol, 72%).

To a RT solution of the above material (31 mg, 0.047 mmol) in CH$_2$Cl$_2$ (1 ml) was added 4 N HCl/dioxane (1 ml). After 2.5 h at RT, the reaction was concentrated to give the product. LCMS (Conditions A): $t_R$=4.7 min; (M+H)$^+$=564; $^1$H NMR (CD$_3$OD, 300 MHz) δ 7.58 (s, 1H), 7.37 (s, 1H), 7.27-7.16 (m, 5H), 6.91 (m, 2H), 6.74 (apparent tt, J=9.3, 2.4 Hz, 1H), 4.49 (m, J=15.9 Hz, 1H) overlapping 4.42-4.30 (m, 2H), 4.23 (dd, J=10.2, 2.4 Hz, 1H), 3.76-3.56 (m, 4H), 3.44 (m, 3H), 3.36-3.22 (m, 2H), 3.11 (apparent t, J=7.8 Hz, 2H), 2.91 (dd, J=13.8, 11.1 Hz, 1 H), 2.37 (s, 3H), 1.68 (m, 2H), 1.47 (m, 2H), 0.97 (t, J=7.2 Hz, 3H), 0.64 (t, J=7.2 Hz, 3H).

Example 2B

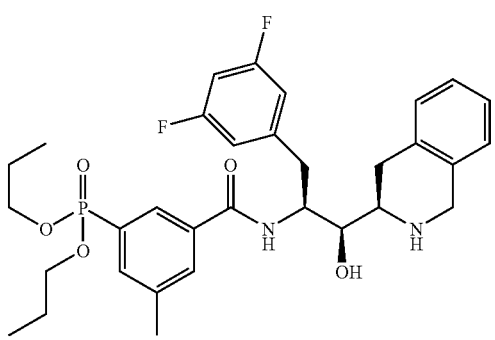

The product was obtained by using a procedure analogous to that of Example 2, Step 6, except that Preparation 7 was used in place of Preparation 1. LCMS (Conditions A): $t_R$=4.6 min; (M+H)$^+$=601; $^1$H NMR (CD$_3$OD, 300 MHz) δ 7.81-7.66 (m, 3H), 7.22 (m, 4H), 6.92 (m, 2H), 6.76 (apparent ft, J=9.6, 2.4 Hz, 1H), 4.42 (ABq, J$_{AB}$=15.6 Hz, Δv$_{AB}$=50.1 Hz, 2H) overlapping 4.40 (m, 1H), 4.23 (dd, J=9.9 Hz, 1.8 Hz, 1H), 3.96 (m, 4H), 3.70 (m, 4H), 3.45 (dd, J=14.1, 3.0 Hz, 1H), 3.40-3.21 (m, 2H), 2.90 (dd, J=13.5, 11.1 Hz, 1H), 2.41 (s, 3H), 1.66 (m, 4H), 0.92 (t, J=7.2 Hz, 3H) overlapping 0.90 (t, J=7.2 Hz, 3H).

Example 3

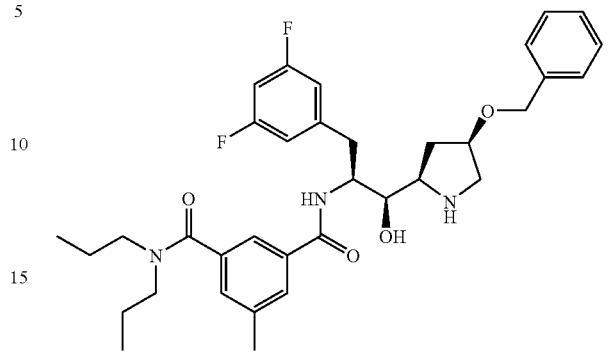

Step 1

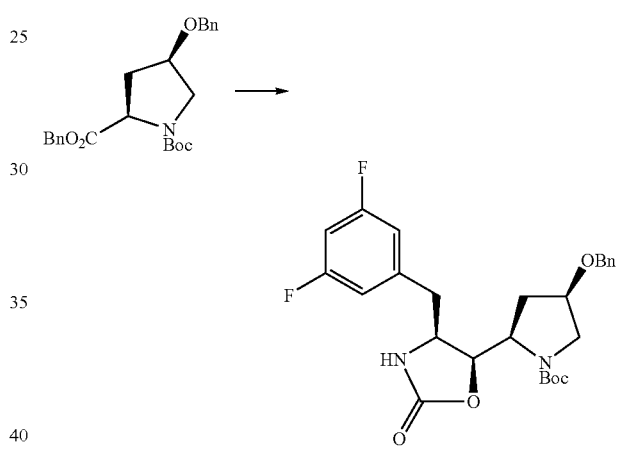

(4R)-1-tert-butoxycarbonyl-4-benzyloxy-D-proline benzyl ester (Bellier et al. *J. Med. Chem.* (1997), 40, 3947-3956) was converted into the desired product by essentially the procedure of Example 2, Steps 1 through 4, except that (4R)-1-tert-butoxycarbonyl-4-benzyloxy-D-proline benzyl ester was used in place of methyl N-Boc-D-1,2,3,4-tetrahydroquinoline-3-carboxylate. LCMS (Conditions A) $t_R$=4.90 min: 489 (M+H)$^+$, 433 (M–tBu+H), 389 (M–Boc+H)$^+$ Step 2

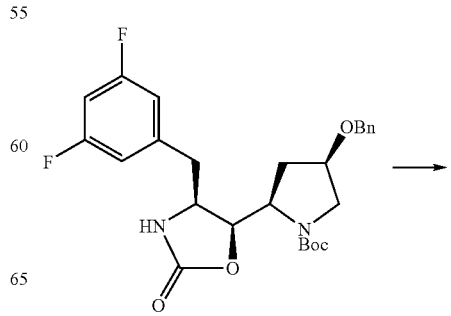

-continued

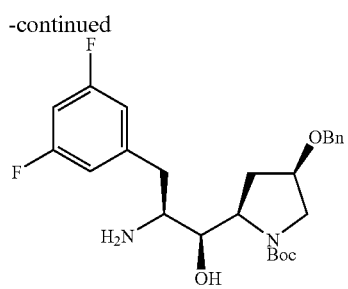

The product of Step 1 was converted into the desired product by essentially the same procedure used in Example 2, step 5. LCMS (Conditions A) $t_R$=4.84 min: m/e 925 (2M+H)$^+$, 463 (M+H)$^+$, 407 (M−tBu+H), 363 (M−Boc+H)$^+$.

Step 3

The product of Step 2 was subjected to essentially the procedure described in Example 2, Step 6 to give the product. $^1$H NMR (400 MHz, CD$_3$OD) δ 7.64 (bs, 1H), 7.20-7.40 (m, 8H), 6.87 (m, 2H), 6.64 (m, 1H), 4.52 (m, 2H), 4.31 (m, 1H), 4.22 (m, 1H), 4.09 (m, 1H), 3.80 (m, 1H), 3.44 (m, 2H), 3.14 (m, 2H), 2.89 (m, 1H), 2.39 (m, 2H; s, 3H), 2.20 (m, 1H), 1.68 (m, 2H), 1.49 (m, 2H), 0.96 (m, 3H), 0.62 (m, 3H); LCMS (Conditions A): $t_R$=4.99 min, m/e 608 (M+H)$^+$.

Example 3A

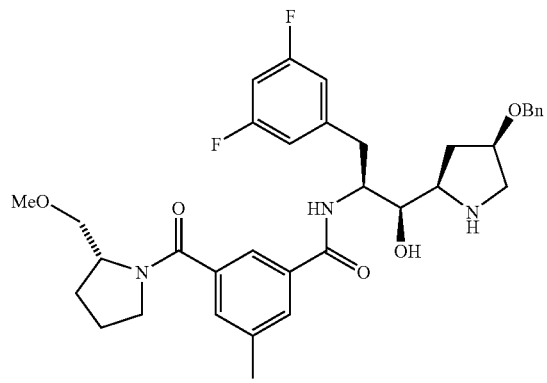

Using a procedure similar to Example 3, and the acid of Preparation 3 and the appropriate cyclic amine, the title compound was prepared. LCMS (Conditions A): $t_R$=3.63 min, m/e 622 (M+H)$^+$.

Example 4

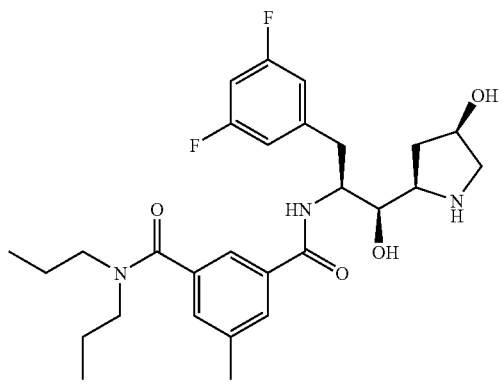

Pd(OH)$_2$/C (25 mg, 20% wt, 60% moisture) was added to a solution of Example 3 (15.2 mg, 23 µmol) in MeOH (3 ml), and the reaction was stirred for 6 h at 23° C. under 1 atm of H$_2$. After removal of the catalyst by filtration, the filtrate was acidified with 1 M HCl/MeOH and subsequently concentrated under reduced pressure to give the title compound (12.9 mg, 23 µmol, 100%). $^1$H NMR (400 MHz, CD$_3$OD) δ=8.41 (m, 1H), 7.54 (s, 1H), 7.34 (s, 1H), 7.26 (s, 1H), 6.84 (m, 2H), 6.66 (m, 1H), 4.47 (m, 1H), 4.16 (m, 1H), 4.02 (m, 1H), 3.78 (m, 1H), 3.43 (m, 2H), 3.39 (m, 1H), 3.16 (m, 1H), 3.11 (m, 2H), 2.83 (m, 1H), 2.36 (m, 1H; s, 3H), 2.05 (m, 1H), 1.67 (m, 2H), 1.45 (m, 2H), 1.24 (s, 1H), 0.96 (m, 3H), 0.67 (m, 3H); LCMS (Conditions A): $t_R$=4.17 min, m/e 518 (M+H)$^+$.

Example 5

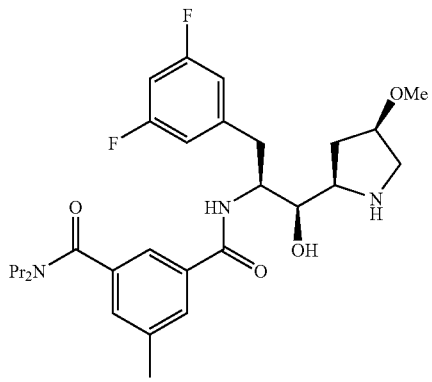

Step 1

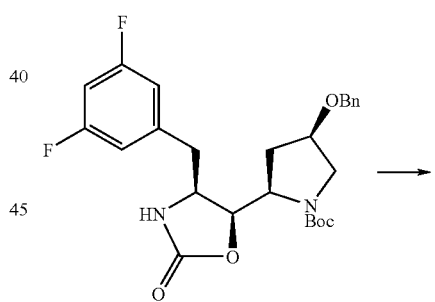

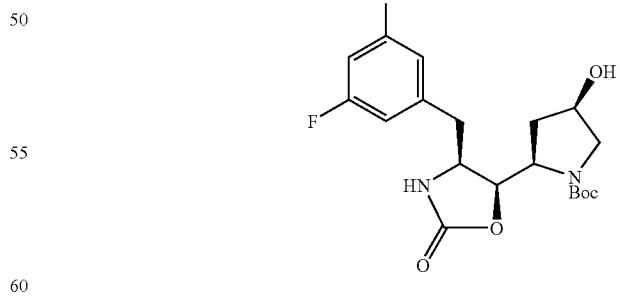

The product of Example 3, Step 1 (520 mg, 1.06 mmol) was stirred with 20% Pd(OH)$_2$/carbon (250 mg) in MeOH (5 ml) under a 50 psi atmosphere of H$_2$ at RT until TLC indicated the completion of the reaction. After filtering the reaction mixture over celite, the filtrate was concentrated to give the product in quantitative yield.

Step 2

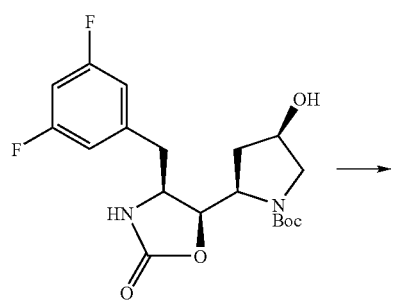

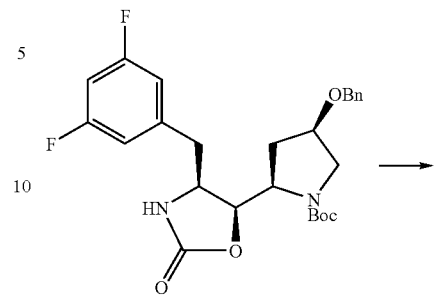

AgOTf (391 mg, 1.50 mmol) and 2,5-di-tert-butylpyridine (0.39 ml, 1.76 mmol) were added to a solution of the product from step 1 (216 mg, 0.54 mmol) in $CH_2Cl_2$ (2 ml) at RT. $CH_3I$ (0.11 ml, 1.75 mmol) was added and the reaction mixture was stirred at 0° C. for 1 h, then diluted with $CH_2Cl_2$ and filtered through celite. The filtrate was washed (1×0.5 M HCl, 1× $NaHCO_3$, 1× brine), dried ($MgSO_4$), concentrated and subjected to silica gel chromatography to give the desired product.

Acetic anhydride (2 ml) was added to a solution of DMAP (122 mg, 1.00 mmol), $Et_3N$ (3 ml) and the product from Example 3, Step 1 (1.02 g, 2.08 mmol) in toluene (5 ml) at 0° C. The reaction mixture was allowed to warm to RT, stirred for 8 h, then concentrated. The residue was subjected to silica gel chromatography to give the N-acetyl oxazolidinone in 63% yield. The resulting material (698 mg, 1.31 mmol) was debenzylated with 20% $Pd(OH)_2$/carbon (127 mg) in EtOAc under a 50 psi atmosphere of $H_2$ at RT over 18 h. After filtering the reaction mixture over celite, the filtrate was concentrated to give the desired product in 70% yield.

Step 3

The product of Step 2 was subjected to essentially the sequence of reactions described in Example 2, Steps 5 and 6 to give the product. LCMS (conditions A) $t_R$=3.55 min; 532 $(M+H)^+$

Step 2

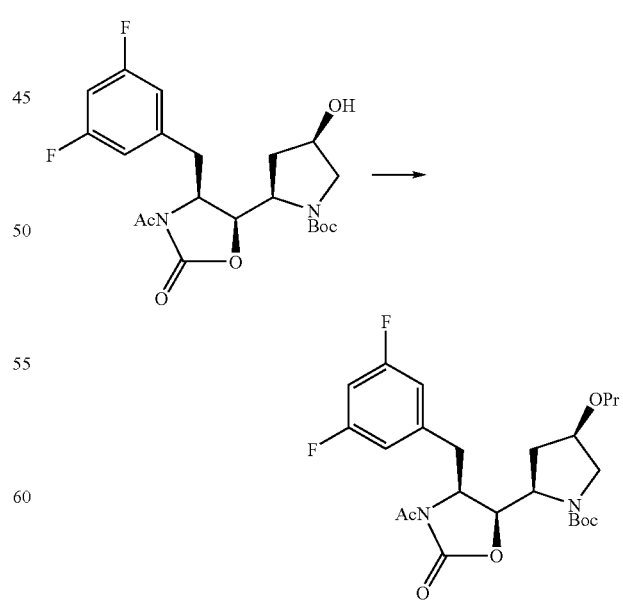

Example 6

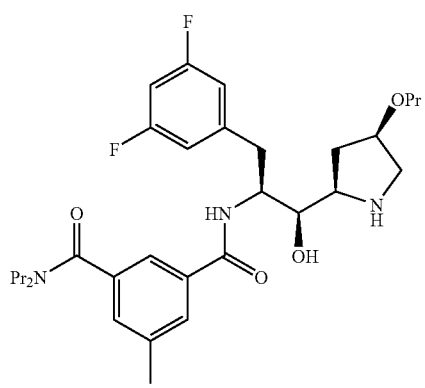

CsOH—$H_2O$ (114 mg, (167 mmol) was added to a suspension of the product of Step 1 (100 mg, 0.22 mmol), TBAI (83 mg, 0.22 mmol) and 4 Å molecular sieves (200 mg) in DMF (2 ml) at RT. After a few minutes, allyl bromide (0.06 ml, 0.68 mmol) was added, and the reaction stirred for 20 h. After filtration, the reaction was partitioned between EtOAc and water, and the organic layer was washed (2× brine), dried (MgSO₄) and concentrated. The residue was subjected to reverse-phase HPLC (Conditions C) to give the allyl ether, which was hydrogenated with 20% Pd(OH)₂/carbon (50 mg) in MeOH (5 ml) under a 50 psi atmosphere of H₂ at RT. After filtration, the desired product was obtained, which was directly taken into the next step.

Step 3

The product of Step 2 was subjected to essentially the sequence of reactions described in Example 2, Steps 5 and 6 to give the product. LCMS (conditions A) $t_R$ 3.15 min; m/e 560 (M+H)⁺

Example 7

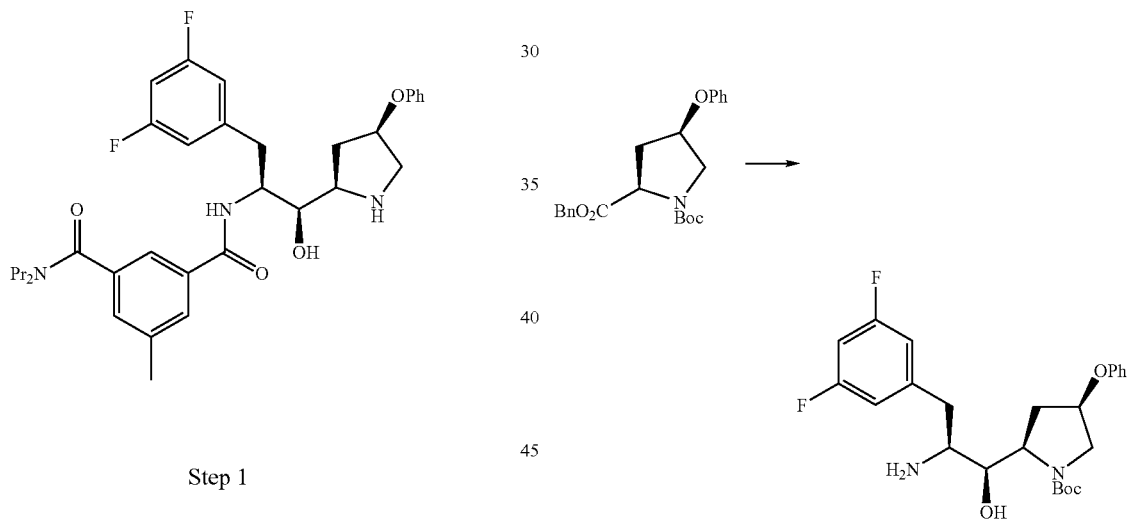

Step 1

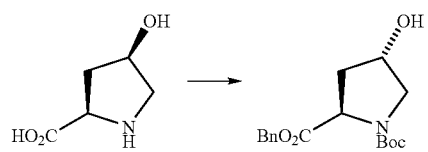

Cis-4-hydroxy-D-proline was converted into (4R)-(1-tert-butoxycarbonyl)-4-hydroxy-D-proline benzyl ester based on the procedure reported for the synthesis of (4S)-1-tert-butoxycarbonyl)-4-hydroxy-L-proline benzyl ester from cis-4-hydroxy-L-proline (Webb et al. *J. Org. Chem.* (1991), 56, 3009-3016). Mitsunobu inversion to give (4S)-1-(tert-butoxycarbonyl)-4-hydroxy-D-proline benzyl ester was adapted from the reported procedure (Lowe et al. *J. Chem. Soc. Perkin Trans.* 1 (1997), 539-546) for the synthesis of (4S)-1-tert-butoxycarbonyl)-4-hydroxy-D-proline methyl ester from (4R)-1-(tert-butoxycarbonyl)-4-hydroxy-D-proline methyl ester.

Step 2

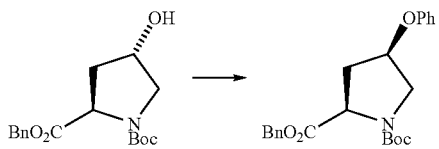

(4S)-1-(tert-butoxycarbonyl)-4-hydroxy-D-proline benzyl ester was converted into (4R)-1-(tert-butoxycarbonyl)-4-phenoxy-D-proline benzyl ester based on the reported protocol (Bellier et al. *J. Med. Chem.* (1997), 40, 3947-3956) for the corresponding methyl ester.

Step 3

The product of Step 2 was converted into the amino alcohol product by essentially the same procedure used in Example 2, Steps 1 through 5, except that the product of Step 2 was used in place of methyl N-Boc-D-1,2,3,4-tetrahydroquinoline-3-carboxylate.

Step 4

The product of Step 3 was subjected to essentially the sequence of reactions described in Example 2, Step 6 to give the product. LCMS (conditions A) $t_R$=4.04 min; m/e 594 (M+H)⁺.

The examples below were prepared by reaction of the appropriate acid and amine starting materials in analogy to Example 2, Step 6.

| Example | Acid | Amine | Structure | LCMS data m/e (Conditions A) |
|---|---|---|---|---|
| 7A | Prep. 6 | | 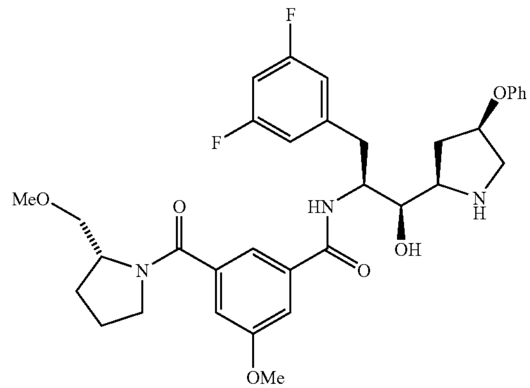 | 3.14 min; 624 (M + H)+ |
| 7B | Prep. 4 | | 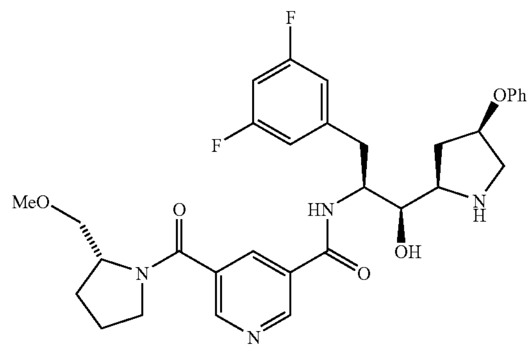 | 3.05 min; 595 (M + H)+ |
| 7C | Prep. 5 | | 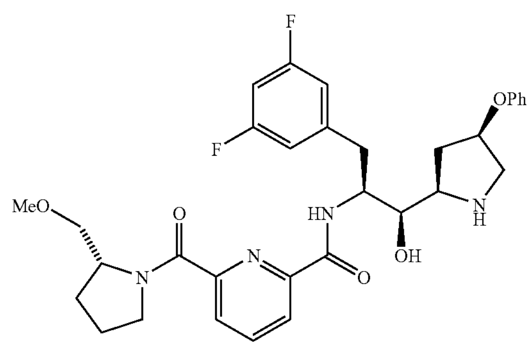 | 3.24 min; 595 (M + H)+ |
| 7D | Prep. 3 | | 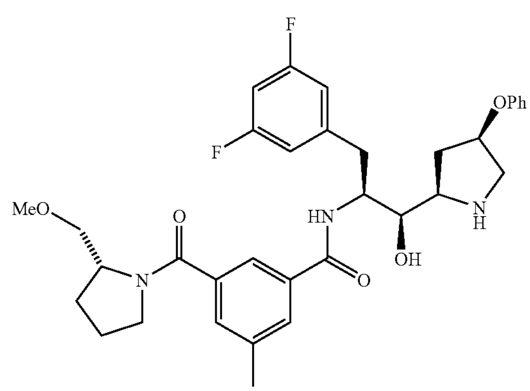 | 3.58 min; 608 (M + H)+ |

Example 8

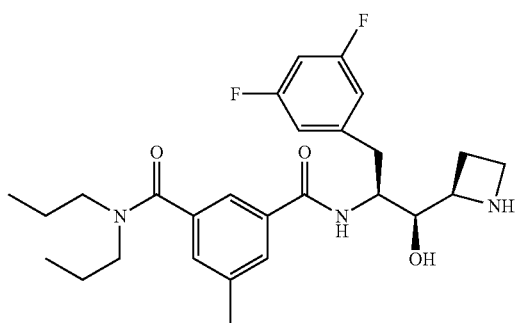

Step 1

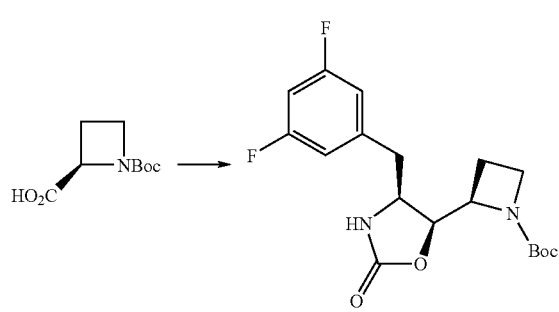

N-Boc-(R)-azetidine-2-carboxylic acid was converted to the product in analogy to the procedure of Example 2, Step 1 to Step 4. LCMS (Conditions A): $t_R$=4.4 min; $(M+H)^+$=369.

Step 2

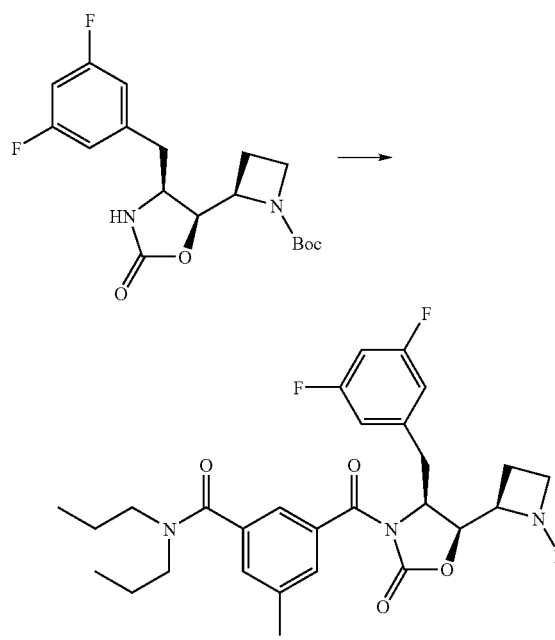

To a solution of Preparation 1 (438 mg, 1.66 mmol) in THF (8.5 ml) was added oxalyl chloride (0.43 ml, 633 mg, 4.99 mmol) followed by one drop of DMF. After 2 h at RT, the turbid mixture was concentrated to give the acid chloride as a yellow solid. This material used without further purification.

To a 0° C. solution of the product of Step 1 in $CH_2Cl_2$ was added $Et_3N$ (0.26 ml, 195 mg, 1.93 mmol) followed by the above acid chloride (543 mg, 1.93 mmol). DMAP (29 mg, 0.24 mmol) was then added and the reaction mixture was allowed to warm to RT. After 18 h, the reaction mixture was diluted with saturated aq. $NaHCO_3$, then water and $CH_2Cl_2$. The phases were separated, and the aqueous layer was extracted with $CH_2Cl_2$ (3×). The combined organic portions were washed with 1 N HCl, dried ($MgSO_4$), filtered, and concentrated. The residue was purified by column chromatography (silica, 0→100% EtOAc/hexanes) to give the product (321 mg, 0.523 mmol, 54%) as well as re-isolated starting material (150 mg, 42%).

Step 3

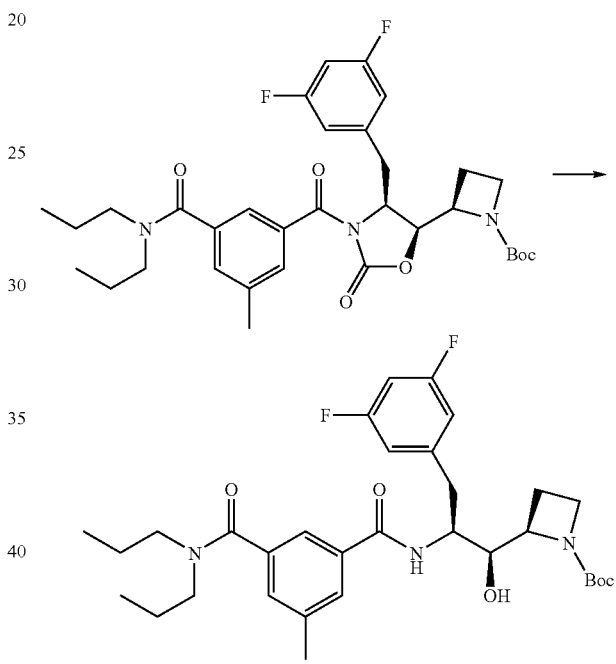

To a solution of the product of Step 2 (160 mg, 0.261 mmol) in MeOH (4 ml) was added $NaN_3$ (51 mg, 0.78 mmol). The mixture was warmed to 40° C. After 24 h, the reaction was cooled to RT and diluted with water and EtOAc. The phases were separated, and the aqueous portion was extracted with EtOAc (3×). The combined organic fractions were dried ($MgSO_4$), filtered, and concentrated. The crude residue was subjected to column chromatography (silica, 0→50%)/0 EtOAc/hexanes).

To a solution of the resultant residue (55 mg) in THF/EtOH (1/1, 0.8 ml) was added 10% aq. NaOH (0.8 ml). The resulting mixture was stirred at RT for 18 h. At that time, the reaction mixture was concentrated until cloudy, then diluted with EtOAc and 1 N HCl. The phases were separated, and the aqueous portion was extracted with EtOAc (3×). The combined organic fractions were dried ($MgSO_4$), filtered, and concentrated. This crude residue was combined with that of a second run, and the mixture was purified by HPLC (Conditions D) to give the product (48 mg total mass, 57% average yield for the two runs). LCMS (Conditions A): $t_R$=4.9 min; $(M+H)^+$=588.

Step 4

To a solution of the product of Step 3 (41 mg, 0.070 mmol) in CH$_2$Cl$_2$ (2 ml) was added 4 N HCl in dioxane (1 ml). After 1.5 h at RT, the mixture was concentrated to dryness. The crude residue was purified by PTLC (1000 μm silica, 10% 7 N NH$_3$/MeOH in CH$_2$Cl$_2$) to give the title compound (10 mg, 0.021 mmol, 29%). LCMS (Conditions A): t$_R$=4.1 min; (M+H)$^+$=488; $^1$H NMR (CDCl$_3$, 300 MHz) δ 7.49 (s, 1H), 7.38 (s, 1H), 7.18 (s, 1H), 6.91 (br s 1H), 6.83 (m, 2H), 6.60 (apparent tt, J=9.0, 2.4 Hz, 1H), 4.22 (m, 1H), 4.10 (m, 1H), 3.57 (m, 2H), 3.36 (m, 3H), 3.09 (m, 3H), 2.97 (dd, J=14.1, 9.0 Hz, 1H), 2.55 (m, 1H), 2.33 (s, 3H), 2.14 (m, 1H), 1.67 (apparent quartet, J=7.2 Hz, 2H), 1.48 (apparent quartet, J=6.9 Hz, 2H), 0.96 (t, J=7.8 Hz, 3H), 0.70 (t, J=6.9 Hz, 3H).

Example 9 about 1 h, then poured into cold water. The mixture was extracted with CH$_2$Cl$_2$ (3×100 ml), dried (Na$_2$SO$_4$), filtered and concentrated. The residue was subjected to flash chromatography on silica gel (1:3 EtOAc/hexanes) to afford Isomer 1 as a white solid (378 mg, 20%) (R$_f$=0.176, EtOAc/hexanes=1/3) and Isomer 2 as a white solid (320 mg, 17%) (R$_f$=0.225, EtOAc/hexanes=1/3). Isomer 1: $^1$H NMR (CDCl$_3$, 400 MHz) δ 8.51 (m, 1H), 7.65 (m, 1H), 7.30 (m, 1H), 7.21 (m, 1H), 6.52 (m, 3H), 5.12 (m, 1H), 5.02 (s, br, 1H), 4.93 (s, 1H), 4.15 (m, 1H), 2.65 (m, 1H), 2.41 (m, 1H), 1.35 (s, 9H). LCMS (Conditions B): t$_R$=2.35 min, (M+H)$^+$=365.

Isomer 2: $^1$H NMR (CDCl$_3$, 400 MHz) δ 8.45 (m, 1H), 7.62 (m, 1H), 7.24 (m, 1H), 7.16 (m, 1H), 6.83 (m, 2H), 6.82 (m, 1H), 4.81 (m, 1H), 4.63 (s, 1H), 4.17 (m, 1H), 2.98 (m, 2H), 1.17 (s, 9H); LCMS (Conditions A): t$_R$=3.78 min, (M+H)$^+$=365.

Step 2

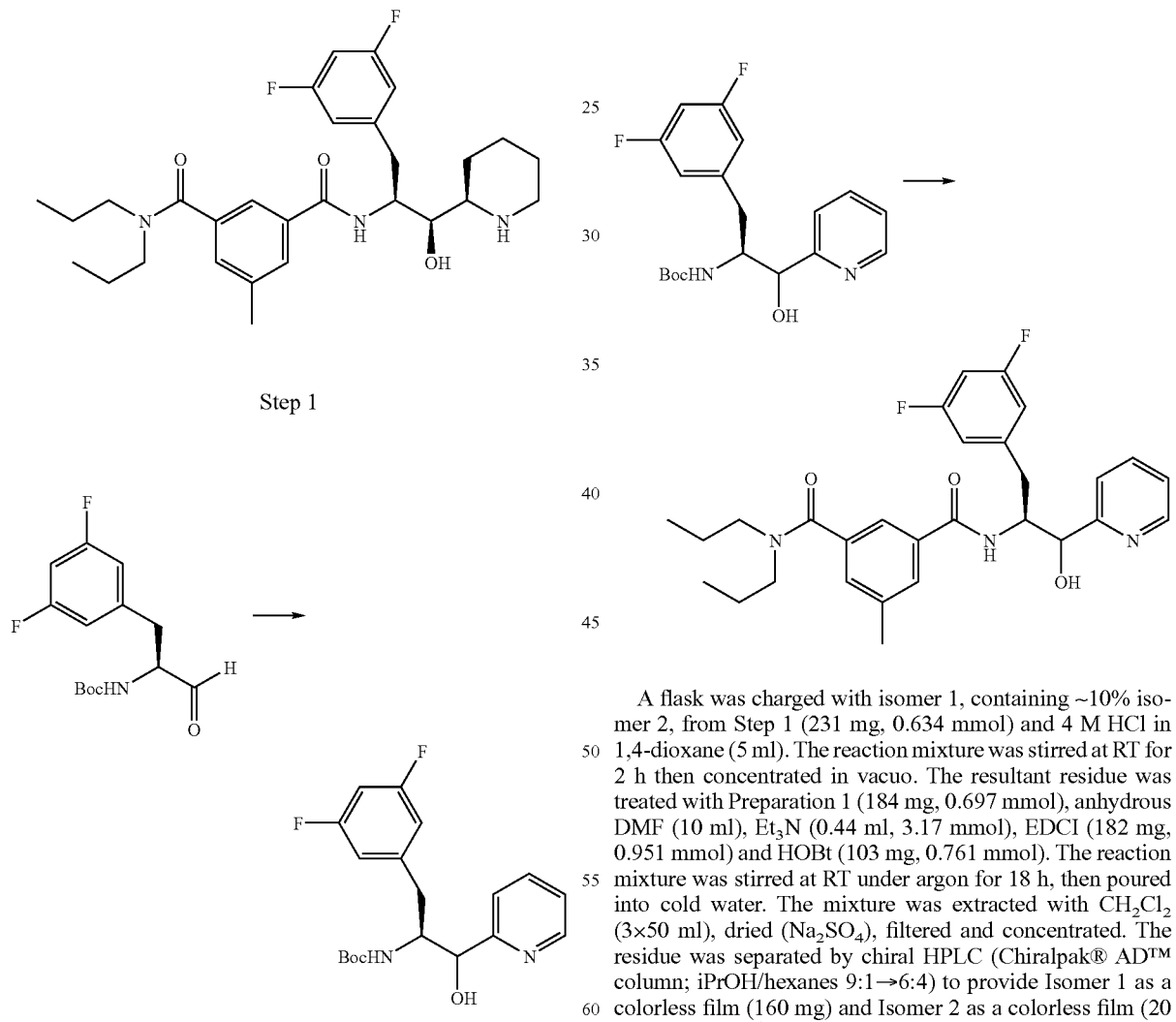

Step 1

To a solution of 2-bromopyridine (2.91 g, 18.4 mmol) in anhydrous Et$_2$O (100 ml) at −78° C. was slowly added n-BuLi (2.5 M/hexane, 6.3 ml, 15.8 mmol). After the addition was complete, Preparation 9 (1.50 g, 5.26 mmol) in anhydrous Et$_2$O (20 ml) was added slowly at −78° C. The reaction mixture was then allowed to warm to 0° C. and stirred for A flask was charged with isomer 1, containing ~10% isomer 2, from Step 1 (231 mg, 0.634 mmol) and 4 M HCl in 1,4-dioxane (5 ml). The reaction mixture was stirred at RT for 2 h then concentrated in vacuo. The resultant residue was treated with Preparation 1 (184 mg, 0.697 mmol), anhydrous DMF (10 ml), Et$_3$N (0.44 ml, 3.17 mmol), EDCI (182 mg, 0.951 mmol) and HOBt (103 mg, 0.761 mmol). The reaction mixture was stirred at RT under argon for 18 h, then poured into cold water. The mixture was extracted with CH$_2$Cl$_2$ (3×50 ml), dried (Na$_2$SO$_4$), filtered and concentrated. The residue was separated by chiral HPLC (Chiralpak® AD™ column; iPrOH/hexanes 9:1→6:4) to provide Isomer 1 as a colorless film (160 mg) and Isomer 2 as a colorless film (20 mg). Isomer 1: $^1$H NMR (CDCl$_3$, 400 MHz) δ 8.50 (m, 1H), 7.63 (m, 1H), 7.42 (m, 2H), 7.35 (s, 1H), 7.21 (m, 2H), 6.63 (m, 2H), 6.48 (m, 1H), 5.38 (s, br, 1H), 4.97 (m, 1H), 4.71 (m, 1H), 3.36 (m, 2H), 3.03 (m, 2H), 2.85 (m, 1H), 2.51 (m, 1H), 2.26 (s, 3H), 1.62 (m, 2H), 1.42 (m, 2H), 0.92 (m, 3H), 0.64 (m, 3H). LCMS (Conditions A): t$_R$=4.32 min, (M+H)$^+$=510. Isomer 2: $^1$H NMR (CDCl$_3$, 400 MHz) δ 8.40 (m, 1H), 7.61

(m, 1H), 7.29 (m, 2H), 7.15 (m, 3H), 6.90 (m, 2H), 6.63 (m, 1H), 6.43 (m, 1H), 4.75 (s, 1H), 4.65 (m, 1H), 3.40 (m, 2H), 3.10 (m, 2H), 3.02 (m, 2H), 2.30 (s, 3H), 1.62 (m, 2H), 1.42 (m, 2H), 0.92 (m, 3H), 0.65 (m, 3H). LCMS (Conditions A): $t_R$=4.39 min, (M+H)$^+$=510.

Step 3

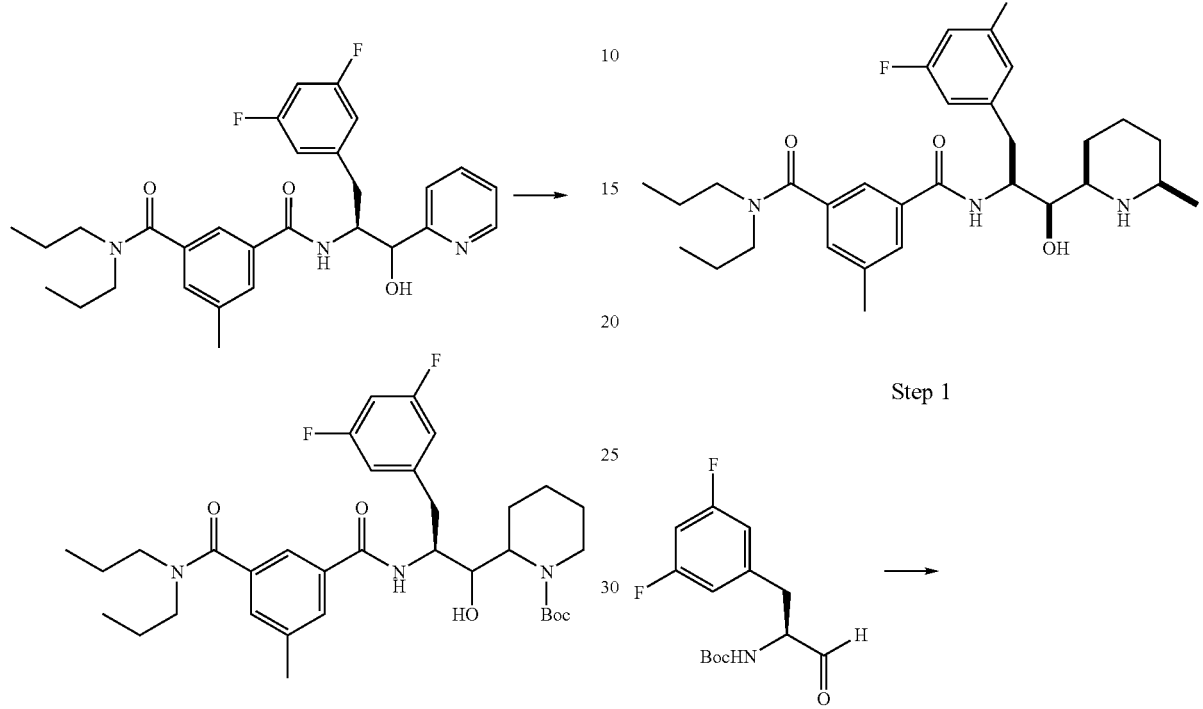

A Parr bottle charged with the product of Step 2, isomer 1 (34.4 mg, 67.5 µmol), AcOH (5 ml) and PtO$_2$ (30 mg) was shaken under H$_2$ (50 psi) for 3 h at RT, then filtered and concentrated. The resultant residue was dissolved in anhydrous CH$_2$Cl$_2$ (5 ml), to which Et$_3$N (19 µl, 0.135 mmol) and (Boc)$_2$O (22 mg, 0.101 mmol) were added. The reaction mixture was stirred at RT for 2 h, then poured into cold water. The mixture was extracted with CH$_2$Cl$_2$ (3×25 ml), dried (Na$_2$SO$_4$), filtered and concentrated. The residue was purified by chiral HPLC (Chiralpak® AD™ column; iPrOH/Hexane, 2%→30%) to yield Isomer 1 (18 mg, 44%) as a clear film and Isomer 2 (2 mg, 5%) as clear film. Isomer 1: $^1$H NMR (CDCl$_3$, 400 MHz) δ 7.50 (s, 1H), 7.35 (s, 1H), 7.17 (s, 1H), 7.12 (s, br, 1H), 6.71 (m, 2H), 6.52 (m, 1H), 4.21 (m, 3H), 4.01 (m, 1H), 3.38 (m, 2H), 3.09 (m, 3H), 2.83 (m, 2H), 2.29 (s, 3H), 2.05 (m, 1H), 1.70-1.30 (m, 19H), 0.92 (m, 3H), 0.65 (m, 3H). MS (M+H)$^+$=616. Isomer 2: $^1$H NMR (CDCl$_3$, 400 MHz) δ 7.43 (s, 1H), 7.32 (s, 1H), 7.21 (s, 1H), 6.76 (m, 2H), 6.57 (m, 2H), 4.46 (m, 1H), 4.26 (m, 1H), 4.12 (m, 1H), 3.91 (m, 1H), 3.39 (m, 2H), 3.06 (m, 2H), 2.90 (m, 3H), 2.33 (s, 3H), 1.80-1.40 (m, 19H), 0.92 (m, 3H), 0.66 (m, 3H). MS (M+H)$^+$=616.

Step 4

A solution of the product of Step 3, Isomer 1 (13.5 mg, 22 mmol) in 20% TFA/CH$_2$Cl$_2$ (2 ml) was stirred at RT for 1.5 h and concentrated in vacuo. The residue was purified by reverse phase HPLC (Conditions D) to give the product (11 mg, 89%). $^1$H NMR (CD$_3$OD, 400 MHz) δ 7.51 (s, 1H), 7.33 (s, 1H), 7.28 (s, 1H), 6.82 (m, 2H), 6.71 (m, 1H), 4.21 (m, 1H), 3.85 (m, 1H), 3.42 (m, 2H), 3.31 (m, 2H), 3.15 (m, 3H), 2.99 (m, 1H), 2.79 (m, 1H), 2.08 (m, 1H), 1.90-1.30 (m, 9H), 0.95 (m, 3H), 0.66 (m, 3H). LCMS (Conditions A): $t_R$=4.34 min, (M+H)$^+$=516.

Example 10A

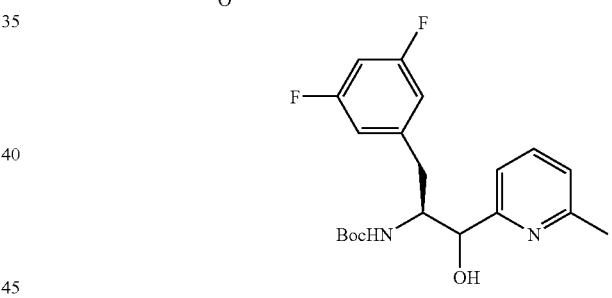

Step 1

To a stirred solution of Preparation 9 (2.20 g, 7.71 mmol) in anhydrous Et$_2$O (100 ml) at 0° C. was slowly added 6-methyl-2-pyridylmagnesium bromide (0.25 M, 92.5 ml, 23.1 mmol). The reaction mixture was stirred at 0° C. for 1.5 h, then poured into cold water. The mixture was extracted with CH$_2$Cl$_2$ (3×200 ml) and the combined organic layers were dried (Na$_2$SO$_4$), filtered and evaporated. The residue was purified by silica gel chromatography (hexanes→1:1 EtOAc/hexanes) to afford the product as a mixture of diastereomers. The mixture was separated by chiral HPLC (Chiralpak AD column; iPrOH/hexanes 1:9→3:20) and afforded Isomer 1 as a white solid (179 mg, 6%) and Isomer 2 as a clear film (190 mg, 7%). Isomer 1: $^1$H NMR (CDCl$_3$, 400 MHz) δ 7.50 (m, 1H), 7.05 (m, 2H), 6.51 (m, 3H), 5.18 (m, br, 2H), 4.85 (s, 1H), 4.12 (m, 1H), 2.59 (m, 1H), 2.52 (s, 3H), 2.38 (m, 1H), 1.34 (s, 9H). LCMS (Conditions A): $t_R$=3.93 min, m/e 379. Isomer 2: $^1$H NMR (CDCl$_3$, 400 MHz) δ 7.50 (m, 1H), 6.99 (m, 2H), 6.86 (m, 2H), 6.60 (m, 1H), 5.37 (s, br, 1H), 4.80 (m, 1H), 4.60 (m, 1H), 4.14 (m, 1H), 2.97 (m, 2H), 2.48 (s, 3H), 1.16 (s, 9H). LCMS (Conditions A): $t_R$=3.89 min, (M+H)$^+$=379.

Step 2

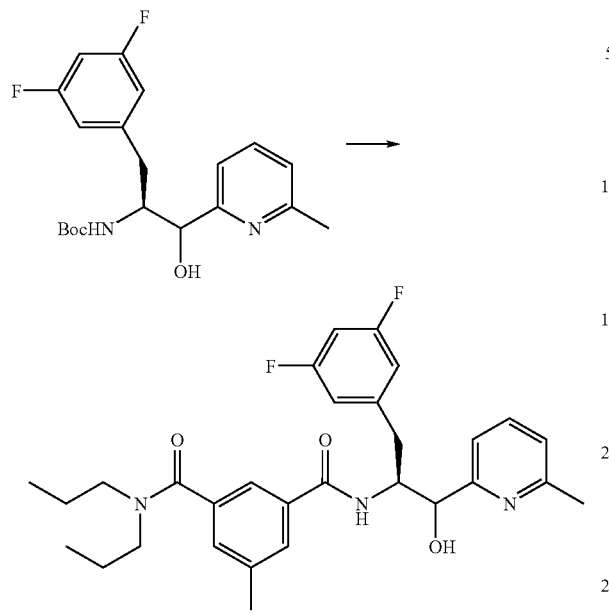

By essentially the procedure set forth in Example 9, Step 2, the above product was prepared from the product of Step 1, Isomer 1 in 61% yield. $^1$H NMR (CDCl$_3$, 400 MHz) δ 7.50 (m, 2H), 7.41 (s, 1H), 7.23 (m, 2H), 7.12 (m, 1H), 7.02 (m, 1H), 6.58 (m, 2H), 6.49 (m, 1H), 5.14 (s, br, 1H), 4.91 (m, 1H), 4.88 (m, 1H), 3.41 (m, 2H), 3.07 (m, 2H), 2.78 (m, 1H), 2.54 (s, 3H), 2.50 (m, 1H), 2.33 (s, 3H), 1.62 (m, 2H), 1.45 (m, 2H), 0.92 (m, 3H), 0.68 (m, 3H). LCMS (Conditions A): $t_R$=4.63 min, (M+H)$^+$=524.

Step 3

A flask charged with the product of Step 2 (41.5 mg, 79.2 μmol), AcOH (5 ml) and PtO$_2$ (5 mg) was stirred under 1 atm of H$_2$ for 18 h at RT. The reaction mixture was filtered and the filtrate was concentrated in vacuo. Purification of the residue by reverse phase HPLC (Conditions D) gave the product as a clear film (24.5 mg, 0.0426 mmol, 54%). LCMS (Conditions A): $t_R$=4.51 min; $t_R$=4.85 min (two major isomers), (M+H)$^+$ = 530 (both isomers).

Example 10B

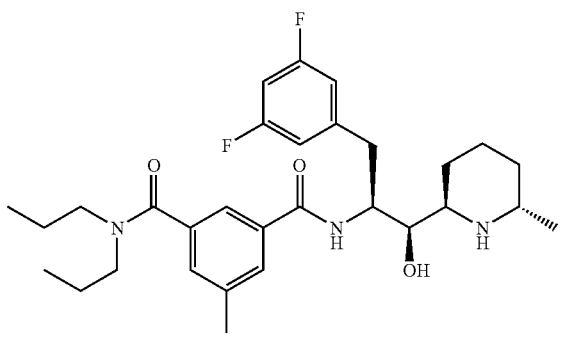

Step 1

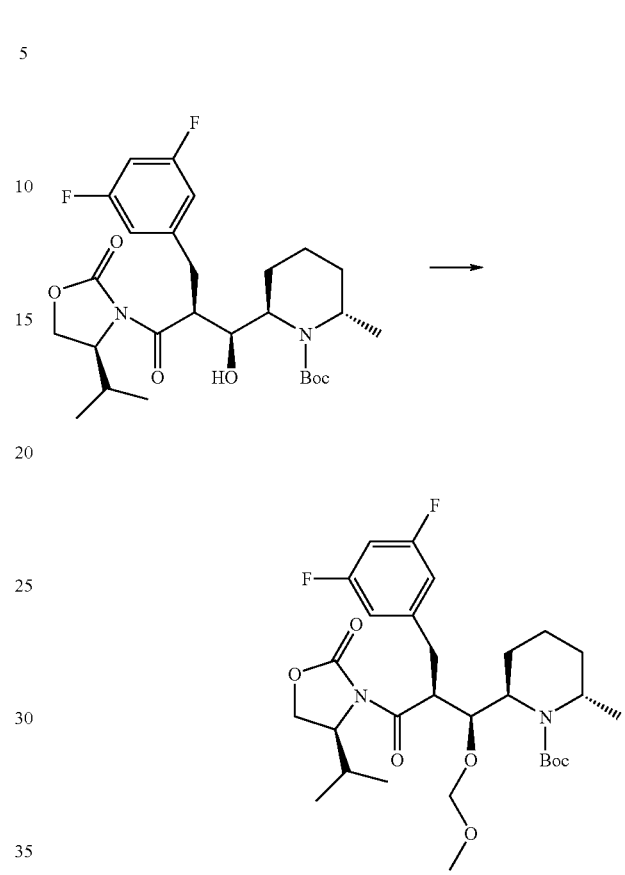

To a solution of the above starting material (418 mg, 0.797 mmol) [prepared from Example 3 and trans-2(R)-formyl-6 (S)-methyl-piperidine-1-carboxylic acid tert-butyl ester (prepared according to *J. Org. Chem.* (1999), 64, 1932) prepared in analogy to the procedure of Example 5, Step 1] in anhydrous CH$_2$Cl$_2$ (20 ml) was added iPr$_2$NEt (0.42 ml, 2.39 mmol) and methoxymethyl chloride (0.09 ml, 1.2 mmol). The reaction mixture was stirred at RT for 26 h and NaI (179 mg, 1.19 mmol) was then added. The reaction mixture was stirred at RT for another 16 h and then heated at reflux for 9 h. To the reaction solution was then added additional iPr$_2$NEt (0.50 ml) and methoxymethyl chloride (0.1 ml). The reaction mixture was refluxed for 2.5 days, cooled to RT, then poured into cold water and extracted with CH$_2$Cl$_2$ (3×). The combined organic layers were dried (Na$_2$SO$_4$), filtered and concentrated. PTLC of the residue (EtOAc/Hexane 1:1) gave the product (310 mg, 68%) as a clear film. $^1$H NMR (CDCl$_3$, 400 MHz) δ 6.78 (m, 2H), 6.50 (m, 1H), 4.63 (m, 2H), 4.32 (m, 2H), 4.14 (m, 2H), 4.02 (m, 2H), 3.65 (m, 1H), 3.62 (s, 3H), 3.19 (m, 1H), 3.05 (m, 1H), 2.04 (m, 1H), 1.80-1.50 (m, 6H), 1.43 (s, 9H), 1.27 (d, J=7.2 Hz, 3H), 0.74 (d, J=7.2 Hz, 3H), 0.41 (d, J=6.8 Hz, 3H). LCMS m/e 569 (M+H)$^+$, $t_R$=6.13 min. (condition A).

Step 2

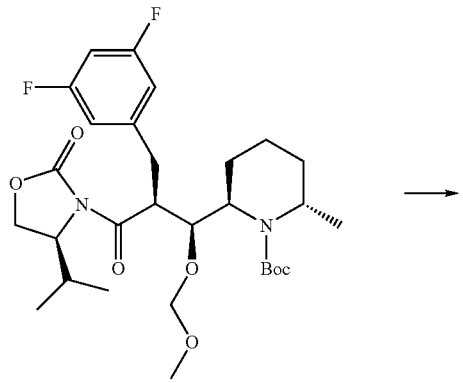

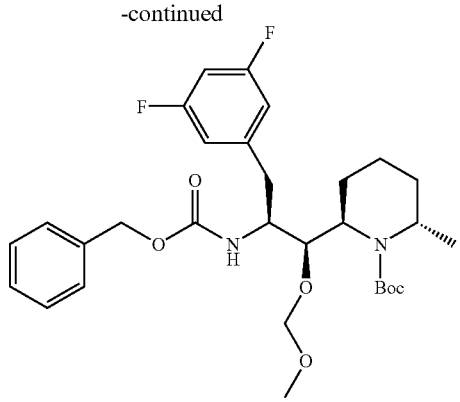

By essentially the procedure set forth in Example 5, Step 4, the product was synthesized from the product of Step 2 in 43% yield. ¹H NMR (CDCl$_3$, 400 MHz) δ 7.37-7.00 (m, 6H), 6.69 (m, 2H), 6.55 (m, 1H), 5.89 (m, 1H), 5.00 (m, 1H), 4.86 (m, 1H), 4.74 (m, 1H), 4.57 (m, 1H), 4.08 (m, 1H), 4.00-3.67 (m, 3H), 3.42 (s, 3H), 3.02 (m, 1H), 2.45 (m, 1H), 1.85-1.20 (m, 17H). MS m/e 563 (M+H)$^+$ Step 4

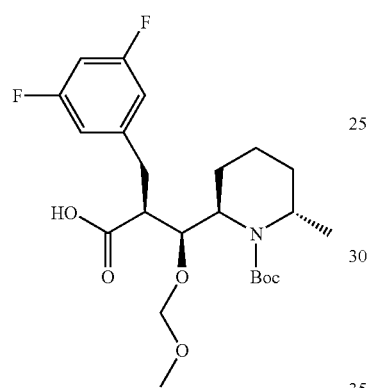

By essentially the procedure set forth in Example 5, Step 2, the product was synthesized from the product of Step 1 in 96% yield. ¹H NMR (CDCl$_3$, 400 MHz) δ 6.78 (m, 2H), 6.55 (m, 1H), 4.61 (m, 2H), 4.40 (m, 1H), 3.79 (m, 2H), 3.33 (s, 3H), 2.98-2.78 (m, 3H), 2.01 (s, br., 1H), 1.81-1.58 (m, 5H), 1.42 (s, 9H), 1.26 (d, J=6.8 Hz, 3H). LCMS m/e 458 (M+H)$^+$, t$_R$=3.50 min. (condition B).

Step 3

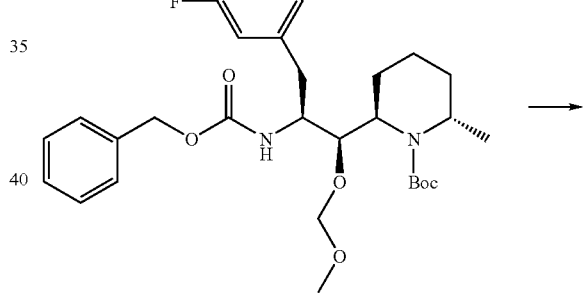

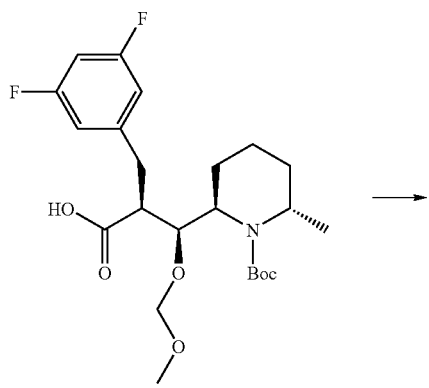

To a solution of the product of Step 3 (33.3 mg, 0.0592 mmol) in MeOH (5 ml) was added 10% Pd/C (20 mg). The solution was stirred under a balloon of H$_2$ at RT for 2 h. The solution was then filtered through celite and concentrated in vacuo to afford the product (25.3 mg, 100% yield) as a clear film. ¹H NMR (CDCl$_3$, 400 MHz) δ 6.75 (m, 2H), 6.59 (m, 1H), 4.75 (m, 1H), 4.64 (m, 1H), 3.97-3.80 (m, 2H), 3.71 (m, 1H), 3.39 (s, 3H), 3.06 (m, 2H), 2.41 (m, 1H), 1.85-1.50 (m, 6H), 1.44 (s, 9H), 1.25 (d, J=6.8 Hz, 3H). MS m/e 429 (M+H)+.

Step 5

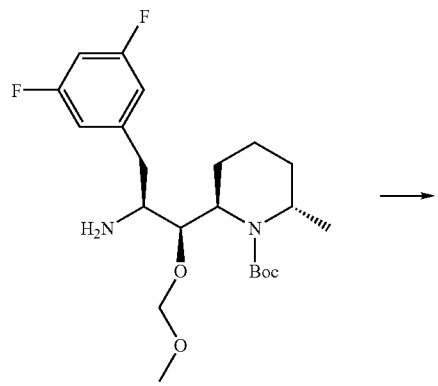

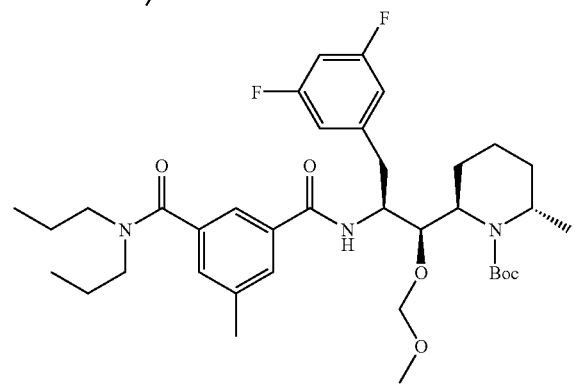

By essentially the procedure of Example 7, Step 2, the product was synthesized from the product of Step 4 and Preparation 1 in 55% yield. ¹H NMR (CDCl₃, 400 MHz) δ 7.82 (m, 1H), 7.63 (s, 1H), 7.51 (s, 1H), 7.24 (s, 1H), 6.75 (m, 2H), 6.57 (m, 1H), 4.82 (d, J=6.8 Hz, 1H), 4.71 (m, 1H), 4.62 (d, J=6.8 Hz, 1H), 4.03 (m, 1H), 3.87 (m, 2H), 3.47 (s, 3H), 3.45 (m, 2H), 3.12 (m, 3H), 2.65 (m 1H), 2.38 (s, 3H), 1.90-1.40 (m, 20H), 1.38 (d, J=6.8 Hz, 3H), 0.98 (m, 3H), 0.70 (m, 3H). LCMS m/e 674 (M+H)+, $t_R$=4.03 min. (condition B).

Step 6

To a solution of the product of Step 5 (16.0 mg, 23.7 μmol) in CH₂Cl₂ (1.2 ml) was added one drop of water and TFA (0.8 ml). The reaction mixture was stirred at RT for 21 h and then concentrated in vacuo. The residue was purified by reverse phase HPLC (C18 column, H₂O (0.1% HCOOH)/CH₃CN (0.1% HCOOH)=5%-95%) to afford the formate salt of the product (10 mg, 75%) as a clear film. ¹H NMR (CD₃OD, 400 MHz) δ 7.50 (s, 1H), 7.33 (s, 1H), 7.28 (s, 1H), 6.81 (m, 2H), 6.69 (m, 1H), 4.21 (m, 1H), 3.86 (m, 1H), 3.68 (m, 1H), 3.42 (m, 2H), 3.31 (m, 2H), 3.11 (m, 2H), 2.80 (m, 1H), 2.37 (s, 3H), 2.02 (m, 1H), 1.90-1.40 (m, 9H), 1.28 (d, J=6.8 Hz, 3H), 0.95 (t, J=7.6 Hz, 3H), 0.66 (t, J=7.6 Hz, 3H). LCMS m/e 530 (M+H)+, $t_R$=4.39 min. (condition A).

Example 11

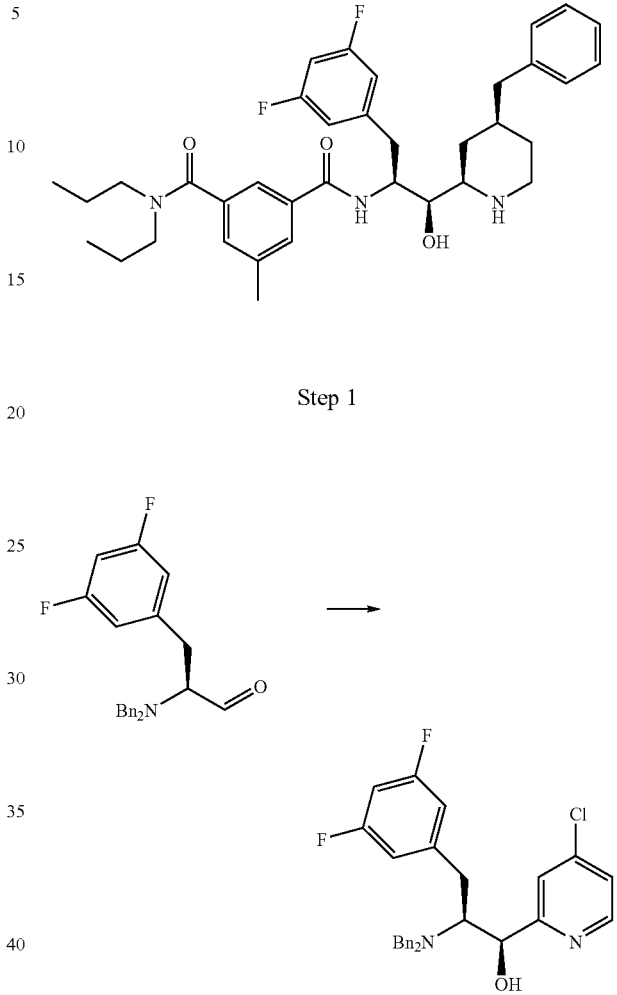

Step 1

A solution of N,N-dimethylaminoethanol (2.60 ml, 26.2 mmol) in anhydrous hexane (50 ml) was cooled to −5° C. with stirring, to which nBuLi (2.5 M/hexane, 21.0 ml, 52.3 mmol) was added slowly. After the addition, the reaction mixture was warmed to 0° C. and stirred for 0.5 h. The reaction mixture was then cooled to −78° C., and 4-chloropyridine (3.00 g, 26.2 mmol) in anhydrous hexane (10 ml) was added slowly. The reaction mixture was stirred at −78° C. for 1.5 h, then a solution of Preparation 10 (7.97 g, 21.8 mmol) in anhydrous THF (20 ml) was added dropwise. After the addition, the reaction was allowed to warm to 0° C. and stirred at 0° C. for an additional 0.5 h. The reaction mixture was then poured into cold H₂O and extracted with CH₂Cl₂ (3×). The combined organic layers were dried over Na₂SO₄. The concentrated residue was purified by chromatography over silica gel (EtOAc/Hexane, 0%→425%) to afford the product as a light brown oil (4.45 g, 43%). ¹H NMR (CDCl₃, 400 MHz) δ 8.31 (d, J=2.8 Hz, 1H), 7.40-7.05 (m, 11H), 6.87 (d, J=1.6 Hz, 1H), 6.55 (m, 1H), 6.35 (m, 2H), 5.15 (s, br, 1H), 4.51 (s, br, 1H), 3.95 (d, J=14.0 Hz, 2H), 3.68 (d, J=14 Hz, 1H), 3.14 (m, 1H), 2.93 (m, 1H), 2.45 (m, 1H). MS (M+H)+=479 (M+H)+.

Step 2

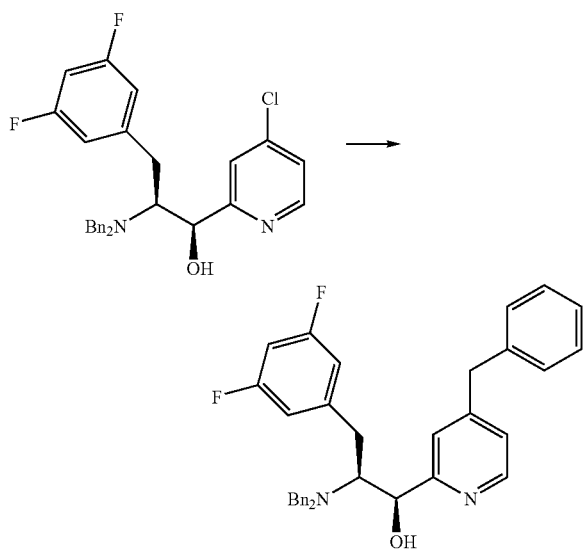

To a pressure tube was added the product of Step 1 (222 mg, 0.463 mmol) and 0.50 M BnZnCl/THF (4.60 ml, 2.32 mmol). The reaction mixture was then purged with argon for ~2 min, then Pd(PPh$_3$)$_4$ (107 mg, 0.0926 mmol) was added. The reaction mixture was stirred at 110° C. for 3 h, then allowed to cool to RT. The reaction mixture was poured into saturated NR$_4$Cl and extracted with CH$_2$Cl$_2$ (3×). The combined organic layers were dried over Na$_2$SO$_4$. The concentrated residue was separated by PTLC (EtOAc/Hexane, 1:2) to give the product (176 mg, 71%) as a light yellow film. MS (M+H)$^+$=535.

Step 3

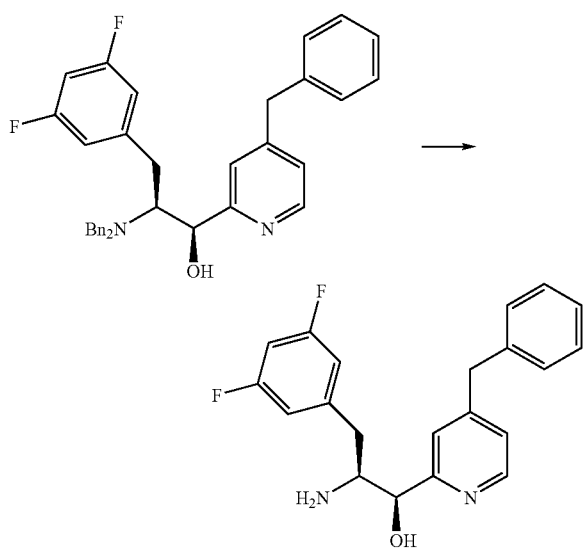

The product of Step 2 (176 mg, 0.330 mmol), 20% Pd(OH)$_2$/C (50 mg) and ethanol (5 mL) was stirred under 1 atm of H$_2$ for 24 h at RT, then filtered through celite. The concentrated residue was purified by reverse phase HPLC (Conditions D) to provide the formate salt of the product (41.7 mg, 32%) as a clear film. $^1$H NMR (CD$_3$OD, 400 MHz) δ 8.37 (d, J=5.2 Hz, 1H), 7.42 (s, 1H), 7.30 (m, 2H), 7.20 (m, 3H), 7.15 (m, 1H), 6.75 (m, 1H), 6.87 (m, 2H), 4.93 (m, 1H), 4.01 (m, 3H), 2.79 (m, 2H). MS (M+H)$^+$=355.

Step 4

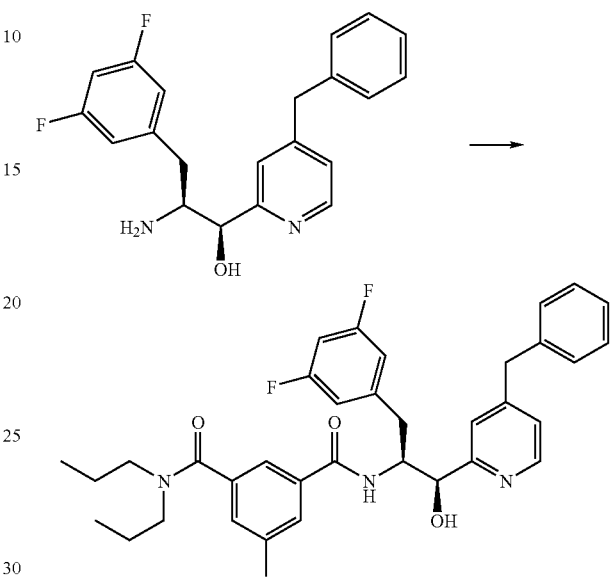

The product of Step 3 (15.1 mg, 42.6 μmol), Preparation 1 (12.0 mg, 46.8 μmol), EDCI (16.0 mg, 85.2 μmol) and HOBt (9.0 mg, 63.9 μmol) were dissolved in anhydrous DMF (1.0 ml), and Et$_3$N (60 μl, 426 μmol) was added. After stirring for 22 h at RT, the reaction was poured into water. The aqueous layer was extracted with CH$_2$Cl$_2$ (3×). The combined organic layers were dried over Na$_2$SO$_4$. The concentrated residue was purified by PTLC (1:20 CH$_3$OH/CH$_2$Cl$_2$) to give the product (14.6 mg, 57%). $^1$H NMR (CDCl$_3$, 400 MHz) δ 8.40 (d, j=4.4 Hz, 1H), 7.50 (s, 1H), 7.41 (s, 1H), 7.32-7.18 (m, 4H), 7.14 (s, 1H), 7.11 (m, 2H), 7.02 (m, 1H), 6.92 (d, J=8.8 Hz, 1H), 6.56-6.45 (m, 3H), 5.02 (d, J=5.2 Hz, 1H), 4.91 (m, 1H), 4.66 (m, 1H), 3.90 (s, 2H), 3.41 (m, br., 2H), 3.08 (m, br., 2H), 2.77 (m, 1H), 2.47 (m, 1H), 2.36 (s, 3H), 1.65 (m, br., 2H), 1.46 (m, br., 2H), 0.94 (m, br., 3H), 0.69 (m, br., 3H). MS (M+H)$^+$=600.

Step 5

To the product of Step 4 (10.0 mg, 16.7 μmol), THF (2.7 ml) and acetic acid (0.3 ml) was added PtO$_2$ (20 mg). The suspension was stirred under 1 atm H$_2$ for 4 h, then filtered through celite. The concentrated residue was purified by PTLC (7M NH$_3$/CH$_3$OH:CH$_2$Cl$_2$=1:10) and then HPLC (Conditions C) to afford the product as a formate salt (3.1 mg, 31%). $^1$H NMR (CD$_3$OD, 400 MHz) δ 7.45 (s, 1H), 7.28 (m, 2H), 7.21 (m, 2H), 7.12 (m, 3H), 6.81 (m, 2H), 6.70 (m, 1H), 4.18 (m, 1H), 3.86 (m, 1H), 3.45 (m, 2H), 3.31 (m, 2H), 3.25 (m, 3H), 2.92 (m, 1H), 2.78 (m, 1H), 2.68 (m, 1H), 2.50 (m, 1H), 2.38 (s, 3H), 2.11 (d, J=14 Hz, 1H), 1.84-1.62 (m, 4H), 1.54-1.22 (m, 4H), 0.96 (t, J=7.6 Hz, 3H), 0.66 (t, J=7.6 Hz, 3H). LCMS (Conditions A): t$_R$=4.74 min, (M+H)$^+$=606.

By analogy to the procedure of Example 11, the following examples were prepared.

| Example | Structure | LCMS (Conditions A) |
|---|---|---|
| 11A | 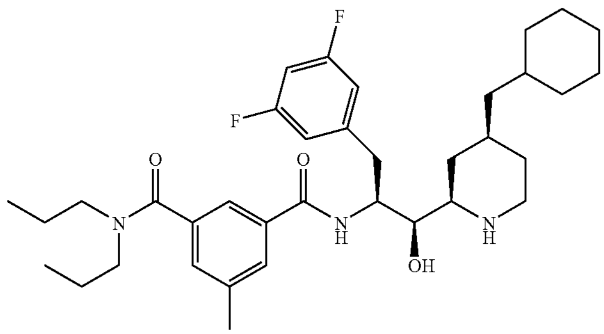 | m/e 612 (M + H)⁺ (t_R = 5.94 min) |
| 11B | 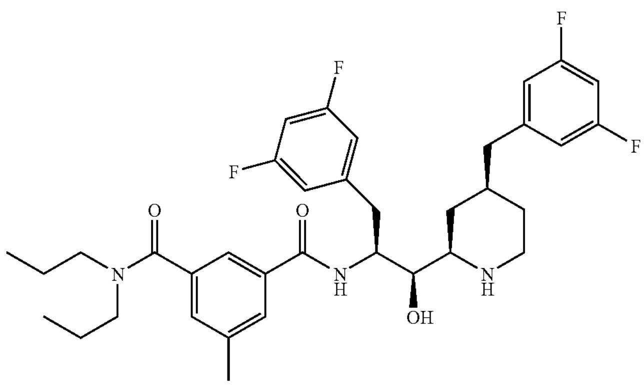 | m/e 642 (M + H)⁺ (t_R = 5.40 min) |
| 11C | 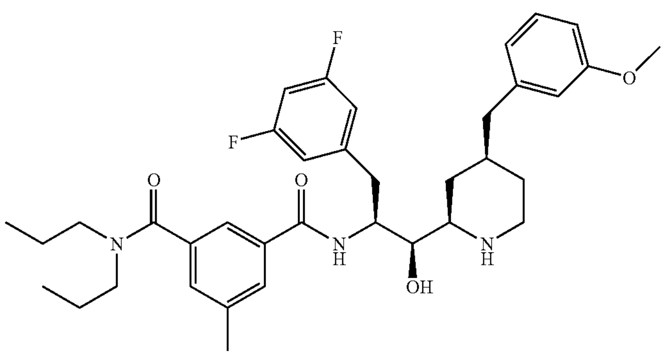 | m/e 636 (M + H)⁺ (t_R = 4.80 min) |
| 11D | 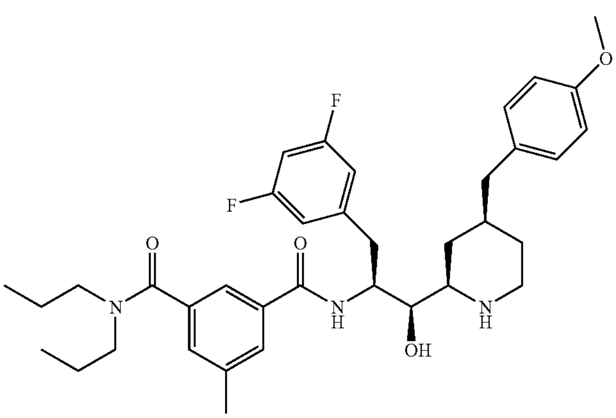 | m/e 636 (M + H)⁺ (t_R = 4.11 min) |

| Example | Structure | LCMS (Conditions A) |
|---------|-----------|---------------------|
| 11E | 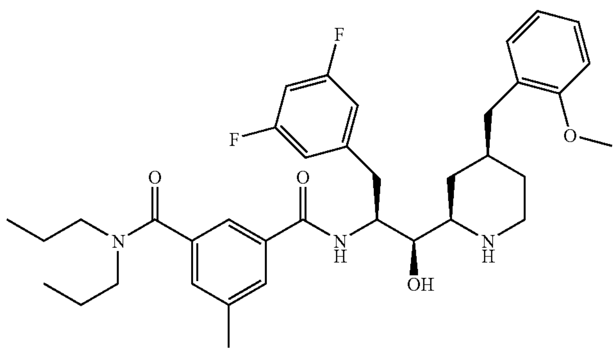 | m/e 636 (M + H)⁺ (t_R = 4.06 min) |
| 11F | 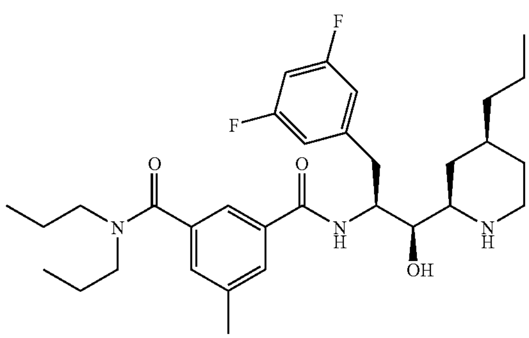 | m/e 558 (M + H)⁺ (t_R = 4.75 min) |
| 11G | 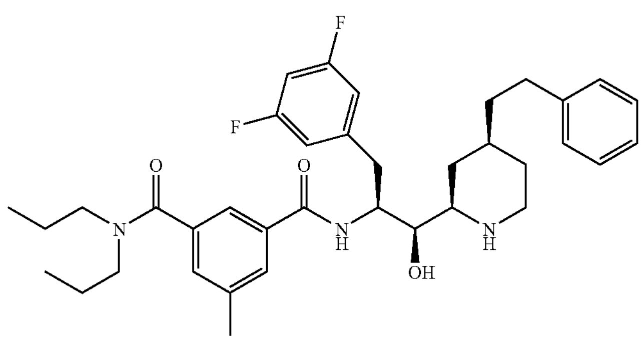 | m/e 620 (M + H)⁺ (t_R = 4.23 min) |
| 11H | 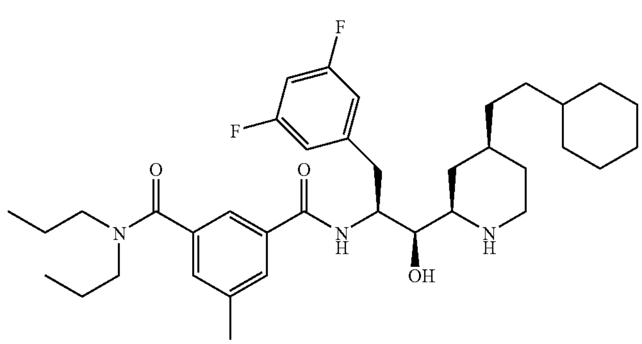 | m/e 626 (M + H)⁺ (t_R = 5.54 min) |

Example 12

Step 1

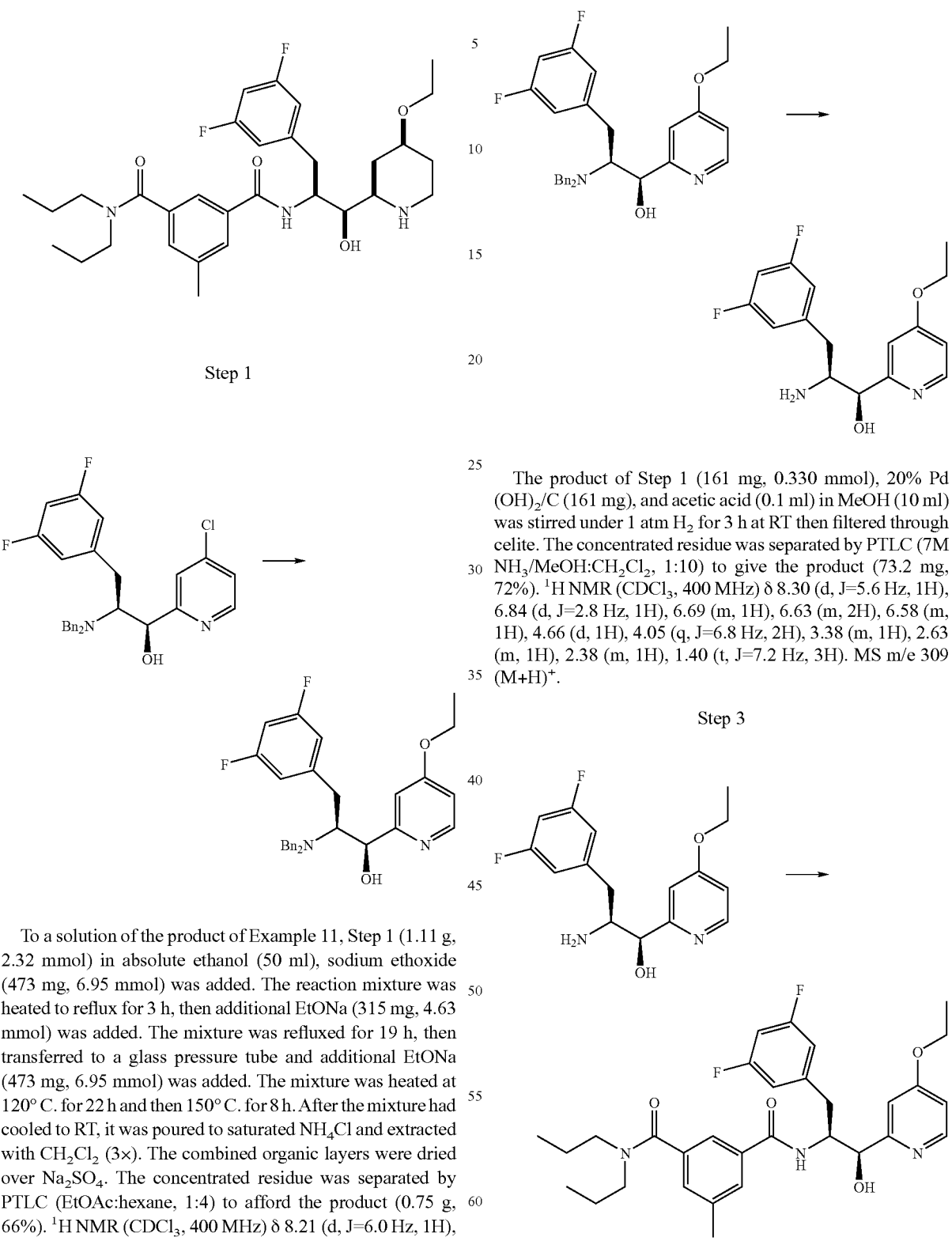

To a solution of the product of Example 11, Step 1 (1.11 g, 2.32 mmol) in absolute ethanol (50 ml), sodium ethoxide (473 mg, 6.95 mmol) was added. The reaction mixture was heated to reflux for 3 h, then additional EtONa (315 mg, 4.63 mmol) was added. The mixture was refluxed for 19 h, then transferred to a glass pressure tube and additional EtONa (473 mg, 6.95 mmol) was added. The mixture was heated at 120° C. for 22 h and then 150° C. for 8 h. After the mixture had cooled to RT, it was poured to saturated $NH_4Cl$ and extracted with $CH_2Cl_2$ (3×). The combined organic layers were dried over $Na_2SO_4$. The concentrated residue was separated by PTLC (EtOAc:hexane, 1:4) to afford the product (0.75 g, 66%). $^1$H NMR (CDCl$_3$, 400 MHz) δ 8.21 (d, J=6.0 Hz, 1H), 7.40-7.05 (m, 10H), 6.62 (m, 1H), 6.58 (m, 1H), 6.31 (m, 2H), 6.20 (d, J=2.0 Hz, 1H), 5.19 (s, 1H), 4.06 (d, J=14.4 Hz, 2H), 3.90 (m, 1H), 3.78 (m, 1H), 3.69 (d, J=14.4 Hz, 2H), 3.10 (m, 1H), 2.92 (m, 1H), 2.35 (m, 1H), 1.35 (t, J=6.8, 3H). MS m/e 489 (M+H)$^+$.

Step 2

The product of Step 1 (161 mg, 0.330 mmol), 20% Pd(OH)$_2$/C (161 mg), and acetic acid (0.1 ml) in MeOH (10 ml) was stirred under 1 atm H$_2$ for 3 h at RT then filtered through celite. The concentrated residue was separated by PTLC (7M NH$_3$/MeOH:CH$_2$Cl$_2$, 1:10) to give the product (73.2 mg, 72%). $^1$H NMR (CDCl$_3$, 400 MHz) δ 8.30 (d, J=5.6 Hz, 1H), 6.84 (d, J=2.8 Hz, 1H), 6.69 (m, 1H), 6.63 (m, 2H), 6.58 (m, 1H), 4.66 (d, 1H), 4.05 (q, J=6.8 Hz, 2H), 3.38 (m, 1H), 2.63 (m, 1H), 2.38 (m, 1H), 1.40 (t, J=7.2 Hz, 3H). MS m/e 309 (M+H)$^+$.

Step 3

The product was obtained from the product of Step 2 in analogy to the procedure of Example 11, Step 4, in 63% yield as a clear film. $^1$H NMR (CDCl$_3$, 400 MHz) δ 8.30 (d, J=5.6 Hz, 1H), 7.51 (s, 1H), 7.41 (s, 1H), 7.23 (s, 1H), 6.91 (m, 1H), 6.77 (s, 1H), 6.70 (m, 1H), 6.58 (m, 2H), 6.50 (m, 1H), 5.09 (d, 1H), 4.90 (m, 1H), 4.69 (m, 1H), 4.01 (q, 1H), 3.41 (m, br, 2H), 3.08 (m, br, 2H), 2.79 (m, 1H), 2.55 (m, 1H), 2.36 (s, 3H), 1.65 (m, br, 2H), 1.50 (m, br., 2H), 1.39 (t, J=7.2 Hz, 3H), 0.95 (m, br, 3H), 0.70 (m, br., 3H). MS m/e 554 (M+H)+.

Step 4

The product of Step 3 (14.3 mg, 0.0258 mmol), PtO$_2$ (14 mg) and acetic acid (2 ml) was stirred under 1 atm H$_2$ for 2 h, then filtered through celite. The concentrated residue was separated by PTLC (7M NH$_3$/CH$_3$OH:CH$_2$Cl$_2$, 1:10) and then HPLC (Conditions C) to afford the product as the formate salt (4.5 mg, 29%). $^1$H NMR (CD$_3$OD, 400 MHz) δ 7.56 (s, 1H), 7.32 (s, 1H), 7.28 (s, 1H), 6.75 (d, J=8.0 Hz, 2H), 6.70 (m, 1H), 4.23 (m, 1H), 3.89 (m, 1H), 3.60-3.20 (m, 10H), 3.10 (t, J=7.6 Hz, 2H), 3.04 (m, 1H), 2.78 (m, 1H), 2.52 (m, 1H), 2.37 (s, 3H), 2.10 (m, 1H), 1.70-1.35 (M, 7H), 1.14 (t, J=7.2 Hz, 3H), 0.95 (t, J=7.2 Hz, 3H), 0.66 (t, J=0.72 Hz, 3H). LCMS (Conditions A) t$_R$=3.58 min m/e 560 (M+H)+

Using the appropriate starting material and essentially the same procedure set forth in Example 12, the following examples were prepared.

| Example | Structure | LCMS (Conditions A) |
|---|---|---|
| 12A | 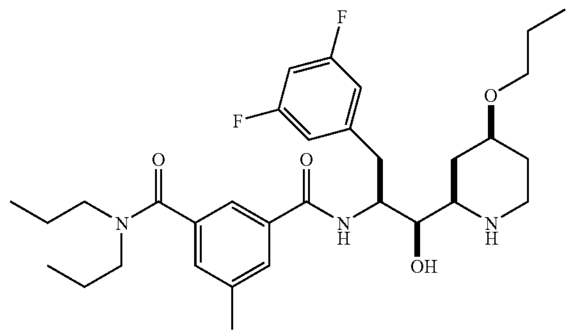 | m/e 574 (M + H)+ (t$_R$ = 3.59 min) |
| 12B | 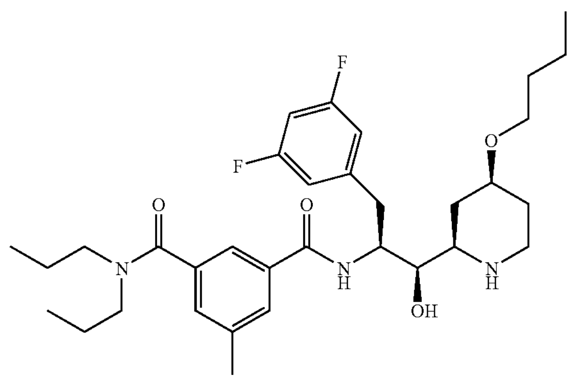 | m/e 588 (M + H)+ (t$_R$ = 3.71 min) |
| 12C | 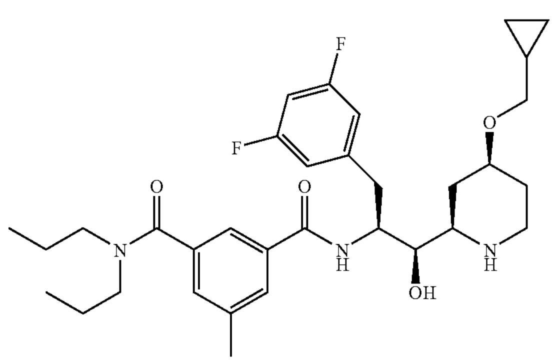 | m/e 586 (M + H)+ (t$_R$ = 3.66 min) |

-continued

| Example | Structure | LCMS (Conditions A) |
|---|---|---|
| 12D | 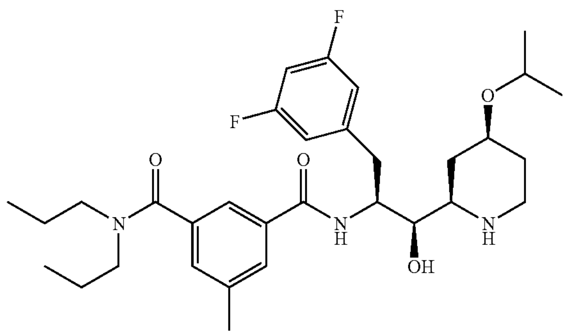 | m/e 574 (M + H)⁺ ($t_R$ = 3.83 min) |
| 12E | 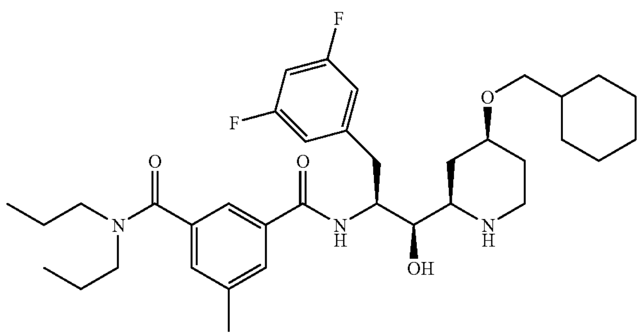 | m/e 628 (M + H)⁺ ($t_R$ = 4.45 min) |
| 12F | 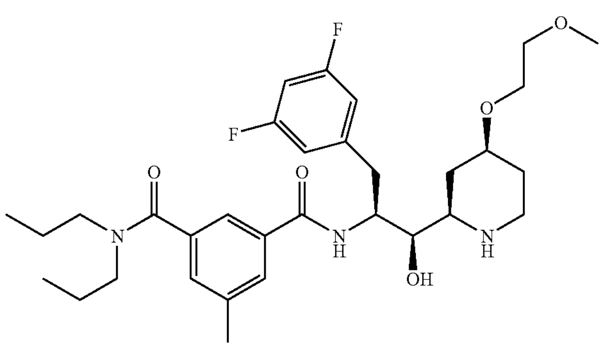 | m/e 590 (M + H)⁺ ($t_R$ = 2.97 min) |
| 12G | 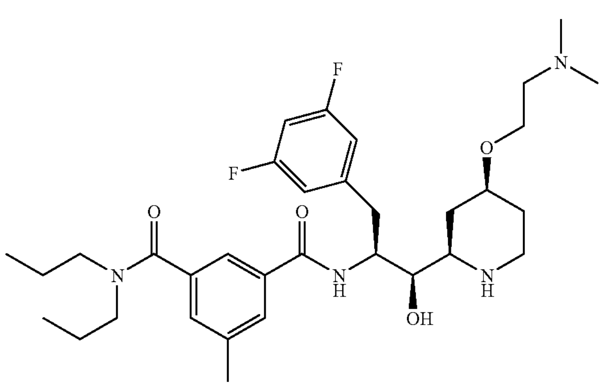 | m/e 603 (M + H)⁺ ($t_R$ = 3.07 min) |

-continued

| Example | Structure | LCMS (Conditions A) |
|---------|-----------|---------------------|
| 12H | 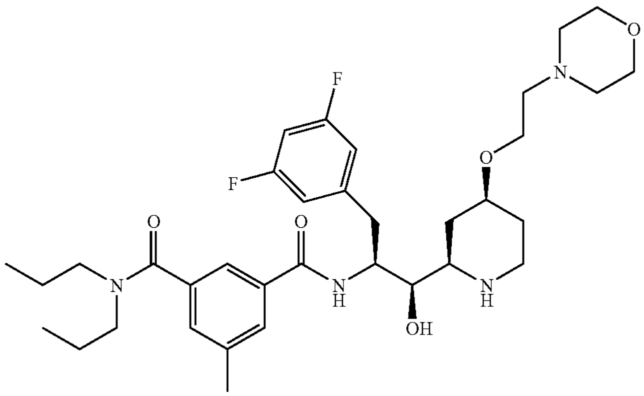 | m/e 645 (M + H)+ ($t_R$ = 2.84 min) |

By essentially the same procedure set forth in Example 12, except that Preparation 1 was replaced by Preparation 3 in Step 3, the following examples were prepared.

| Example | Structure | LCMS (Conditions A) |
|---------|-----------|---------------------|
| 12I | 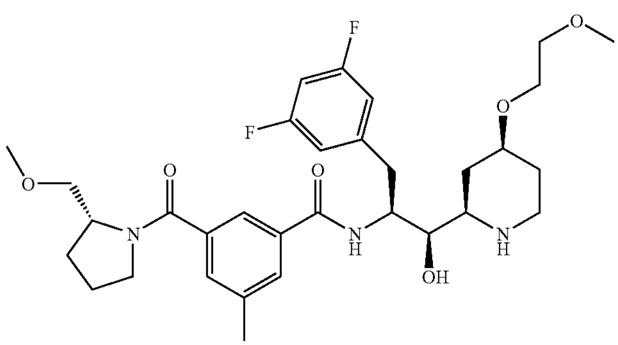 | m/e 604 (M + H)+ ($t_R$ = 2.89 min) |
| 12J | 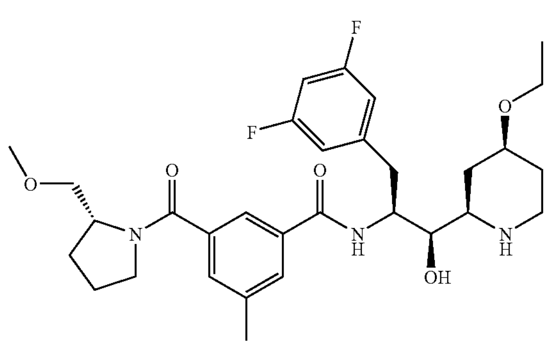 | m/e 604 (M + H)+ ($t_R$ = 2.83 min) |

Example 12K

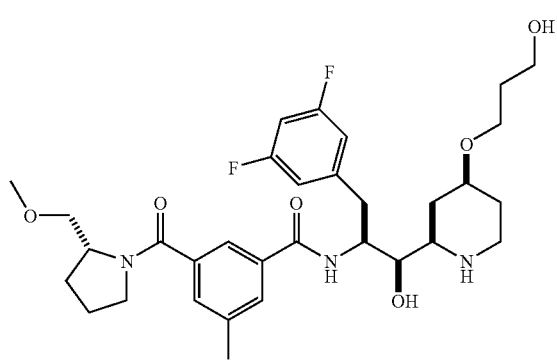

Step 1

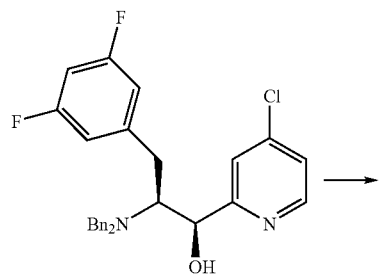

Crushed, vacuum dried KOH (582 mg, 10.4 mmol) in anhydrous DMSO (10 ml) was heated to 65° C. and stirred for 0.5 h, then 1,3-propanediol (0.75 ml, 10.4 mmol) and the product of Example 11, Step 1 (624 mg, 1.30 mmol) were added. The reaction mixture was stirred at 65° C. for 2 h, then allowed to cool to RT. The mixture was poured into cold water and extracted with $CH_2Cl_2$. The combined organic layers were dried over $Na_2SO_4$. The concentrated residue was purified by chromatography over silica gel (EtOAc/Hexane, 0%→50%) to give the product (70 mg, 10%) as a clear film. $^1H$ NMR ($CDCl_3$, 400 MHz) δ 8.21 (d, J=6.0 Hz, 1H), 7.30-7.00 (m, 10H), 6.61 (m, 1H), 6.55 (m, 1H), 6.31 (m, 2H), 6.23 (s, 1H), 5.15 (s, 1H), 4.03 (d, J=14 Hz, 2H), 3.97 (m, 1H), 3.85 (m, 1H), 3.81 (m, 2H), 3.67 (d, J=14 Hz, 2H), 3.10 (m, 1H), 2.92 (m, 1H), 2.35 (m, 1H), 1.97 (m, 2H). MS m/e 519 $(M+H)^+$.

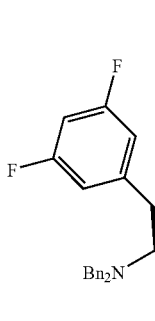

Step 2

The title compound was obtained from the product of Step 1 in analogy to the procedure of Example 12, Steps 2-4, substituting Preparation 1 for Preparation 3 in Step 3. $^1H$ NMR ($CD_3OD$, 400 MHz) δ 7.57 (s, 1H), 7.51 (s, 1H), 7.45 (s, 1H), 6.87 (m, 2H), 6.75 (m, 1H), 4.35 (m, 1H), 4.28 (m, 1H), 3.95 (m, 1H), 3.70-3.20 (m, 13H), 3.08 (m, 2H), 2.82 (m, 1H), 2.58 (m, 1H), 2.64 (s, 3H), 2.20-1.40 (m, 10H). LCMS (Conditions A) $t_R$=2.72 min; m/e 604 $(M+H)^+$

Example 12L

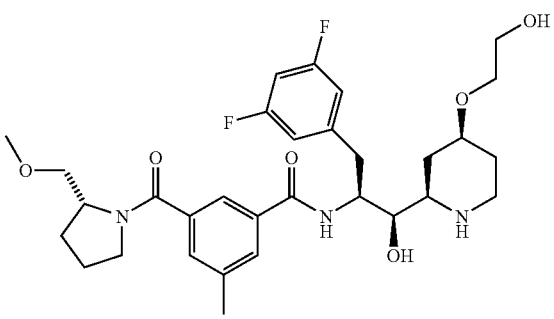

The title compound was prepared according to the procedure of Example 12K: LCMS (Conditions A) m/e 590 (M+H)+, $t_R$=2.86 min.

Example 13

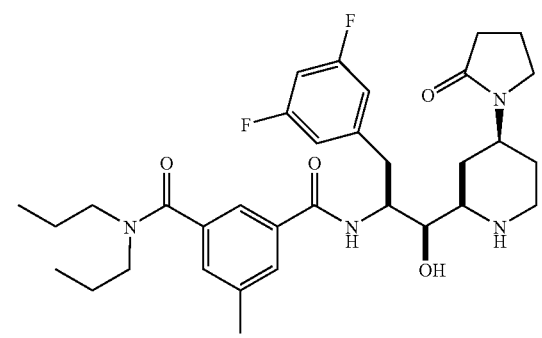

Step 1

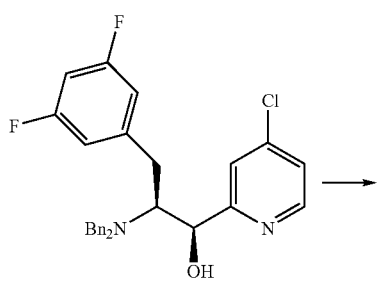

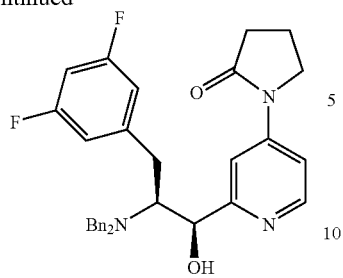

The product of Example 11, Step 1 (385 mg, 0.804 mmol), K$_2$CO$_3$ (333 mg, 2.41 mmol), pyrrolidin-2-one (137 mg, 1.61 mmol), CuI (15 mg, 0.0804 mmol) and trans-N,N'-dimethyl-cyclohexane-1,2-diamine (22 mg, 0.161 mmol) in anhydrous 1,4-dioxane (1.0 ml) was heated to 130° C. in a sealed tube. After 37 h, the reaction mixture was allowed to cool, poured into cold water and extracted with CH$_2$Cl$_2$ (3×). The combined organic layers were dried over Na$_2$SO$_4$. The concentrated residue was purified by PTLC (EtOAc:hexane, 1:1) to afford the product (45 mg, 11%) as a light brown film. $^1$H NMR (CDCl$_3$, 400 MHz) δ 8.35 (d, J=6.0 Hz, 1H), 7.69 (m, 1H), 7.25-7.08 (m, 10H), 6.87 (s, 1H), 6.53 (m, 1H), 6.30 (d, J=6.8 Hz, 2H), 5.22 (m, 1H), 4.95 (m, 1H), 4.03 (d, J=14 Hz, 2H), 3.66 (d, J=14.4 Hz, 2H), 3.61 (m, 1H), 3.50 (m, 1H), 3.10 (m, 1H), 2.91 (m, 1H), 2.61 (t, J=8.0 Hz, 2H), 2.31 (m, 1H), 2.15 (m, 2H). MS m/e 528 (M+H)$^+$.

Step 2

The product was obtained from the product of Step 1 in analogy to the procedure of Example 12, Steps 2-4. $^1$H NMR (CD$_3$OD, 400 MHz) δ 7.50 (s, 1H), 7.32 (s, 1H), 7.25 (s, 1H), 6.82 (m, 2H), 6.66 (m, 1H), 4.28 (m, 1H), 3.90 (m, 1H), 3.62 (m, 1H), 3.60-3.00 (m, 8H), 2.71 (m, 2H), 2.63 (m, 1H), 2.37 (s, 3H), 2.31 (m, 2H), 1.99 (m, 2H), 1.1.85 (m, 1H), 1.80-1.35 (m, 7H), 0.95 (m, 3H), 0.66 (m, 3H). LCMS (Conditions A) t$_R$=3.28 min; m/e 599 (M+H)$^+$.

Example 14

To a Parr pressure vessel was added the product of Example 11, Step 1 (711 mg, 1.48 mmol), Et$_3$N (0.25 ml, 1.86 mmol), PPh$_3$ (97 mg, 0.37 mmol) and MeOH (15 ml). The mixture was purged with N$_2$ for ~5 min, then PdCl$_2$(PPh$_3$)$_2$ (52 mg, 0.074 mmol) was added. The vessel was charged with carbon monoxide at 60 psi and the reaction mixture was stirred at 150° C. for 17 h. The mixture was allowed to cool and poured into water and the aqueous layer was extracted with CH$_2$Cl$_2$ (3×). The combined organic layers were dried over Na$_2$SO$_4$. The concentrated residue was purified by chromatography over silica gel (EtOAc/Hexane, 0%-30%) to afford the product MS m/e 503 (M+H)$^+$.

Step 2

The title compound was obtained from the product of Step 1 in analogy to the procedure of Example 12, Steps 2-4, substituting Preparation 1 for Preparation 3 in Step 3. LCMS (Conditions A) t$_R$=2.79 min; m/e 588 (M+H)$^+$.

Example 15

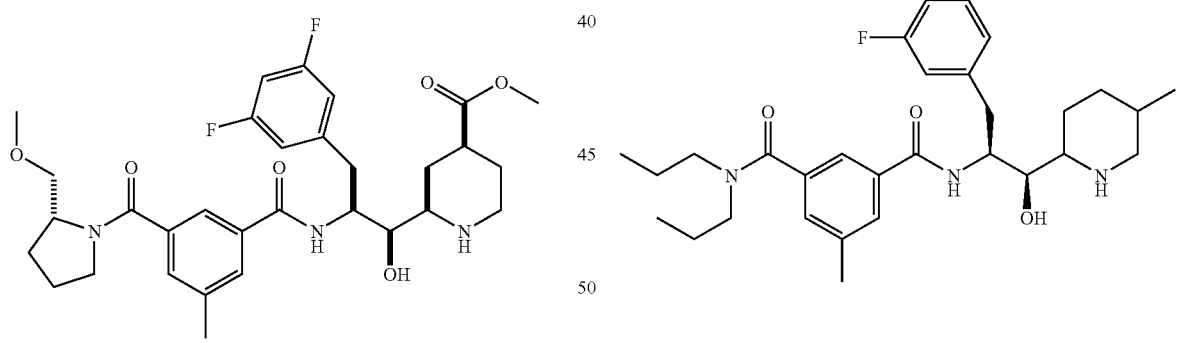

Step 1

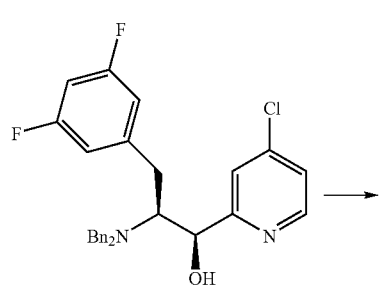

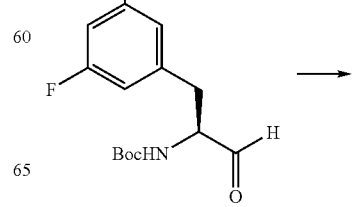

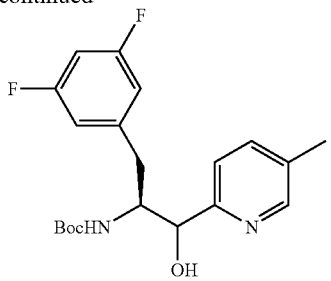

To solution of 2-bromo-5-methylpyridine (1.8 g, 11 mmol) in anhydrous toluene (50 ml) cooled to −78° C. was added nBuLi (1.6 M/hexane, 5.5 ml, 8.8 mmol). The reaction mixture was stirred at −78° C. for 30 min. Preparation 9 (1.0 g, 3.5 mmol) in anhydrous toluene (10 ml) was added at −78° C. The reaction mixture was stirred at −78° C. for 30 min and at RT for 1 h. The reaction was quenched with saturated NH$_4$Cl aqueous solution, extracted with EtOAc, dried (MgSO$_4$), filtered and concentrated. The residue was subjected to silica gel flash chromatography (5:95 EtOAc/CH$_2$Cl$_2$) to afford the product as a mixture of diastereoisomers (0.5 g, 38%).

Step 2

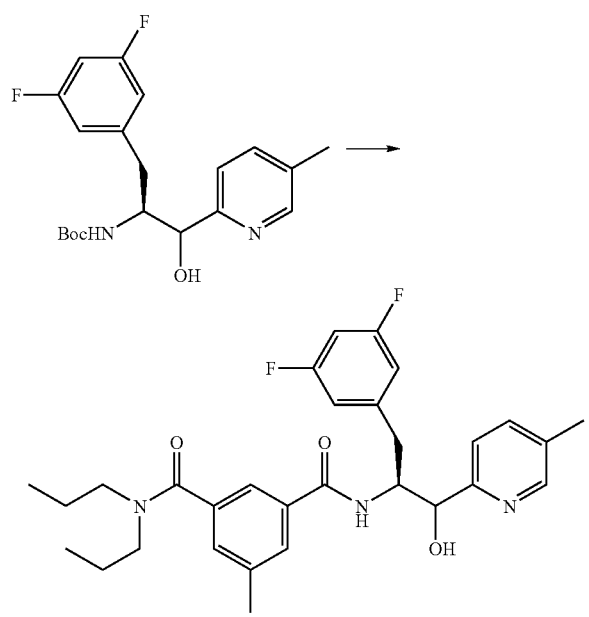

A flask was charged with product from Step 1 (0.5 g), TFA (6 ml) and CH$_2$Cl$_2$ (25 ml). The reaction mixture was stirred at RT for 2 h then concentrated in vacuo. The residue was dissolved in a solution [5:95 (2M NH$_3$ in MeOH)/CH$_2$Cl$_2$], washed with saturated NaHCO$_3$ solution, dried (MgSO$_4$), filtered and concentrated. The residue was subjected to flash chromatography [5:95 (2M NH$_3$ in MeOH)/CH$_2$Cl$_2$] to isolate the slower moving diastereoisomer as the intermediate product (100 mg, 0.265 mmol).

The intermediate product from above was treated with Preparation 1 (105 mg, 0.398 mmol), anhydrous DMF (10 ml) and EDC (101 mg, 0.530 mmol). The reaction mixture was stirred at RT for 4 h, then concentrated. The residue was dissolved in EtOAc, washed with water and brine, dried (MgSO$_4$), filtered and concentrated. The residue was subjected to silica gel flash chromatography (50:50 EtOAc/Hexane) to give the product (125 mg, 91%).

Step 3

A flask charged with the product of Step 2 (125 mg), AcOH (10 ml) and PtO$_2$ (35 mg) was stirred under H$_2$ (1 atmosphere) for 1.5 h, then filtered and concentrated. The residue was separated on PTLC [10:90 (2M NH$_3$ in MeOH)/CH$_2$Cl$_2$] to give the desired product as a white solid (15 mg). LCMS (Conditions A) $t_R$=3.71 min; m/e 530 (M+H)$^+$.

Example 16

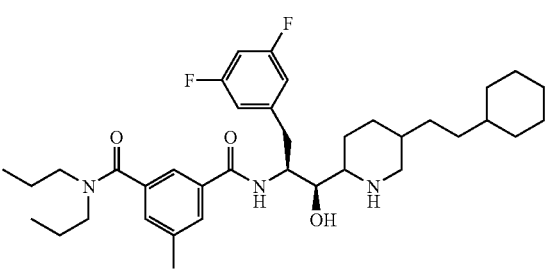

Step 1

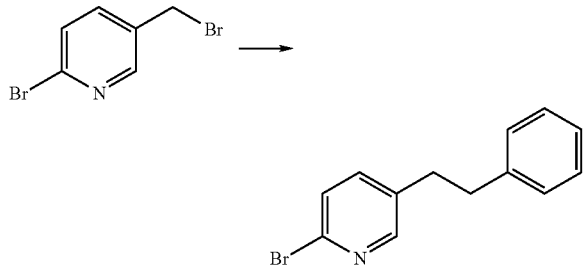

A mixture of 2-bromo-5-methylpyridine (10 g, 58 mmol), N-bromosuccinimide (15.5 g, 87.2 mmol), and azobisisobutyronitrile (0.25 g) in anhydrous CH$_2$Cl$_2$ (100 ml) was heated at 55° C. under irradiation (200 W lamp) for 6 h. The mixture was cooled down to RT, diluted with CH$_2$Cl$_2$ (200 ml), washed with saturated NaHCO$_3$ solution, dried (MgSO$_4$), filtered and concentrated. The residue was subjected to silica gel flash chromatography (5→7% EtOAc/hexanes) to afford the product (6.75 g, 46%).

Step 2

To a solution of the product from Step 1 (3.5 g, 14 mmol) in anhydrous THF (60 ml) at 0° C. was added benzylmagnesium chloride (2.0 M/THF, 10.6 ml, 21 mmol). The reaction mixture was stirred at 0° C. for 30 min and at RT for 2 h. The reaction was quenched with saturated NH₄Cl aqueous solution, extracted with EtOAc, dried (MgSO₄), filtered and concentrated. The residue was subjected to silica gel flash chromatography (5:95 EtOAc/hexanes) to afford the product (2.4 g, 66%).

Step 3

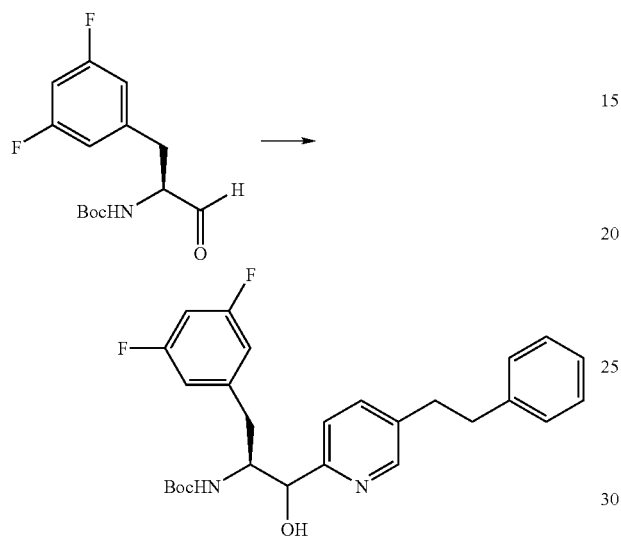

By essentially the same procedure set forth in Example 15, Step 1, the above product was prepared from the product of Step 2 in 61% yield.

Step 4

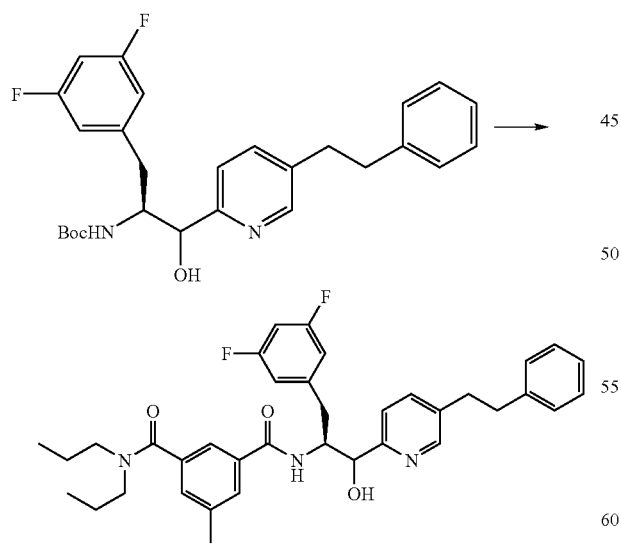

A flask was charged with product from Step 3 (350 mg), TFA (2 ml) and CH₂Cl₂ (10 ml). The reaction mixture was stirred at RT for 2 h then concentrated in vacuo. The residue was dissolved in a solution [5:95 (2M NH₃ in MeOH)/CH₂Cl₂], washed with saturated NaHCO₃ solution, dried (MgSO₄), filtered and concentrated. The residue was subjected to flash chromatography [3:97 (2M NH₃ in MeOH)/CH₂Cl₂] to isolate the intermediate product as a mixture of diastereoisomers (100 mg, 22%).

The intermediate product from above was treated with Preparation 1 (100 mg, 0.40 mmol), anhydrous DMF (5 ml) and EDC (100 mg, 0.54 mmol). The reaction mixture was stirred at RT for 4 h, then concentrated. The residue was dissolved in EtOAc, washed with water and brine, dried (MgSO₄), filtered and concentrated. The residue was subjected to PTLC (40:60 EtOAc/Hexane) to isolate the slower moving diastereoisomer as the desired product (57 mg).

Step 5

A flask charged with the product of Step 4 (21 mg), AcOH (5 ml) and PtO₂ (20 mg) was stirred under H₂ (1 atmosphere) for 2 h, then filtered and concentrated. The residue was separated on PTLC [7:93 (2M NH₃ in MeOH)/CH₂Cl₂] to give the desired product as a white solid (8 LCMS (Conditions A) $t_R$=5.65 min; m/e 626 (M+H)⁺.

Example 17

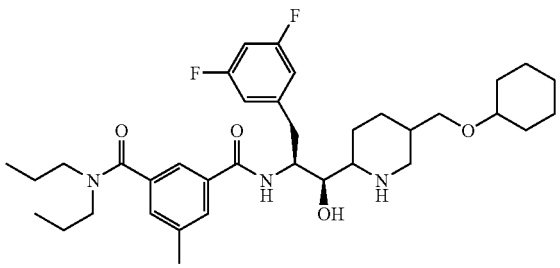

Step 1

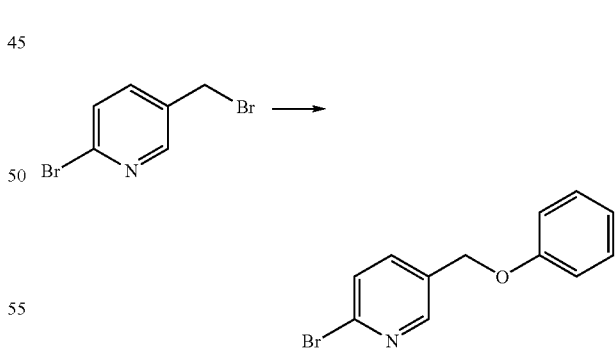

A mixture of the product from Example 16, Step 1 (0.70 g, 2.8 mmol), phenol (0.19 g, 2.0 mmol), and K₂CO₃ (0.58 g, 4.2 mmol) in anhydrous DMF (10 ml) was heated to 90° C. for 2 h. The mixture was cooled down to RT, diluted with water, extracted with ether, dried (MgSO₄), filtered and concentrated. The residue was subjected to flash chromatography (5:95 EtOAc/hexanes) to afford the product as white solid (0.38 g, 71%).

89

Step 2

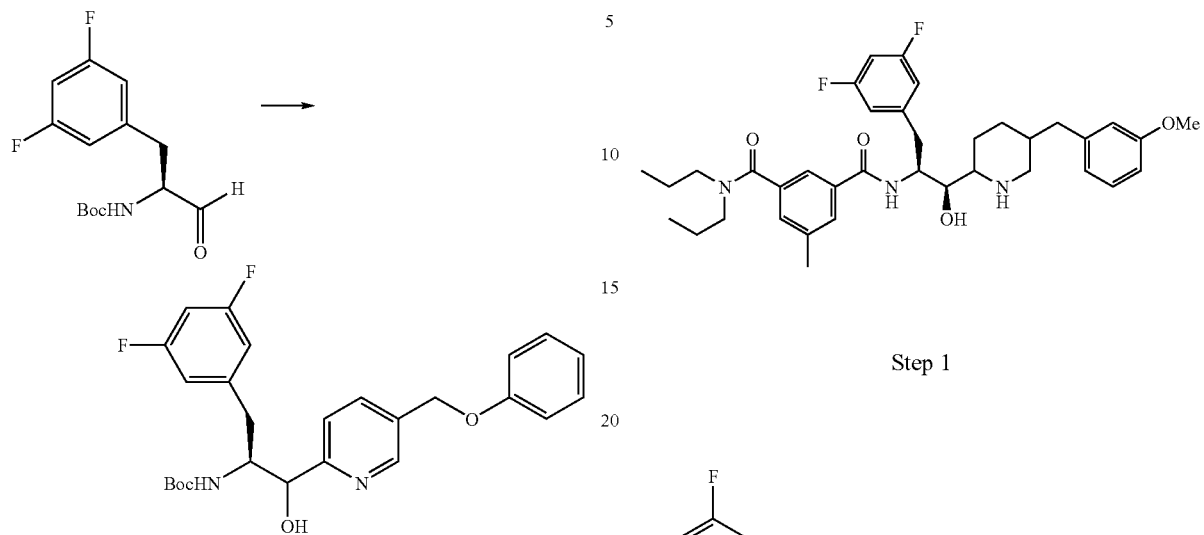

By essentially the same procedure set forth in Example 15, Step 1, the above product was prepared from the product of Step 1 in 30% yield.

Step 3

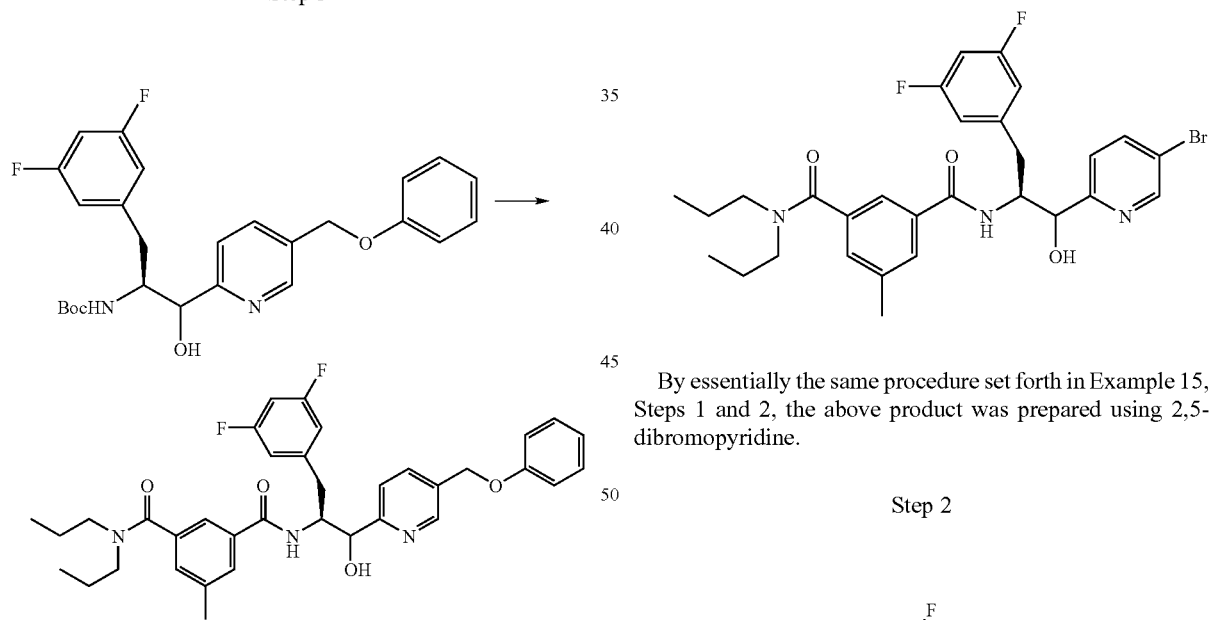

By essentially the same procedure set forth in Example 16, Step 4, the above product was prepared from the product of Step 2.

Step 4

By essentially the same procedure set forth in Example 16, Step 5, the above product was prepared from the product of Step 3 (11 mg, 0.018 mmol) as an off-white gum (2 mg, 18%). LCMS (Conditions A) $t_R$=4.48 min; m/e 628 (M+H)$^+$.

90

Example 18

Step 1

Step 2

By essentially the same procedure set forth in Example 15, Steps 1 and 2, the above product was prepared using 2,5-dibromopyridine.

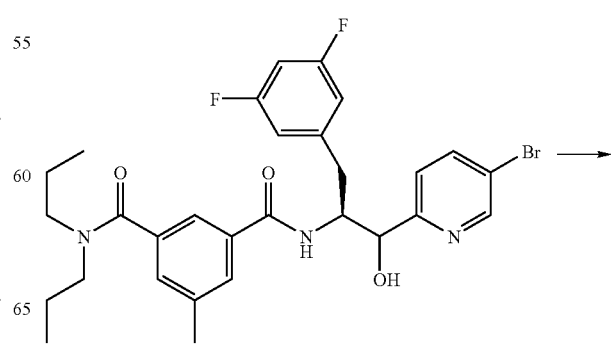

-continued

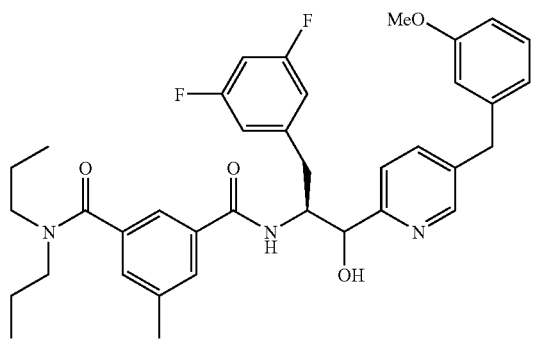

A mixture of the product from Step 1 (50 mg, 0.085 mmol), Pd(PPh₃)₄ (10 mg), 3-methoxybenzylzinc chloride (0.5 M/THF, 1.5 ml, 0.85 mmol) was heated at 120° C. for 24 h. The reaction was quenched with saturated NH₄Cl aqueous solution, extracted with EtOAc, dried (MgSO₄), filtered and concentrated. The residue was subjected to flash chromatography (10:90 EtOAc/CH₂Cl₂) to afford the product as a white solid (42 mg, 80%).

Step 3

Example 18 was prepared from the product of Step 2 (40 mg) by essentially the same procedure set forth in Example 15, Step 3. Off-white solid (12 mg). LCMS (Conditions A) $t_R$=5.16 min; m/e 636 (M+H)⁺

Example 19

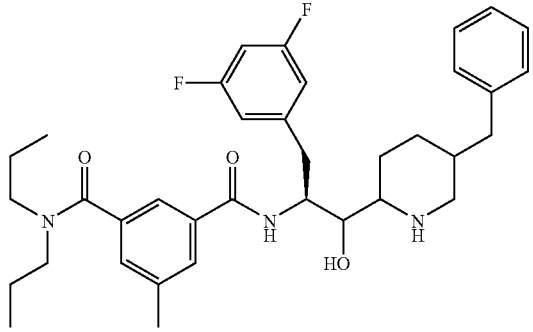

Following procedures similar to those described in Example 18 and using an appropriate organozinc derivative, the title compound was prepared. LCMS (Conditions A) shows two isomers, $t_R$=4.78 min and 4.98 min; both with 606 (M+H)⁺.

Example 20

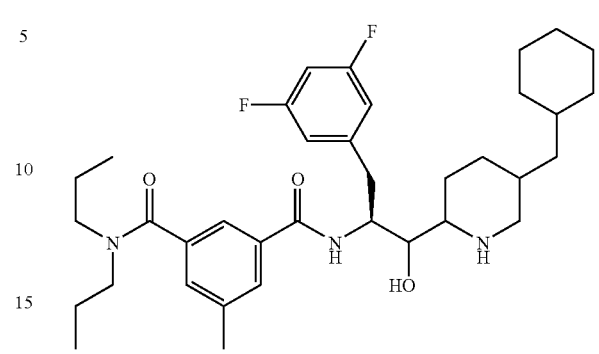

Following procedures similar to those described in Example 16, Step 5, the title compound was prepared from Example 19. LCMS (Conditions A) shows three isomers, $t_R$=5.31 min, 5.38 min and 5.52 min; all with 612 (M+H)⁺.

Example 21

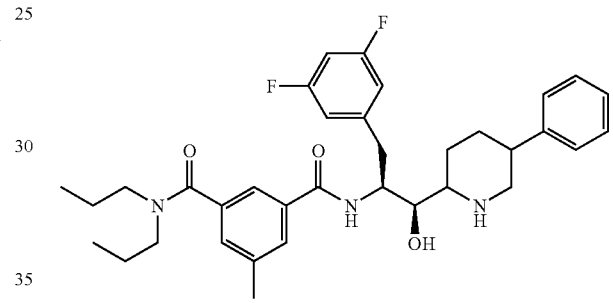

Step 1

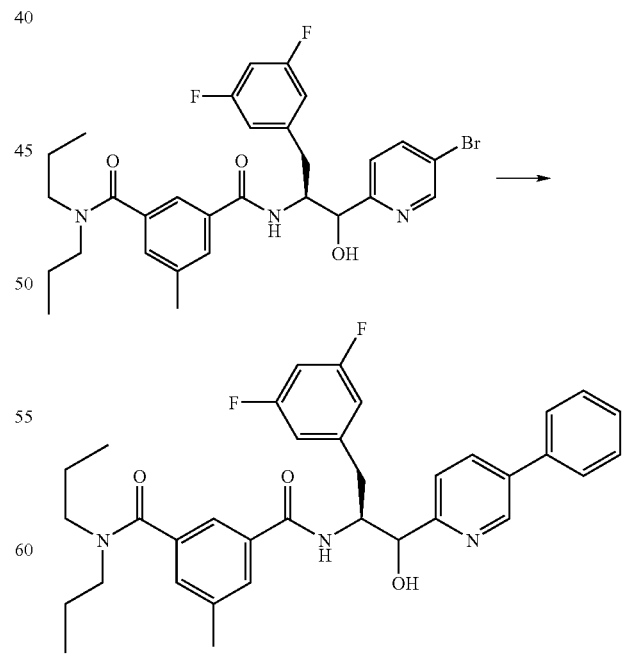

A mixture of the product of Example 18, Step 1 (75 mg), Pd(PPh₃)₄ (5 mg), phenylboronic acid (78 mg), K₂CO₃ (88 mg), ethanol (0.5 ml), water (1 ml), and toluene (2 ml) was heated at 120° C. for 16 h. The reaction was diluted with EtOAc, washed with saturated NaHCO₃ aqueous solution, dried (MgSO₄), filtered and concentrated. The residue was subjected to PTLC [3:97 (2M NH₃ in MeOH)/CH₂Cl₂] to afford the product (69 mg, 92%).

Step 2

By essentially the same procedure set forth in Example 15, Step 3, the above product was prepared from the product of Step 1 as a white solid. LCMS (Conditions A) $t_R$=4.78 min; m/e 592 (M+F1)⁺.

Example 22

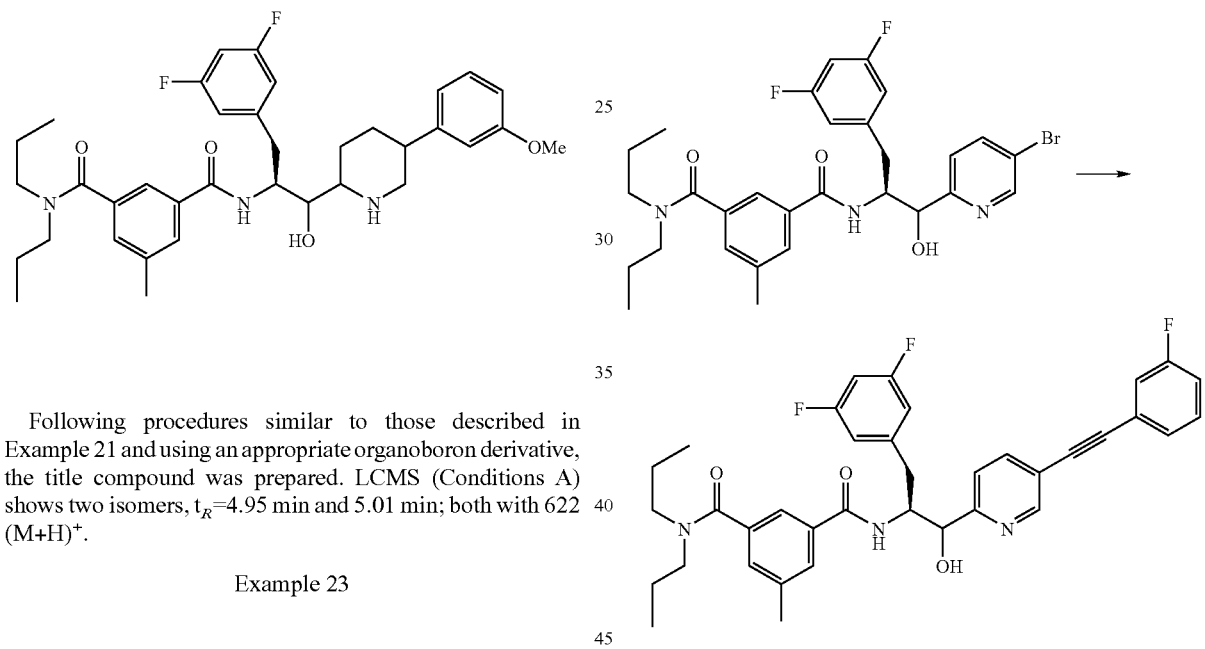

Following procedures similar to those described in Example 21 and using an appropriate organoboron derivative, the title compound was prepared. LCMS (Conditions A) shows two isomers, $t_R$=4.95 min and 5.01 min; both with 622 (M+H)⁺.

Example 23

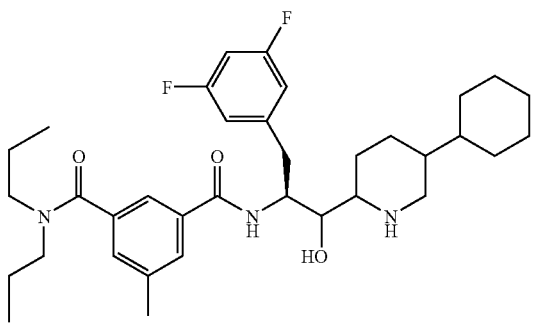

Following procedures similar to those described in Example 16, Step 5, the title compound was prepared from Example 21. LCMS (Conditions A) shows two isomers, $t_R$=5.12 min and 5.32 min; both with 598 (M+H)⁺.

Example 24

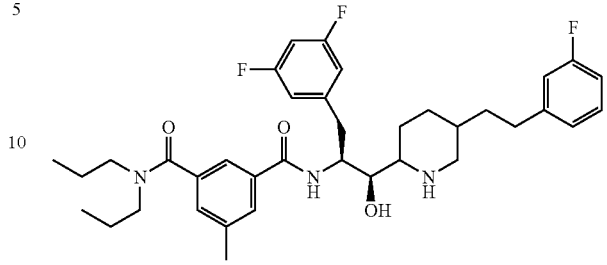

Step 1

A mixture of the product from Example 18, Step 1 (50 mg), PdCl₂(PPh₃)₂ (10 mg), 1-ethynyl-3-fluorobenzene (40 μl), CuI (4 mg), and diisopropylamine (3 ml) was heated at 100° C. for 16 h then concentrated in vacuo. The residue was dissolved in a solution [3:97 (2M NH₃ in MeOH)/CH₂Cl₂], washed with saturated NH₄Cl solution, dried (MgSO₄), filtered and concentrated. The residue was subjected to PTLC [3:97 (2M NH₃ in MeOH)/CH₂Cl₂] to afford the product (40 mg).

Step 2

By essentially the same procedure set forth in Example 15, Step 3, the above product was prepared from the product of Step 1 as a white solid. LCMS (Conditions A) $t_R$=4.31 min; m/e 638 (M+H)⁺.

Following procedures analogous to those described in Example 24 and using an appropriate terminal alkyne derivative, the following compounds were prepared:

| Example | Structure | LCMS (Conditions A) $t_R$, MS |
|---|---|---|
| 25 | 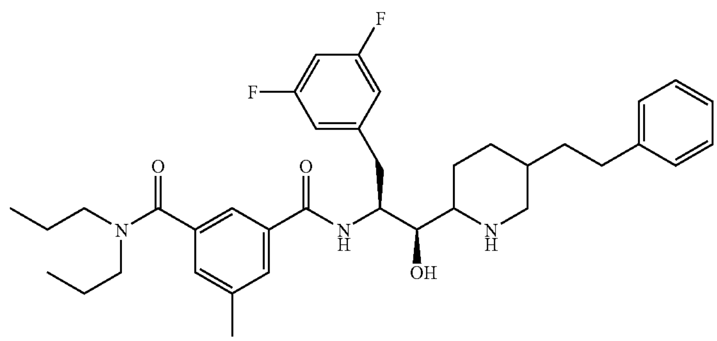 | 5.05-5.35 min; 620 (M + H)+ |
| 26 | 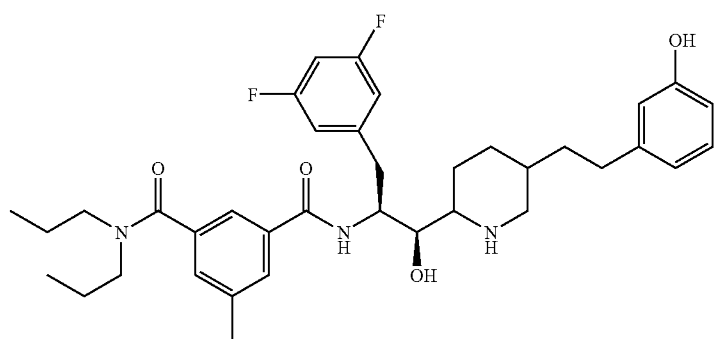 | 3.98 min; 636 (M + H)+ |
| 27 | 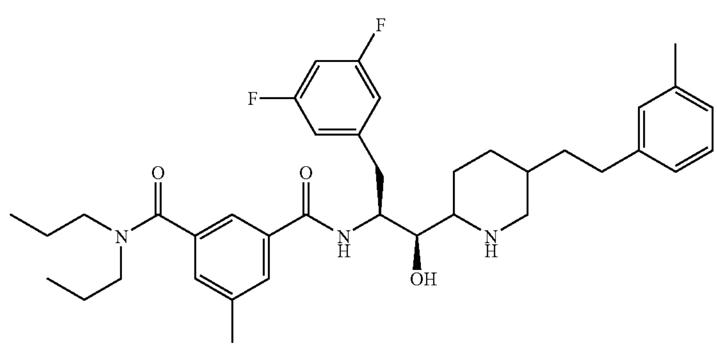 | 4.45 min; 634 (M + H)+ |
| 28 | 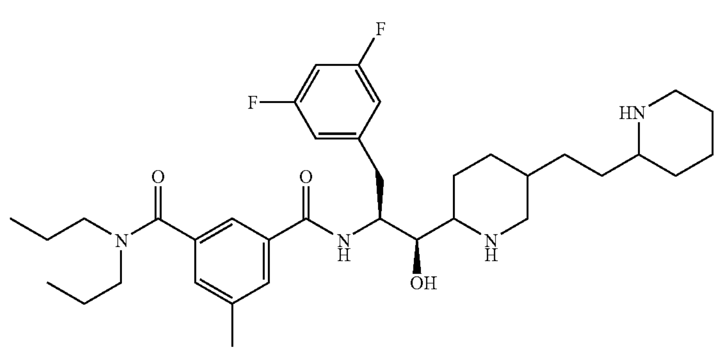 | 3.27 min; 627 (M + H)+ |

Example 29

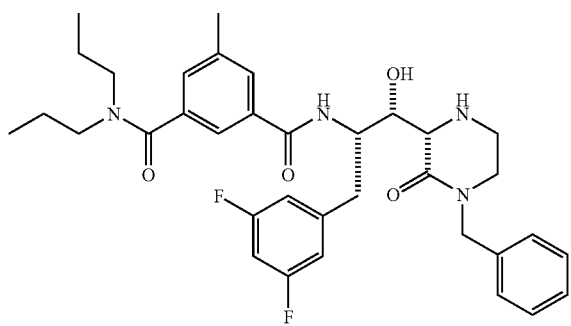

Step 1

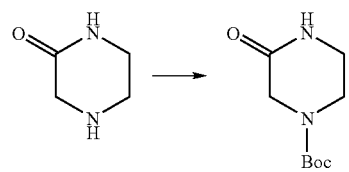

piperazin-2-one (1 g, 10 mmol) was dissolved in CH$_2$Cl$_2$ (40 ml), and Boc$_2$O (2.4 g, 11 mmol, 1.1 eq), Et$_3$N (2.02 g, 20 mmol, 2 eq) and DMAP (0.024 g, 0.2 mmol, 2 mol %) were added. After the mixture was stirred at RT for 16 h, it was acidified with 1 N HCl. The organic layer was separated, washed with saturated NaHCO$_3$, brine, dried (Na$_2$SO$_4$), and concentrated in vacuo to give the product (1.8 g, 90%) as a white solid. $^1$H NMR (CDCl$_3$, 300 MHz) δ 6.70 (1H, bs), 4.08 (2H, s), 3.62 (2H, t, J=6.0 Hz), 3.37 (2H, m), 1.46 (9H, s).

Step 2

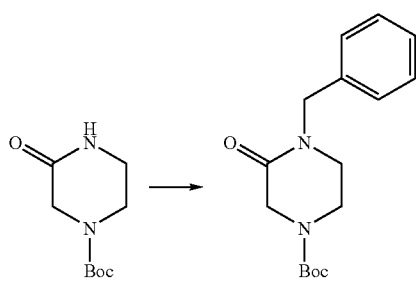

To a solution of the product of Step 1 (1.17 g, 5.87 mmol) in DMF (25 ml) at RT was added NaH (60% dispersion in mineral oil, 352 mg, 8.8 mmol, 1.5 eq) and the resulting mixture was stirred at RT for 2 h. Benzyl bromide (0.84 ml, 7.04 mmol, 1.2 eq) was added and the reaction was heated at 70° C. for 16 h. The reaction mixture was cooled to RT and the excess NaH was quenched carefully by the dropwise addition of MeOH. The solvent was evaporated in vacuo and the residue was chromatographed on silica (70% EtOAc/hexanes) to give the product (1.6 g, 95%) as a white solid. $^1$H NMR (CDCl$_3$, 300 MHz) δ 7.28 (5H, m), 4.62 (2H, s), 4.16 (2H, s), 3.58 (2H, m, J=5.1 Hz), 3.25 (2H, m, J=5.4 Hz), 1.46 (9H, s).

Step 3

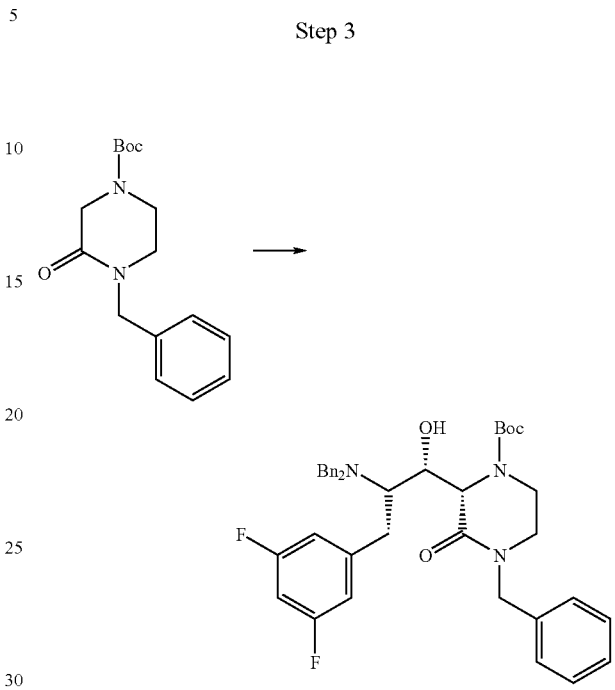

To a solution of diisopropylamine (3.712 g, 36.68 mmol) in anhydrous THF (20 ml) at −78° C. was added 2.5 M butyllithium in hexanes (14.2 ml, 35.5 mmol). After 5 min, the solution was placed in an ice-water bath and stirred for 30 min. The mixture was cooled to −78° C. again and a solution of the product of Step 2 (8.875 g, 30.57 mmol) in THF (30 ml) was added and the mixture was stirred for 1.5 h at −78° C. A solution of Preparation 10 (12.1 g, 33.11 mmol) in THF (20 ml) was added and the resulting mixture was allowed to warm to RT overnight. The mixture was partitioned between ether (150 ml) and water (200 ml). The aqueous layer was extracted with ether (3×150 ml). The combined organic layers were dried (MgSO$_4$), concentrated, and purified by column chromatography (gradient 0-20% EtOAc/Hexanes) to give a light yellow solid (9.00 g, 41%). MS m/e 656 (M+H)$^+$.

Step 4

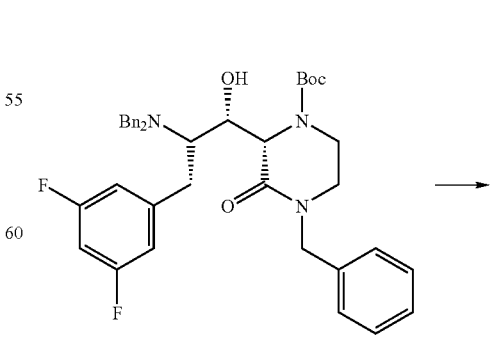

-continued

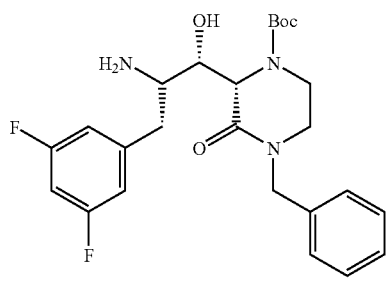

A mixture of the product of Step 3 (495 mg, 0.755 mmol), 20% Pd(OH)₂/C (493 mg), and a catalytic amount of acetic acid in EtOH (15 ml) was stirred under H₂ (1 atm) for 5 h at RT. The mixture was filtered through a pad of Celite and concentrated. The residue was dissolved in CH₂Cl₂ (50 ml) and washed with aq. NH₄OH (15 ml). The organic layer was dried (MgSO₄) and concentrated to give the product (326 mg, 91%). MS m/e 476 (M+H)⁺.

Step 5

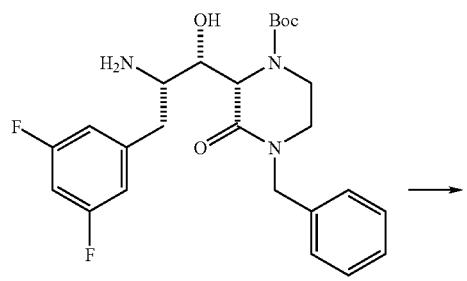

-continued

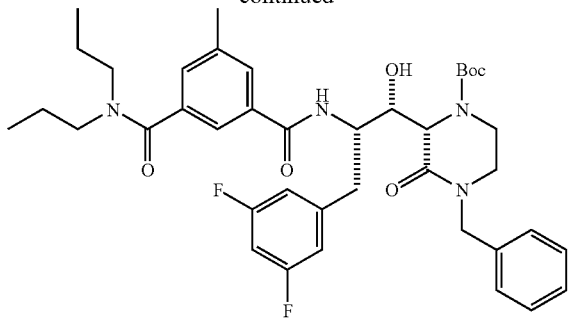

A mixture of the product of Step 4 (42 mg, 0.09 mmol), Preparation 1 (27 mg, 0.10 mmol), HOBt (14 mg, 0.10 mmol), EDCI (18 mg, 0.09 mmol), and triethylamine (50 µl, 0.37 mmol) in DMF (2 ml) was stirred at RT for 16 h. The mixture was diluted with CH₂Cl₂ (50 ml), washed with 0.5 N NaOH and H₂O, dried (MgSO₄), concentrated, and purified by PTLC (3.5% MeOH/CH₂Cl₂) to give the product (20 mg, 31%). MS m/e 721 (M+H)⁺.

Step 6

An ice-cold solution of the product of Step 5 (69 mg, 0.096 mmol) and TFA (0.4 ml) in CH₂Cl₂ (4 ml) was stirred for 30 min, then allowed to warm to RT and stirred for 3 h. The mixture was diluted with CH₂Cl₂ (50 ml), and washed with 5N NH₄OH (10 ml). The organic layer was dried (MgSO₄), concentrated and purified by PTLC (5:95 MeOH/CH₂Cl₂) to give the product (47 mg, 79%). LCMS (Conditions E) $t_R$=5.99 min; 621.2 (M+H)⁺. ¹H NMR (CDCl₃, 400 MHz) δ 7.50 (m, 2H), 7.4-7.0 (m, 7H), 6.85 (m, 2H), 6.60 (m, 1H), 4.68 (m, 2H), 4.23 (m, 1H), 4.11 (m, 1H), 3.66 (m, 1H), 3.43 (m, 2H), 3.32 (m, 1H), 3.25-2.9 (m, 8H), 2.37 (s, 3H), 1.67 (m, 2H), 1.48 (m, 2H), 0.96 (m, 3H), 0.70 (t, 3H, J=7.2 Hz). The following Examples were prepared from the product of Example 29, Step 4 and the appropriate acid, in analogy to Example 29, Steps 5 and 6

| Example | Acid | Example | LCMS data (Conditions A) $t_R$; m/e |
|---|---|---|---|
| 29A | Preparation 6 | 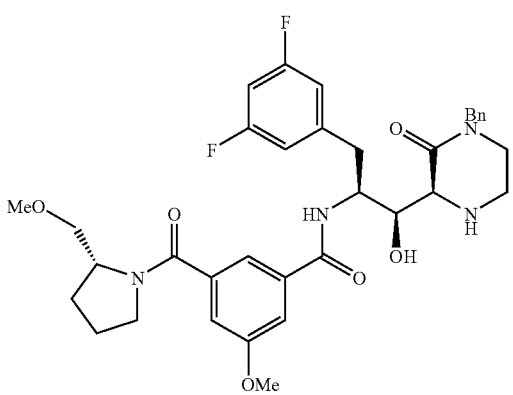 | 3.01 min; 651 (M + H)⁺ |

-continued
| Example | Acid | Example | LCMS data (Conditions A) $t_R$; m/e |
|---|---|---|---|
| 29B | Preparation 4 | 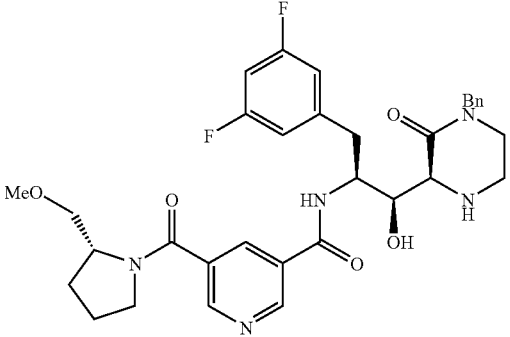 | 2.83 min; 622 (M + H)$^+$ |
| 29C | Preparation 5 | 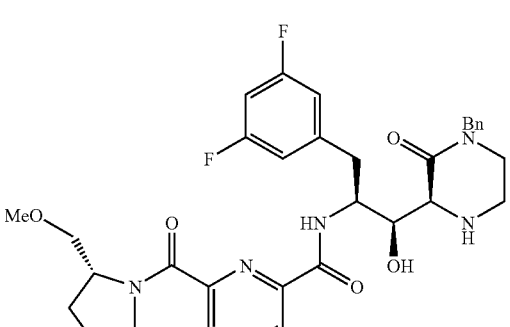 | 3.06 min; 622 (M + H)$^+$ |
| 29D | Preparation 3 | 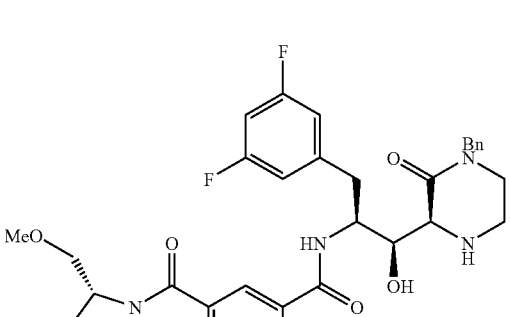 | 3.45 min; 635 (M + H)$^+$ |

Example 30

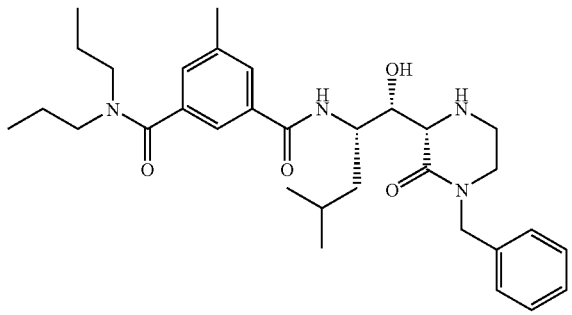

The title compound was prepared by essentially the procedure of Example 29, using Preparation 11 in place of Preparation 10. $^1$H NMR (CDCl$_3$, 400 MHz): δ=7.57 (m, 2H), 7.1-7.3 (m, 6H), 6.84 (d, 1H, J=9.6 Hz), 4.64 (d, 1H, J=14.4 Hz), 4.47 (m, 1H), 4.06 (m, 2H), 3.0-3.5 (m, 8H), 2.89 (m, 1H), 2.35 (s, 3H), 1.3-1.7 (m, 7H), 0.91 (m, 9H), 0.68 (m, 3H). LCMS (Conditions A): t$_R$=3.72 min; m/e 551 (M+H)$^+$

Example 31

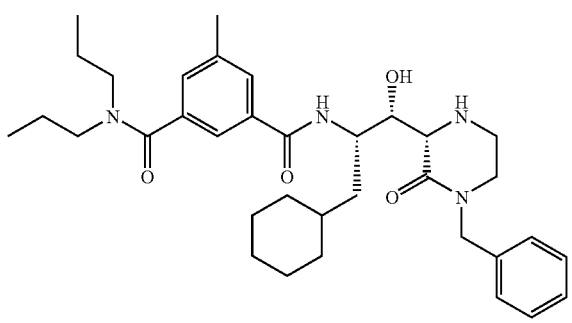

The title compound was prepared by essentially the procedure of Example 29, using Preparation 12 in place of Preparation 10. $^1$H NMR (CDCl$_3$, 400 MHz): δ=7.61 (m, 2H), 7.30 (m, 4H), 7.18 (m, 2H), 6.80 (d, 1H, J=9.6 Hz), 4.67 (d, 1H, J=14.4 Hz), 4.53 (m, 1H), 4.14 (d, 1H, J=14.4 Hz), 4.10 (m, 1H), 2.9-3.6 (m, 9H), 2.40 (s, 3H), 0.65-2.0 (m, 24H). MS m/e 591 (M+H)$^+$

Example 32

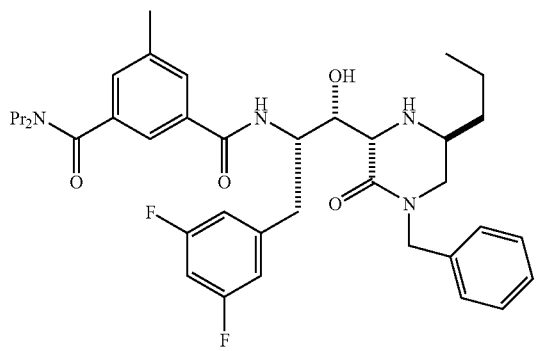

Step 1

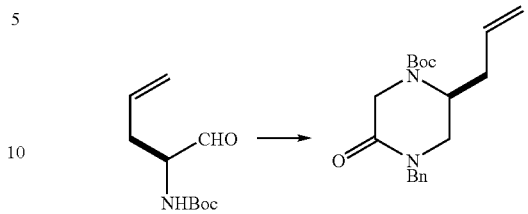

The product was obtained by essentially the procedure of Dinsmore, et al., *Org. Lett.* (2001), 865-868. To a solution of benzylamine (0.72 ml, 6.6 mmol) and (S)-N-Boc-allylglycinal (1.3 g, 6.6 mmol) in 1,2-dichloroethane (20 ml) at 0° C. was added 4 Å molecular sieves followed by sodium triacetoxyborohydride (2.1 g, 10.0 mmol). The reaction was allowed to warm to RT, then stirred for 14 h. The mixture was poured into EtOAc, washed with saturated NaHCO$_3$, brine, dried (Na$_2$SO$_4$), filtered and concentrated. Purification by silica gel column chromatography (4% CH$_3$OH/CH$_2$Cl$_2$) gave 1.9 g (83%) of the reductive alkylation product as a yellow oil. $^1$H NMR (CDCl$_3$, 300 MHz) δ 7.33-7.25 (m, 5H), 5.84-5.70 (m, 1H), 5.10-5.01 (m, 2H), 4.69 (bs, 1H), 3.79 (q, J=13.2 Hz, 2H), 2.68 (d, J=5.4 Hz, 2H), 2.27 (t, J=7.2 Hz, 2H), 1.44 (s, 9H). MS (ESI) m/e 291.1 (M+H)$^+$. To a solution of the reductive alkylation product (1.9 g, 6.5 mmol) in a 1:1 solution of EtOAc and saturated NaHCO$_3$ (40 ml) at 0° C., chloroacetyl chloride (1.0 ml, 13.0 mmol) was added and the mixture was stirred for 0.5 h. The layers were separated and the aqueous layer was extracted with EtOAc (3×). The organic layers were combined, washed with brine, dried (Na$_2$SO$_4$), filtered and concentrated to give 2.3 g (85%) of the chloride which was used without further purification. $^1$H NMR (CDCl$_3$, 300 MHz) δ 7.40-7.17 (m, 5H), 5.79-5.68 (m, 1H), 5.11-5.06 (m, 2H), 4.82-4.78 (m, 1H), 4.65 (q, J=17.3 Hz, 1H), 4.38-4.19 (m, 1H), 4.06 (d, J=1.8 Hz, 1H), 3.98-3.88 (m, 1H), 3.57-3.37 (m, 1H), 3.05 (d, J=8.4 Hz, 1H), 2.23 (t, J=5.7 Hz, 2H), 1.43 (s, 9H). MS (ESI) m/e 389.2 (M+Na)$^+$. To a solution of the chloride (2.0 g, 5.5 mmol) in DMF (20 ml) was added cesium carbonate (3.6 g, 10.9 mmol) and the mixture was heated to 65° C. for 2 h, cooled to 25° C. and poured into a 90% solution of EtOAc/Hexane. The organic layer was washed (1×H$_2$O, 1× brine), dried (Na$_2$SO$_4$), filtered and concentrated. Purification by silica gel column chromatography (50% EtOAc/Hexane) gave the product (1.1 g, 61%) as a white solid. $^1$H NMR (CDCl$_3$, 300 MHz) δ 7.36-7.28 (m, 5H), 5.60-5.51 (m, 1H), 5.01-4.77 (m, 3H), 4.41-4.32 (m, 3H), 3.83 (d, J=18.6 Hz, 1H), 3.46 (dd, J=12.6, 4.5 Hz, 1H), 3.07 (d, J=12.3 Hz, 1H), 2.27 (q, J=7.2 Hz, 1H), 2.11 (q, J=7.2 Hz, 1H), 1.45 (s, 9H). MS (ESI) m/e 330.8 (M+H)$^+$.

Step 2

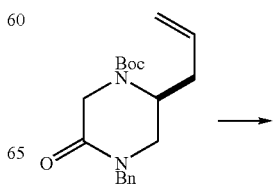

-continued

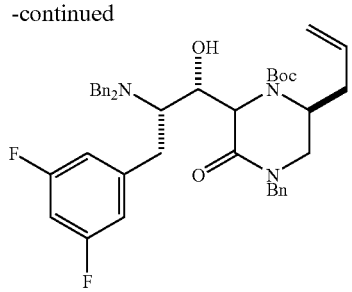

1M LDA in THF (1.0 ml, 1.0 mmol) was added dropwise to a solution of the product of Step 1 (0.25 g, 0.76 mmol) in THF (5 ml) at −78° C. under argon. After 10 min at −78° C., a solution of Preparation 10 (0.28 g, 0.76 mmol) in THF (1 ml) was added dropwise and the mixture was stirred for 0.5 h. The reaction mixture was quenched with saturated aqueous NH$_4$Cl, then partitioned between EtOAc (25 ml) and saturated NaHCO$_3$. The organic layer was dried (Na$_2$SO$_4$), filtered and concentrated. the residue was subjected to silica gel column chromatography (3:7 EtOAc/hexanes) to give the product (0.20 g, 38%). $^1$H NMR (CDCl$_3$, 300 MHz) δ 7.42-6.99 (15H, m), 6.78-6.64 (3H, m), 5.47-5.24 (1H, m), 4.95 (1H, d, j=10.2 Hz), 4.70-4.62 (3H, m), 4.51-4.46 (3H, m), 3.94 (2H, d, J=14.1 Hz), 3.73-3.69 (1H, m), 3.59-3.54 (1H, m), 3.45 (2H, d, j=14.7 Hz), 3.30-3.28 (1H, m), 3.18-3.12 (1H, m), 3.01-2.87 (1H, m), 2.38-2.20 (m, 1H), 2.05-1.98 (m, 1H), 1.40 (9H, s). MS (ESI) m/e 696.1 (M+H)$^+$.

Step 3

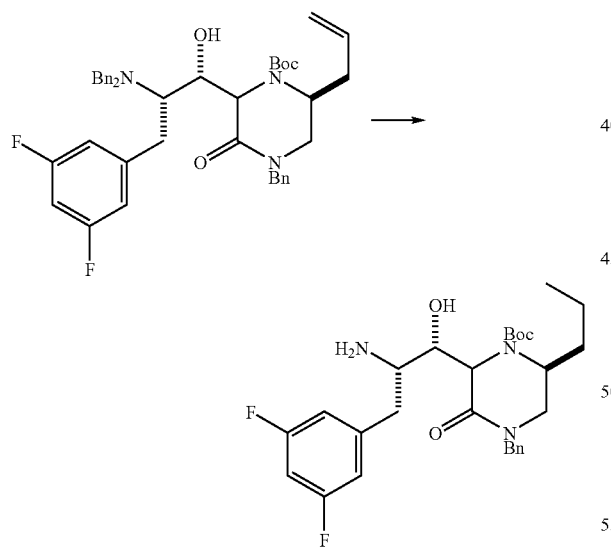

A flask containing the product of Step 2 (0.10 g, 0.14 mmol) in ethanol (40 ml) was flushed with argon gas. To the solution was added 10% palladium on carbon (20 mg) and a catalytic amount (2 drops) of concentrated HCl and the mixture was stirred under 1 atm H$_2$ for 2 h. The reaction was flushed with argon, filtered and the volatiles were removed in vacuo to give 0.070 g (88%) of the HCl salt of the product which was used without further purification. $^1$H NMR (CD$_3$OD, 300 MHz) δ 7.65-7.23 (m, 5H), 7.07-6.87 (m, 3H), 5.03-4.83 (m, 1H), 5.58 (m, 1H), 4.35-4.29 (m, 2H), 3.96- 3.83 (m, 2H), 3.69-3.19 (m, 3H), 3.05-2.91 (q, 1H), 1.45 (s, 9H), 1.39-1.20 (m, 2H), 1.09-0.87 (m, 2H), 0.86-0.63 (m, 3H).

Step 4

Using essentially the procedure of Example 29, Steps 5-6, the title compound was obtained. LCMS (Conditions E) $t_R$=6.3 min; 663.1 (M+H)$^+$. $^1$H NMR (CD$_3$OD, 300 MHz) δ 7.68 (s, 1H), 7.54 (s, 1H), 7.37 (s, 1H), 7.31-7.29 (m, 3H), 7.28-7.22 (m, 2H), 6.89 (dd, J=8.6, 2.3 Hz, 2H), 6.82-6.71 (m, 1H), 4.99-4.83 (m, 1H), 4.65 (dd, J=9.8, 2.7 Hz, 1H), 4.59-4.49 (m, 1H), 4.31 (d, J=2.7 Hz, 1H), 3.91-3.81 (m, 1H), 3.64 (dd, J=13.8, 4.2 Hz, 1H), 3.49-3.43 (m, 4H), 3.23-3.13 (m, 3H), 3.01-2.91 (m, 1H), 2.44 (s, 3H), 1.80-1.40 (m, 5H), 1.29 (bs, 1H), 1.28-1.10 (m, 1H), 1.02-0.87 (m, 4H), 0.81 (t, J=7.1 Hz, 3H), 0.66 (t, J=7.2 Hz, 3H).

Example 33

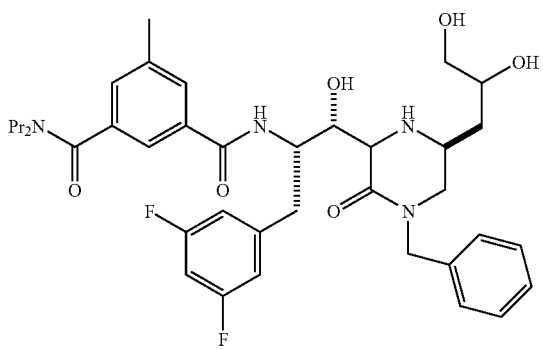

Step 1

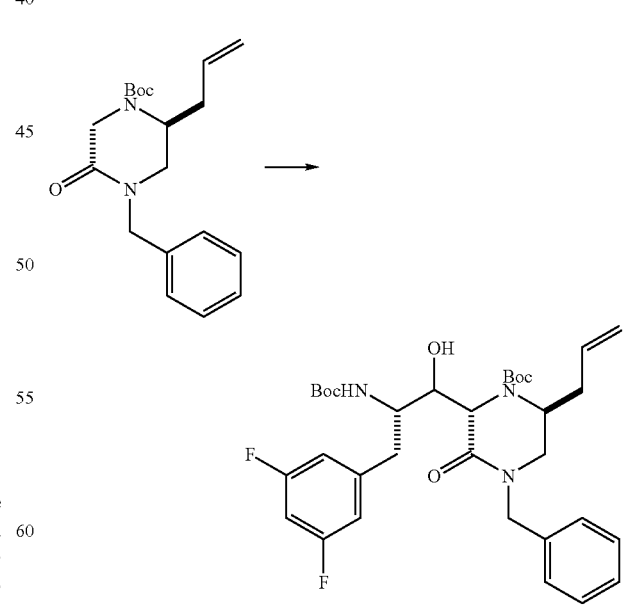

To a stirred solution of the product of Example 32, Step 1 (0.33 g, 1.0 mmol) in THF (5 ml) cooled to −78° C. under argon was added 1M LDA in THF (2.0 ml, 2.0 mmol) dropwise. After stirring 10 min at −78° C., a solution of Preparation 9 (0.28 g, 1.0 mmol) in THF (1 ml) was added dropwise and the mixture was stirred for 1 h. The reaction mixture with saturated aqueous NH$_4$Cl, then partitioned between EtOAc (25 ml) and NaHCO$_3$. The organic layer was dried (Na$_2$SO$_4$), filtered and concentrated, followed by silica gel column chromatography (3:7 EtOAc/hexanes) to give the product (0.16 g, 26%). $^1$H NMR (CDCl$_3$, 300 MHz) δ 7.34-7.19 (5H, m), 6.88-6.58 (3H, m), 5.42-5.12 (2H, m), 4.93-4.60 (3H, m), 4.40 (1H, d, J=6.3 Hz), 4.32-4.26 (1H, m), 4.13-3.90 (2H, m), 3.68-3.57 (1H, m), 3.19-2.80 (3H, m), 2.13-1.74 (2H, m), 1.50-1.30 (m, 18H). MS (ESI) m/e 638.1 (M+Na)$^+$.

Step 2

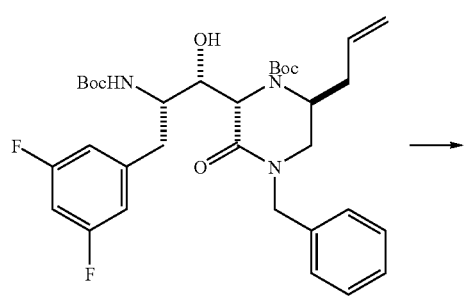

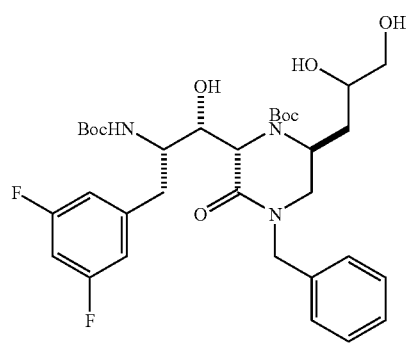

The oxidation was based on the procedure of Itoh, et al, *Org. Lett.* (2002), 2469-2472. To a stirred solution of the product of Step 1 (0.026 g, 0.042 mmol) in MeCN—H$_2$O (2:1; 3 ml) was added 4% OsO$_4$ in H$_2$O (0.027 ml, 0.0042 mmol) and NMO (0.029 mg, 0.211 mmol) at 25° C. After stirring 2 days, a saturated solution of aqueous Na$_2$S$_2$O$_3$ (1 ml) was added and the mixture was stirred for 1 h and extracted with CHCl$_3$. The organic layers were combined, washed with a saturated aqueous solution of sodium chloride, dried over Na$_2$SO$_4$, filtered and purified by column chromatography (2-10% CH$_3$OH/CH$_2$Cl$_2$) to give the product (0.014 g, 51%). $^1$H NMR (CDCl$_3$, 300 MHz) δ 7.41-7.09 (m, 8H), 5.76-5.49 (m, 1H), 4.95-4.72 (m, 2H), 4.43-4.09 (m, 3H), 3.87-3.72 (m, 2H), 3.49-3.39 (m, 1H), 3.09 (m, 1H), 2.45-2.37 (m, 1H), 2.31-2.19 (m, 1H), 2.18-2.02 (m, 1H), 2.00-0.73 (m, 22H). MS (ESI) m/e 649.8 (M+H)$^+$.

Step 3

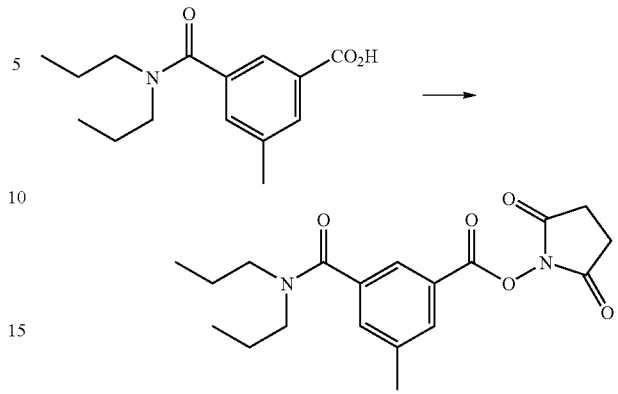

To a solution of Preparation 1 (0.30 g, 1.14 mmol) in CH$_2$Cl$_2$ (20 ml) was added N-hydroxysuccinimide (0.26 g, 2.28 mmol, 2 eq), HOBt (0.31 g, 2.28 mmol, 2 eq), DIEA (1.0 ml, 5.7 mmol, 5 eq), and EDC (0.65 g, 3.42 mmol, 3 eq). The mixture was stirred at RT for 16 h, then washed with H$_2$O (10 ml), dried (MgSO$_4$), and concentrated in vacuo. The residue was chromatographed (SiO$_2$, 30% to 60% EtOAc/hexanes) to give the product (0.29 g, 72%). $^1$H NMR (CDCl$_3$, 300 MHz) δ 7.97 (s, 1H), 7.90 (s, 1H), 7.49 (s, 1H), 3.45 (m, 2H), 3.15 (m, 2H), 2.91 (s, 4H), 2.45 (s, 3H), 1.68 (m, 2H), 1.55 (m, 2H), 0.98 (m, 3H), 0.77 (m, 3H).

Step 4

The product of Step 2 was treated with 1:1 TFA/CH$_2$Cl$_2$ (1 ml) at RT for 1 h. The reaction mixture was diluted with toluene, concentrated in vacuo, and the procedure was repeated twice to remove residual TFA. The product was dissolved in CH$_2$Cl$_2$ (2 ml) and treated with DIEA (0.016 ml, 0.091 mmol) and the product of Step 3 (0.013 g, 0.036 mmol) at RT for 16 h. The reaction mixture was partitioned between EtOAc (20 ml) and sat'd NaHCO$_3$. The organic layer was dried (Na$_2$SO$_4$), filtered and evaporated. Reverse phase hplc gave the product as a mixture of diastereomers. t$_R$=5.9 min (conditions E). $^1$H NMR (CD$_3$Cl, 300 MHz) δ 7.65-7.49 (m, 2H), 7.38-7.00 (m, 5H), 6.97-6.73 (m, 2H), 6.70-6.51 (m, 1H), 5.16-2.90 (m, 18H), 2.32 (s, 3H), 1.73-1.60 (m, 2H), 1.59-1.40 (m, 2H), 0.94 (t, J=7.5 Hz, 3H), 0.74 (t, J=6.9 Hz, 3H). MS (ESI) m/e 695.2 (M+H)$^+$.

Example 34

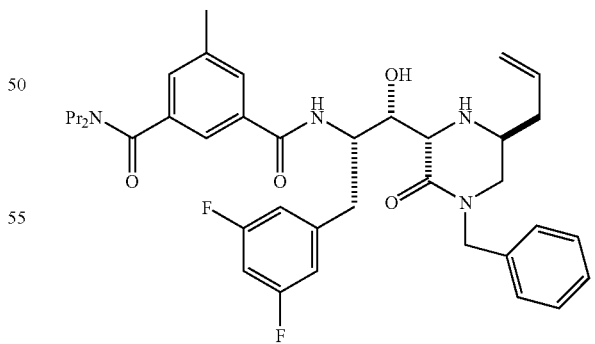

Using essentially the procedure of Example 33, Step 4, the title compound was obtained from the product of Example 33, Step 1 after column chromatography (SiO$_2$, gradient; 2:98-5:95% CH$_3$OH/CH$_2$Cl$_2$). LCMS (Conditions E) t$_R$=6.2 min; 661.1 (M+H)$^+$. $^1$H NMR (CD$_3$Cl, 300 MHz) δ 7.55 (s, 1H), 7.50 (s, 1H), 7.28-7.23 (m, 5H), 7.13-7.10 (m, 1H), 6.86-6.81 (m, 2H), 6.67-6.61 (m, 1H), 5.69-5.60 (m, 1H), 5.06-4.94 (m, 2H), 4.76 (dd, 1H), 4.63 (d, j=14.7, 1H), 4.12 (d, j=14.1 Hz, 1H), 3.83 (d, j=7.2 Hz, 1H), 3.62 (d, j=7.5 Hz, 1H), 3.52-3.32 (m, 2H), 3.22-2.91 (m, 6H), 2.38 (s, 3H), 2.09 (t, J=6.6 Hz, 2H), 1.79-1.59 (m, 2H), 1.55-1.43 (m, 2H), 0.97 (t, J=7.8 Hz, 3H), 0.71 (t, J=7.8 Hz, 3H).

Following the procedures described in Example 29 and 33, the following compounds were prepared using the appropriate piperazinone starting material and the aldehyde indicated below:

| Ex. | Aldehyde | Example | LCMS (Conditions E) m/e, $t_R$ (min) |
|---|---|---|---|
| 34A | Prep. 9 | | 639.1 $t_R$ = 6.04 |
| 34B | Prep. 9 | | 651.2 $t_R$ = 6.01 |
| 34C | Prep. 9 | | 651.2 $t_R$ = 5.94 |
| 34D | Prep. 9 | | 655.2 $t_R$ = 6.21 |

| Ex. | Aldehyde | Example | LCMS (Conditions E) m/e, $t_R$ (min) |
|---|---|---|---|
| 34E | Prep. 9 | 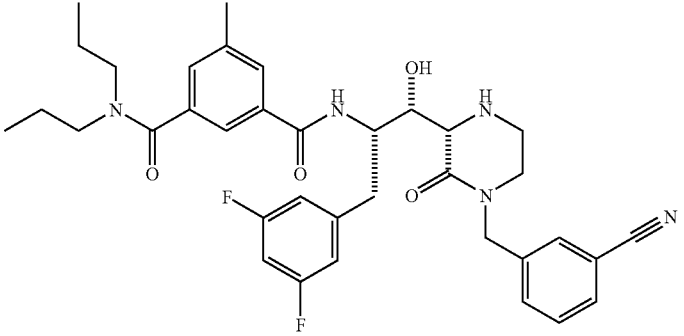 | 646.2 $t_R$ = 6.14 |
| 34F | Prep. 10 | 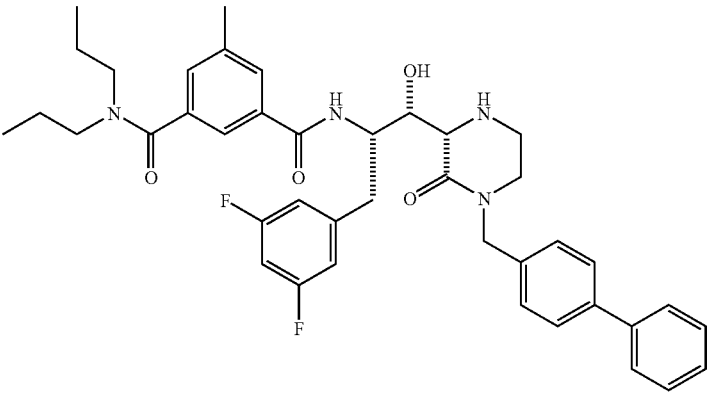 | 697.2 $t_R$ = 6.56 |
| 34G | Prep. 10 | 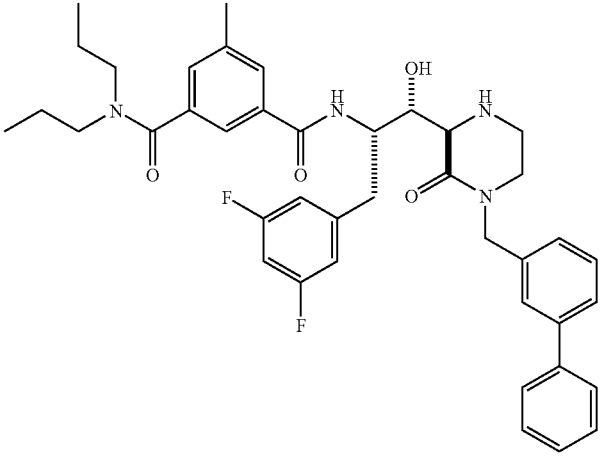 | 697.3 $t_R$ = 6.24 |

| Ex. | Aldehyde | Example | LCMS (Conditions E) m/e, $t_R$ (min) |
|---|---|---|---|
| 34H | Prep. 10 | 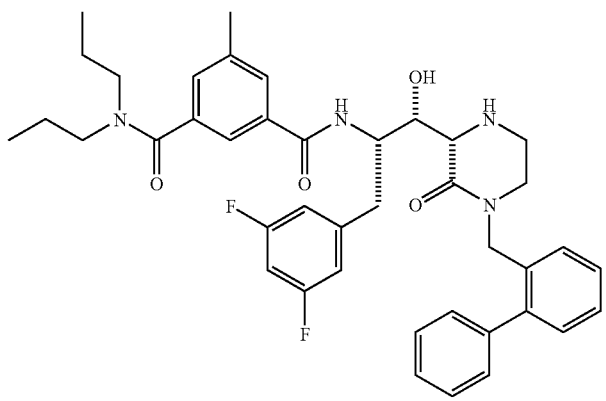 | 697.1<br>$t_R$ = 6.72 |
| 34I | Prep. 10 | 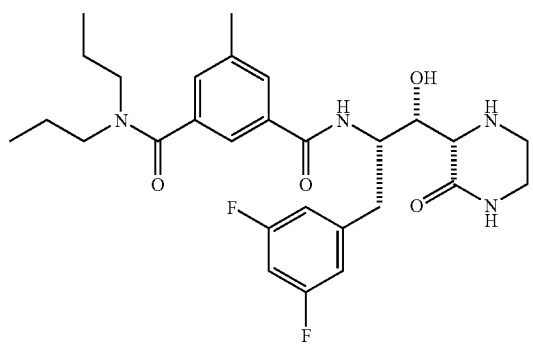 | 531.1<br>$t_R$ = 5.48 |
| 34J | Prep. 10 | 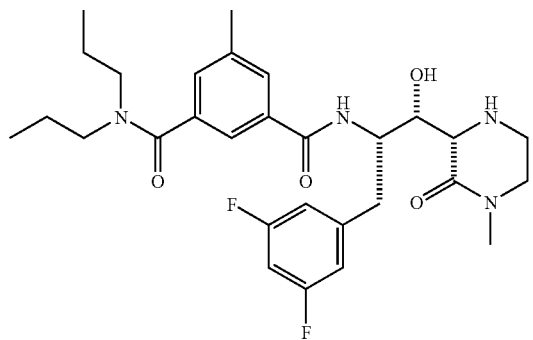 | 545.1<br>$t_R$ = 5.45 |
| 34K | Prep. 10 | 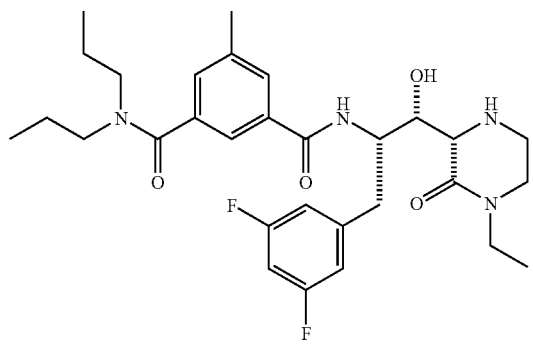 | 559.1<br>$t_R$ = 5.53 |

| Ex. | Aldehyde | Example | LCMS (Conditions E) m/e, $t_R$ (min) |
|---|---|---|---|
| 34L | Prep. 9 | | 573.2 $t_R$ = 5.65 |
| 34M | Prep. 10 | | 587.2 $t_R$ = 5.98 |
| 34N | Prep. 10 | | 585.2 $t_R$ = 5.84 |
Example 35
Step 1
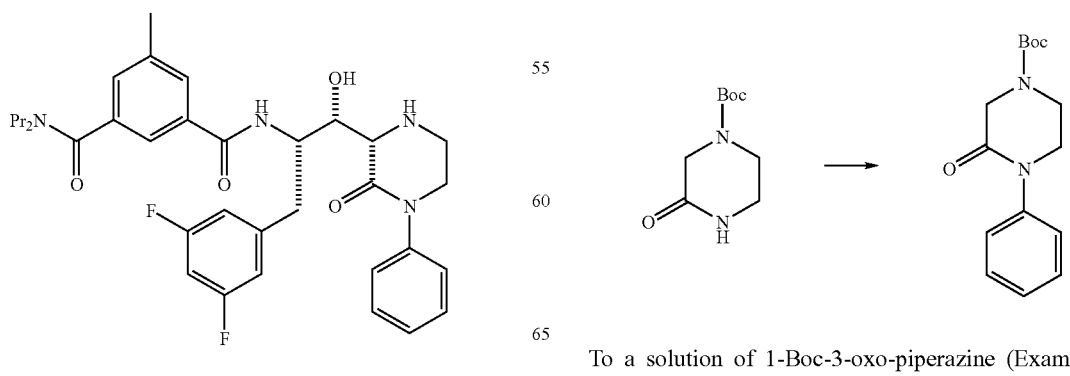
To a solution of 1-Boc-3-oxo-piperazine (Example 29, Step 1; 0.15 g, 0.75 mmol), iodobenzene (0.070 ml, 0.63 mmol), N,N'-dimethylethylenediamine (0.007 ml, 0.063 mmol) and potassium phosphate (0.27 g, 1.3 mmol) in toluene (1 ml) was added copper iodide (6.0 mg, 0.031 mmol). The reaction mixture was heated to 80° C. for 5 h. The reaction mixture was cooled to 25° C., diluted with CH$_2$Cl$_2$ (25 ml) and filtered through a plug of silica using 40% EtOAc/Hexane as eluent to give 0.10 g (58%) of the product as a white solid. $^1$H NMR (CDCl$_3$, 300 MHz) δ 7.44-7.39 (m, 5H), 4.26 (s, 2H), 3.79-3.74 (m, 4H), 1.50 (s, 9H). MS (ESI) m/e 276.9 (M+H)$^+$.

Step 2

Following procedures of Example 29, the title compound was obtained.

t$_R$ (Conditions E)=5.8 min; 607.1 (M+H)$^+$. $^1$H NMR (CD$_3$OD, 300 MHz) δ 7.51 (d, J=9.9 Hz, 2H), 7.32 (s, 1H), 7.17-7.11 (m, 3H), 6.89 (dd, J=8.6, 2.3 Hz, 2H), 6.82-6.71 (m, 3H), 4.71 (dd, J=10.2, 2.6 Hz, 1H), 4.47-4.36 (m, 2H), 4.11-4.02 (m, 1H), 3.91-3.85 (m, 1H), 3.74-3.66 (m, 2H), 3.55-3.38 (m, 3H), 3.08 (t, J=7.2 Hz, 2H), 2.98-2.89 (m, 1H), 2.26 (s, 3H), 1.76-1.68 (m, 2H), 1.50-1.42 (m, 2H), 0.99 (t, J=7.4 Hz, 3H), 0.63 (t, J=7.4 Hz, 3H).

Example 36

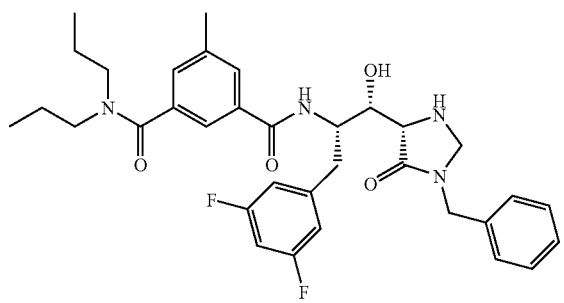

Step 1

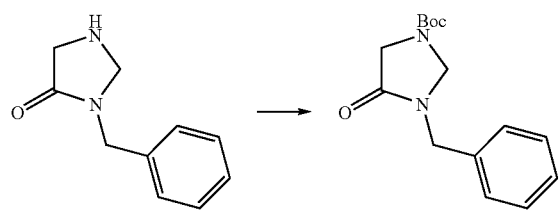

To a RT solution of 3-benzyl-4-imidazolidinone (1.07 g, 6.07 mmol), prepared according to Pinza, et al. *Liebigs Ann. Chem.* (1988), 993, in CH$_2$Cl$_2$ (80 ml) was added Et$_3$N (7 drops) and Boc$_2$O (1.39 g, 6.38 mmol). After 20 h at RT, the reaction mixture was diluted with water and stirred vigorously for 10 min. The phases were separated, and the aqueous phase was extracted with CH$_2$Cl$_2$ (2×). The organic portions were combined, washed with brine, dried over MgSO$_4$, filtered and concentrated. The crude residue was purified by chromatography (silica, 0-350% EtOAc/hexanes) to give the desired product (1.37 g, 4.96 mmol, 82%). LCMS (Conditions A) t$_R$=4.13 min; 277 (M+H)$^+$.

Step 2

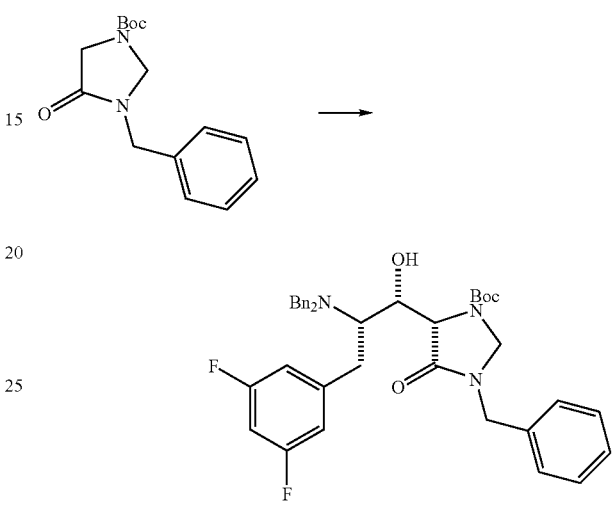

To a −78° C. solution of diisopropylamine (0.17 ml, 1.20 mmol) in THF (1 ml) was added n-BuLi (1.55 M in hexanes, 0.74 ml, 1.15 mmol). After 5 min, the mixture was warmed to 0° C., and after an additional 20 min, it was cooled back to −78° C. To this mixture was added a −78° C. solution of the product of Step 1 (304 mg, 1.10 mmol) in THF (3.5 ml). The resulting mixture was stirred at −78° C. for 1 h. At that time, a −78° C. solution of the product of Preparation 10 (366 mg, 1.00 mmol) in THF (2 ml) was added. The resulting mixture was stirred for 1.5 h at −78° C. and was then diluted with water and Et$_2$O. After warming to RT, the phases were separated, and the aqueous phase was extracted with Et$_2$O (3×). The organic portions were combined, washed with brine, dried over MgSO$_4$, filtered and concentrated. The crude residue was purified by chromatography (silica, 0→65% EtOAc/hexanes) to give the product (288 mg, 0.449 mmol, 45%). MS m/e 643 (M+H)$^+$.

Step 3

Using a procedure analogous to that of Example 29, Steps 4-6 (substituting 4 N HCl/dioxane for TFA in Step 6), the title compound was obtained. $^1$H NMR (300 MHz, CD$_3$OD) δ 7.63 (s, 1H), 7.48 (s, 1H), 7.31 (m, 6H), 6.89 (m, 2H), 6.76 (apparent tt, J=9.3, 2.4 Hz, 1H), 4.74 (m, 1H), 4.62 (br ABq, J$_{AB}$=6.9 Hz, Δν$_{AB}$=21.4 Hz, 2H), 4.44 (m, 4H), 3.45 (m, 2H), 3.35 (dd, unresolved, overlapping solvent peak, 1H), 3.16 (m, 2H), 2.97 (dd, J=15.0, 11.1 Hz, 1H), 2.41 (s, 3H), 1.70 (m, 2H), 1.50 (m, 2H), 0.98 (t, J=7.2 Hz, 3H), 0.67 (t, J=7.2 Hz, 3H); LCMS (Conditions A) t$_R$=4.69 min, 607 (M+H).

Example 36A

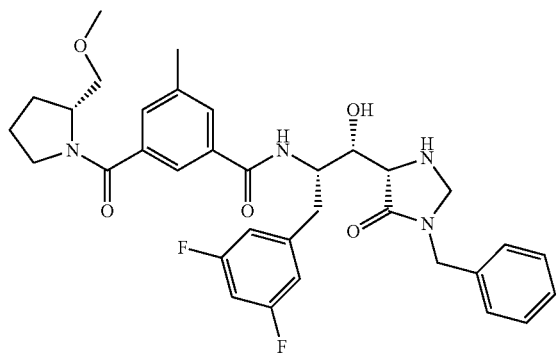

The product was prepared by essentially the same procedure as Example 36, substituting Preparation 3 for Preparation 1. LCMS (Conditions A) $t_R$=3.13 min, 621 (M+H).

Example 37

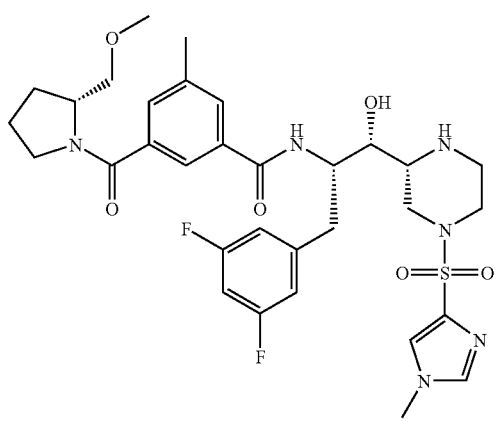

Step 1

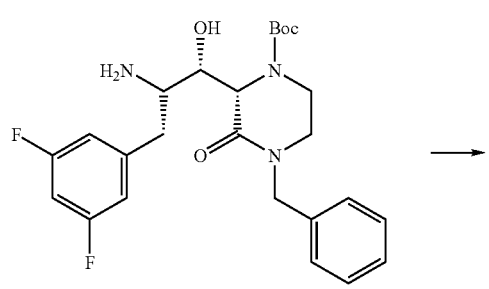

To a solution of the product of Example 29, Step 4 (326 mg, 0.687 mmol) in THF (3 ml) was added 2M $BH_3$—$SMe_2$ in THF (2.0 ml) and the mixture was heated to 60° C. for 16 h.

The mixture was treated with saturated citric acid (40 ml) and extracted with EtOAc (3×30 ml). The combined organic layers were concentrated and the residue partitioned between $CH_2Cl_2$ (60 ml) and aqueous $NH_4OH$ (20 ml). The organic layer was dried ($MgSO_4$) and concentrated to give the product (190 mg, 60%). MS m/e 462 (M+H)$^+$.

Step 2

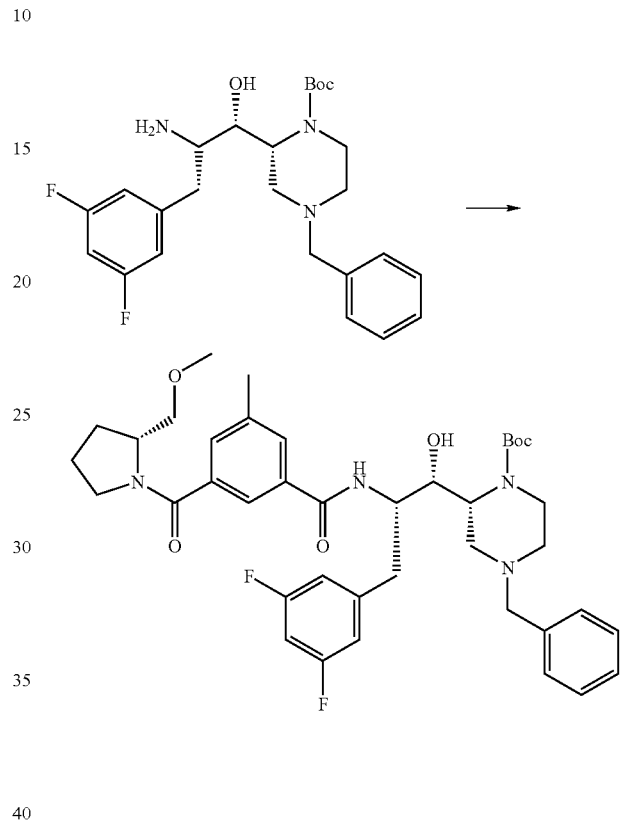

A mixture of the product of Step 1 (324 mg, 0.704 mmol), Preparation 3 (191 mg, 0.689 mmol), EDCI (135 mg, 0.704 mmol), HOBt (97 mg, 0.72 mmol), and $Et_3N$ (190 μl, 1.36 mmol) in $CH_2Cl_2$ (12 ml) was stirred at RT for 16 h. The mixture was diluted with $CH_2Cl_2$ (40 ml) and washed with 1N NaOH (20 ml). The organic layer was dried ($MgSO_4$), concentrated, and purified by PTLC (3% MeOH/$CH_2Cl_2$) to give the product (212 mg, 42%). MS m/e 721 (M+H)$^+$.

Step 3

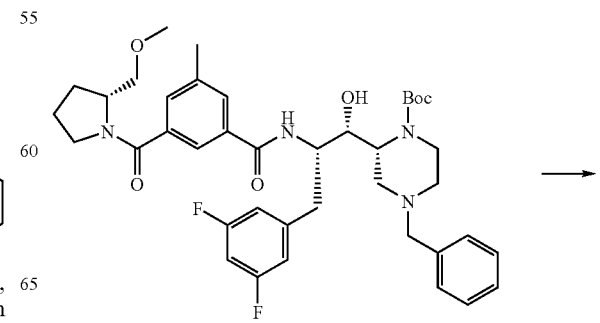

-continued

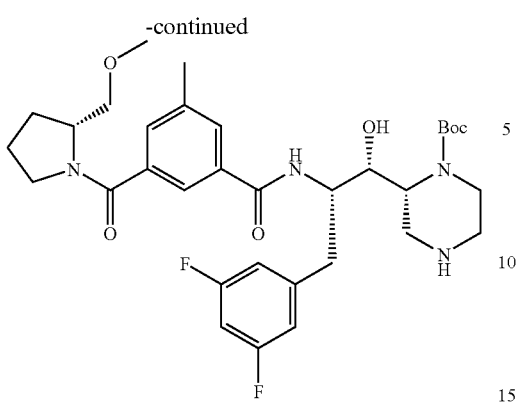

A mixture of the product of Step 2 (212 mg, 0.294 mmol), 20% Pd(OH)$_2$/C (230 mg), and catalytic amount of AcOH in EtOH (10 ml) was stirred under H$_2$ (1 atm) for 8 h at RT. The mixture was filtered through a pad of Celite and concentrated. The residue was taken up in CH$_2$Cl$_2$ (40 ml) and washed with 1N NaOH (20 ml). The organic layer was dried (MgSO$_4$) and concentrated to give the product (157 mg, 84%). MS m/e 631 (M+H)$^+$ Step 4

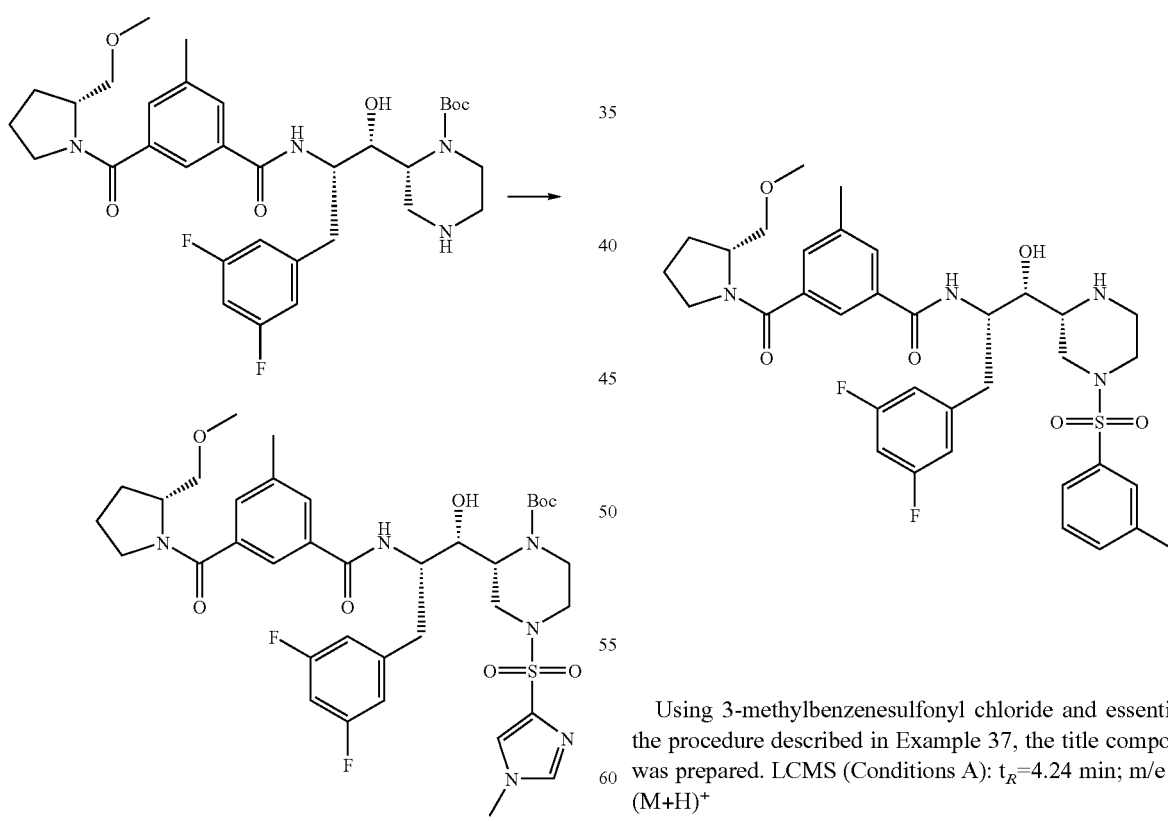

A mixture of the product of Step 3 (39 mg, 0.062 mmol), 1-methyl-1H-imidazole-4-sulfonyl chloride (12 mg, 0.066 mmol), and NEt$_3$ (20 µl, 0.14 mmol) in CH$_2$Cl$_2$ (5 ml) was stirred at RT for 16 h. The mixture was diluted with CH$_2$Cl$_2$ (40 ml) and washed with 1N NaOH (15 ml). The organic layer was dried (MgSO$_4$), concentrated, and purified by PTLC (5% MeOH/CH$_2$Cl$_2$) to give the product (34 mg, 71%). MS m/e 775 (M+H)$^+$ Step 5

A mixture of the product of Step 4 (34 mg, 0.044 mmol) and TFA (0.8 ml) in CH$_2$Cl$_2$ (5 ml) was stirred in an ice-water bath for 30 min, then at RT for 3 h. The mixture was diluted with CH$_2$Cl$_2$ (45 ml) and washed with aqueous NH$_4$OH (15 ml). The organic layer was dried (MgSO$_4$), concentrated, and purified by PTLC (7% MeOH/CH$_2$Cl$_2$) to give the product (26 mg, 87%). $^1$H NMR (CDCl$_3$, 400 MHz) δ 7.2-7.5 (m, 6H), 6.86 (m, 2H), 6.57 (m, 1H), 4.51 (m, 1H), 4.37 (m, 1H), 3.86 (m, 1H), 3.76 (m, 1H), 3.2-3.7 (m, 10H), 2.75-3.1 (m, 6H), 2.64 (m, 2H), 2.29 (s, 3H), 1.6-2.1 (m, 6H). LCMS (Conditions A): t$_R$=2.68 min; m/e 675 (M+H)$^+$ Example 37A Using 3-methylbenzenesulfonyl chloride and essentially the procedure described in Example 37, the title compound was prepared. LCMS (Conditions A): t$_R$=4.24 min; m/e 685 (M+H)$^+$ Using the appropriate sulfonyl chloride and Preparation 1 in place of Preparation 3, the following compounds were prepared by essentially the procedure outlined in Example 37.

| Example | Structure | LCMS (Conditions E) MH+; tR (min) |
|---|---|---|
| 37B | 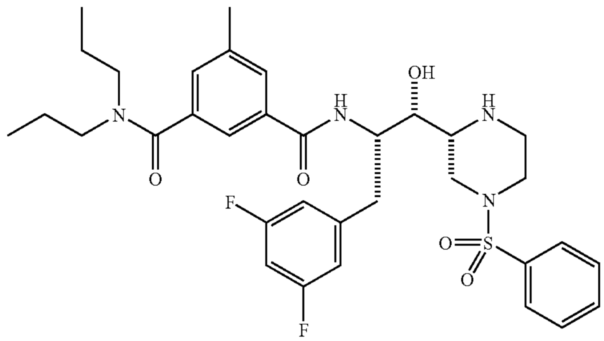 | 657.1<br>tR = 6.08 |
| 37C | 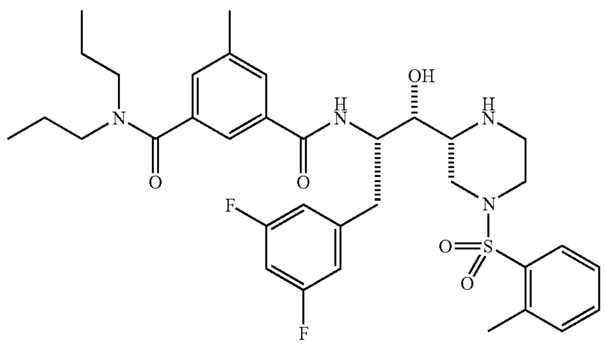 | 671.2<br>tR = 6.16 |
| 37D | 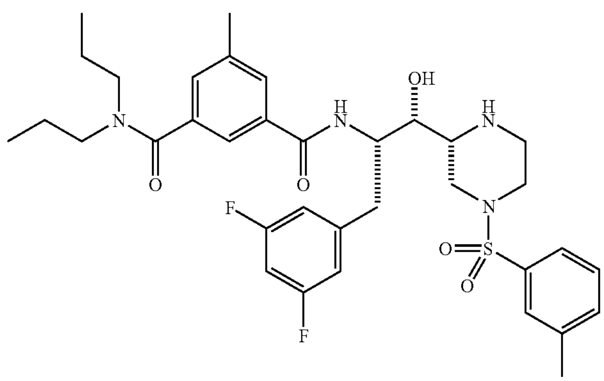 | 671.2<br>tR = 6.24 |
| 37E | 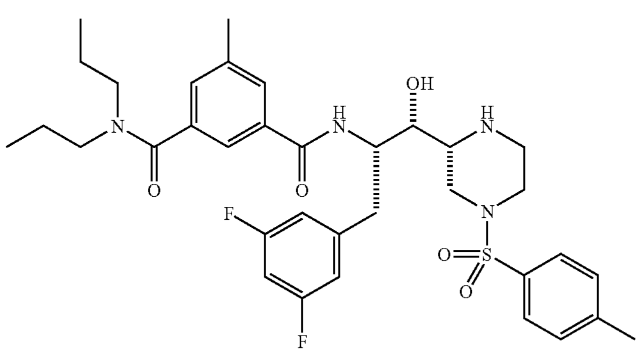 | 671.2<br>tR = 6.06 |

| Example | Structure | LCMS (Conditions E) MH⁺; $t_R$ (min) |
|---|---|---|
| 37F | 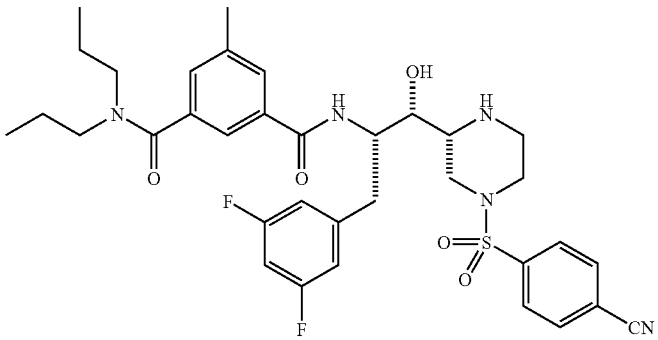 | 682.2<br>$t_R$ = 6.11 |
| 37G | 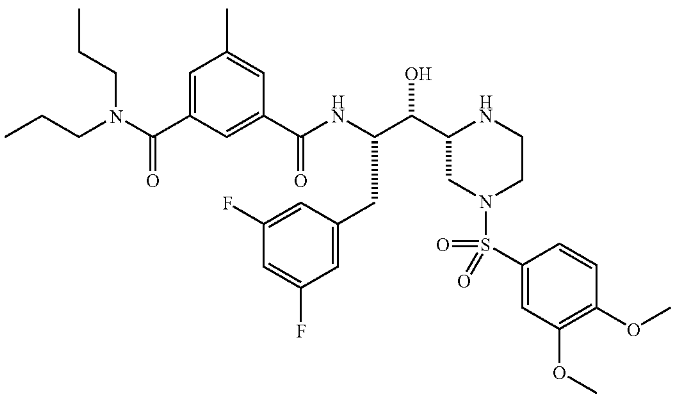 | 717.2<br>$t_R$ = 6.00 |
| 37H | 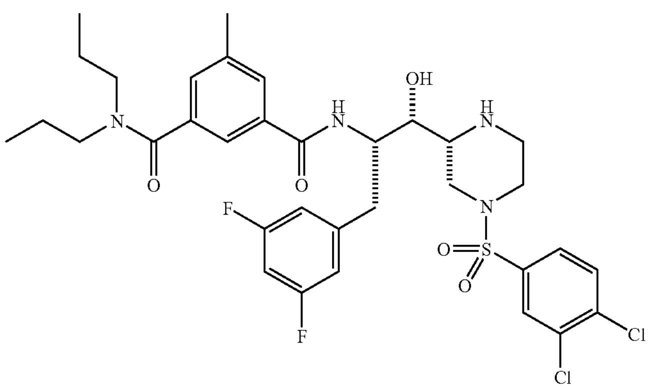 | 725.1<br>$t_R$ = 6.51 |
| 37I | 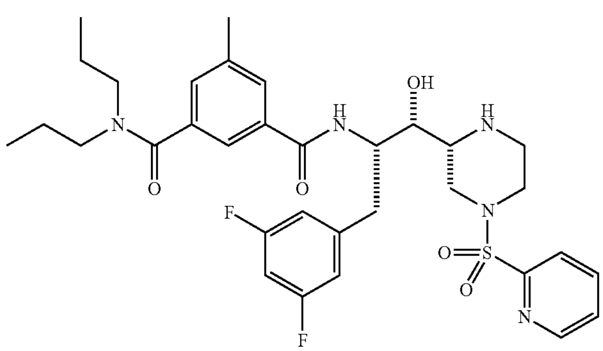 | 658.2<br>$t_R$ = 5.68 |

| Example | Structure | LCMS (Conditions E) MH⁺; $t_R$ (min) |
|---|---|---|
| 37J | 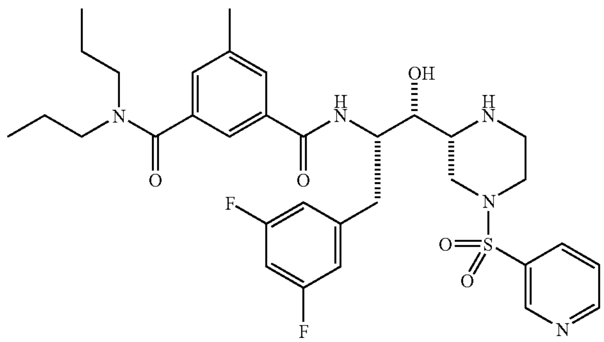 | 658.2 $t_R$ = 7.47 |
| 37K | 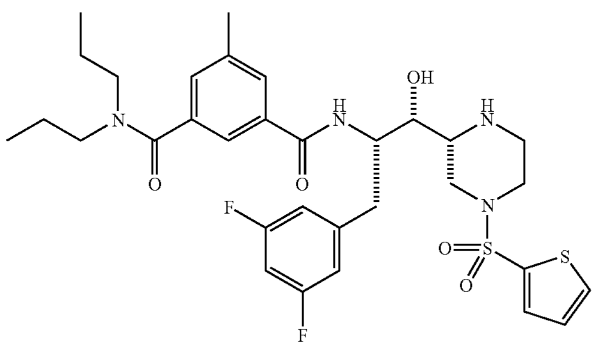 | 663.2 $t_R$ = 6.04 |
| 37L | 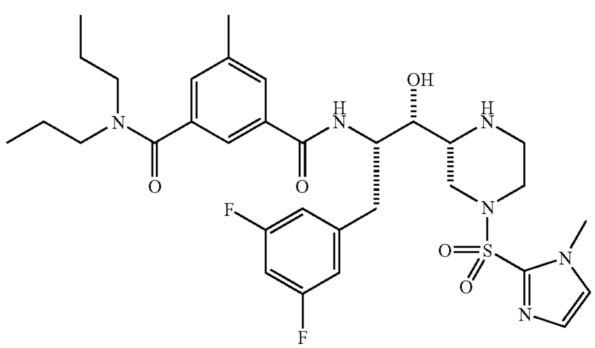 | 661.2 $t_R$ = 5.62 |
| 37M | 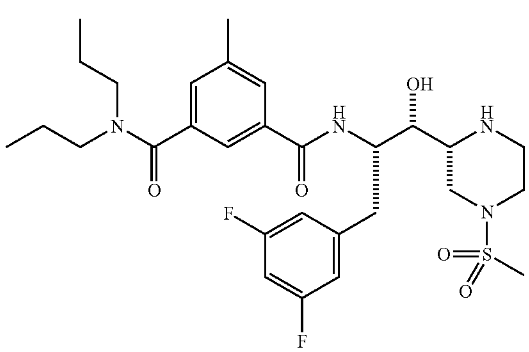 | 595.2 $t_R$ = 5.67 |

| Example | Structure | LCMS (Conditions E) MH+; $t_R$ (min) |
|---|---|---|
| 37N | 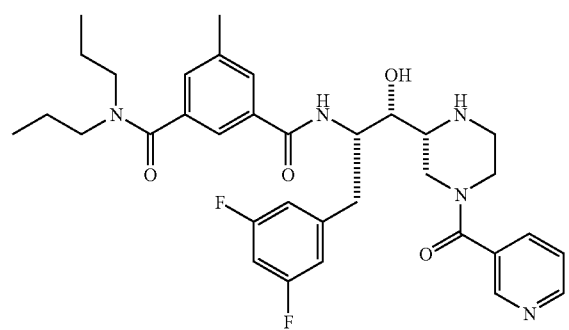 | 623.2<br>$t_R$ = 5.80 |
| 37O | 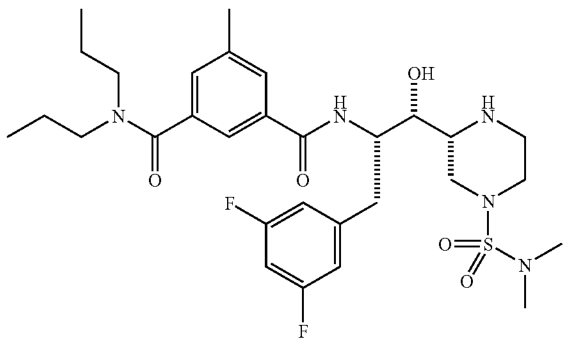 | 624.2<br>$t_R$ = 5.70 |

Example 38

Step 1

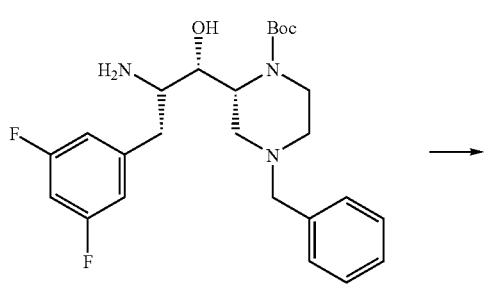

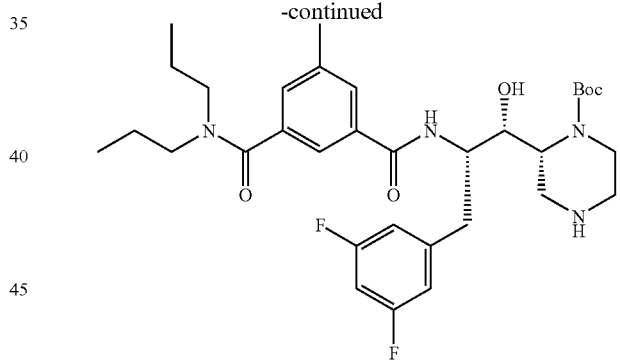

The product of Example 37, Step 1 was subjected to the sequence of reactions of Example 37, Steps 2 and 3, except that Preparation 1 was used in place of Preparation 3, to give the product.

Step 2

To a solution of the product of Step 1 (12 mg, 0.019 mmol) in $CH_2Cl_2$ (10 ml) was added nicotinoyl chloride hydrochloride (3.2 mg, 0.018 mmol) and DIEA (0.015 ml, 0.090 mmol). After stirring at RT for 16 h, the mixture was washed with water, dried ($MgSO_4$) and concentrated. PTLC of the residue (7:3 EtOAc/hexanes) gave the coupled product (2.6 mg, 20%). This product was treated with 3:7 $TFA/CH_2Cl_2$ (10 ml) at RT for 1 h, diluted with toluene (5 ml) and concentrated in vacuo. The residue was twice taken up in toluene and evaporated to remove residual TFA, to give the product. LCMS (Conditions E) $t_R$=5.16 min; 622.2 (M+H)+.

Using the appropriate acid chloride the following compounds were prepared:

| Example | Structure | LCMS (Conditions E) m/e MH+; $t_R$ (min) |
|---|---|---|
| 38A | 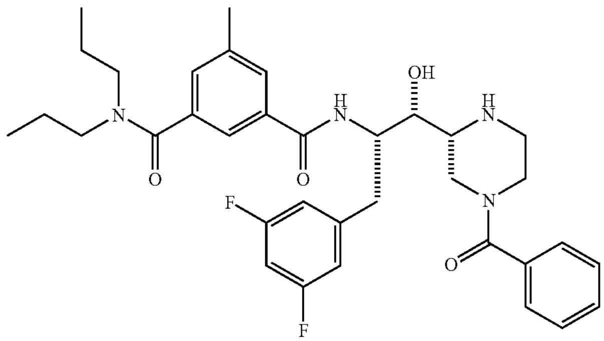 | 621.2 $t_R$ = 5.64 |
| 38B | 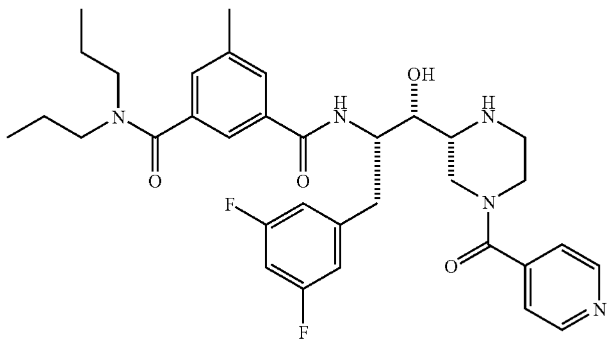 | 622.2 $t_R$ = 5.43 |
| 38C | 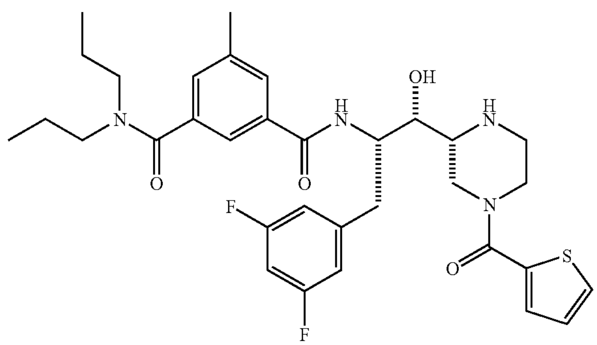 | 627.2 $t_R$ = 5.79 |
| 38D | 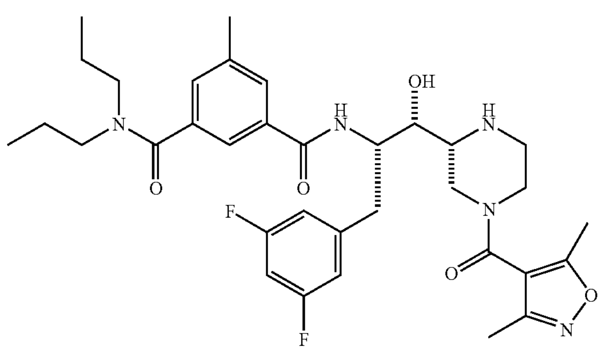 | 640.3 $t_R$ = 5.55 |

| Example | Structure | LCMS (Conditions E) m/e MH+; $t_R$ (min) |
|---|---|---|
| 38E | 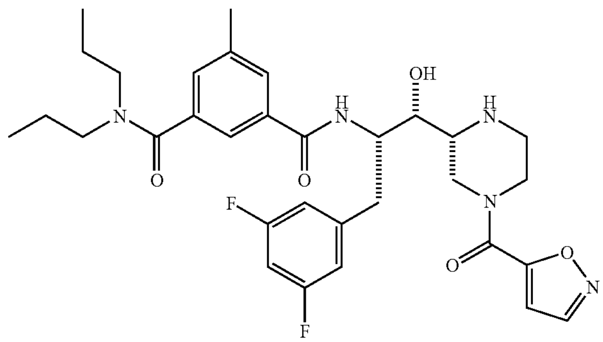 | 612.2<br>$t_R$ = 5.51 |
| 38F | 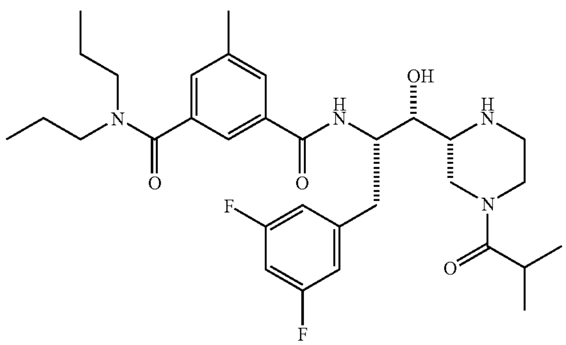 | 587.0<br>$t_R$ = 7.79 |
| 38G | 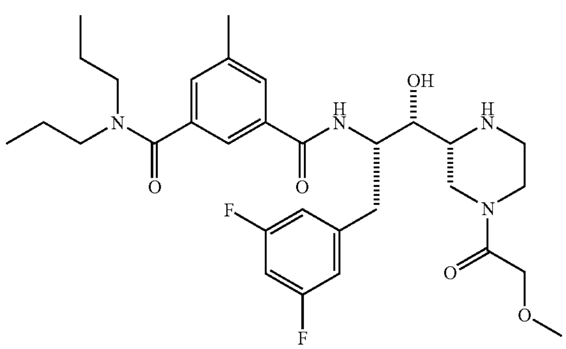 | 589.2<br>$t_R$ = 5.54 |
| 38H | 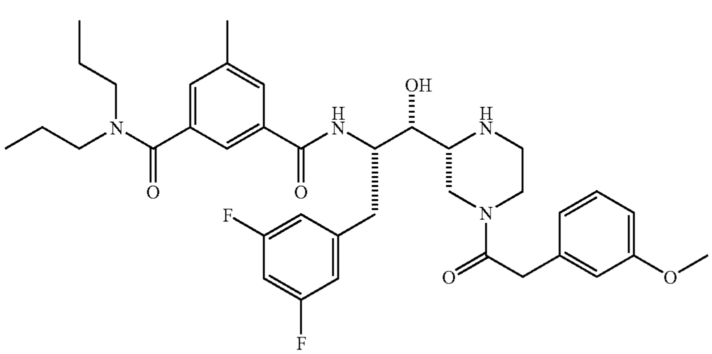 | 665.1<br>$t_R$ = 6.11 |

| Example | Structure | LCMS (Conditions E) m/e MH+; t_R (min) |
|---------|-----------|------------------------------------------|
| 38I | 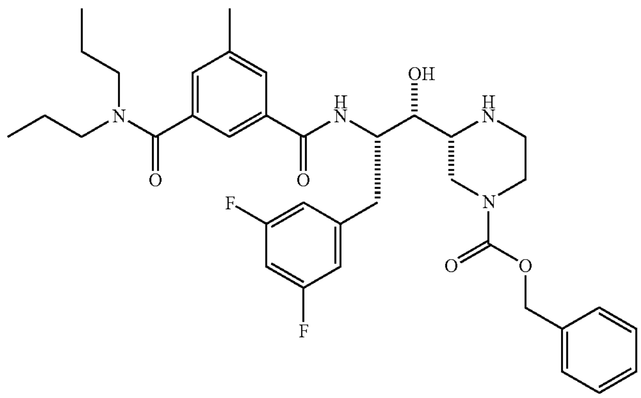 | 651.2 t_R = 6.13 |

Example 38J

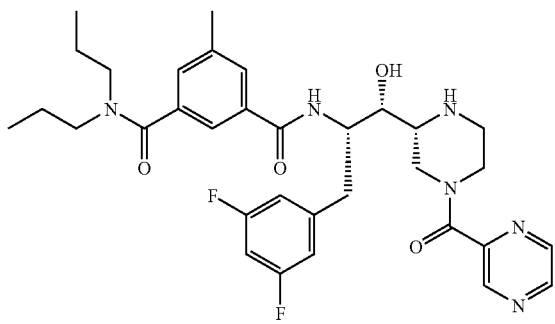

To a solution of Example 38, Step 1 (11 mg, 0.018 mmol) in $CH_2Cl_2$ (10 ml) was added pyrazine 2-carboxylic acid (3.1 mg, 0.025 mmol), EDC (6 mg, 0.031 mmol), HOBt (4 mg, 0.030 mmol), and DIEA (0.018 ml, 0.11 mmol). After stirring at RT for 16 h, the mixture was washed with $H_2O$, dried ($MgSO_4$) and concentrated. Silica gel chromatography of the residue (3:2 EtOAc/hexanes, then 1:9 MeOH/$CH_2Cl_2$) gave the coupled product (6 mg, 46%). This product was treated with 3:7 TFA/$CH_2Cl_2$ (10 ml) at RT for 1 h, diluted with toluene (5 ml) and concentrated in vacuo. The residue was twice taken up in toluene and evaporated to remove residual TFA, to give the product: LCMS (Conditions E) $t_R$=5.52 min; m/e 623.2 (M+H)+.

Using procedures known to those skilled in the art, the following Examples were prepared:

| Example | Structure | LCMS (Conditions E) m/e MH+; t_R (min) |
|---------|-----------|------------------------------------------|
| 38K | 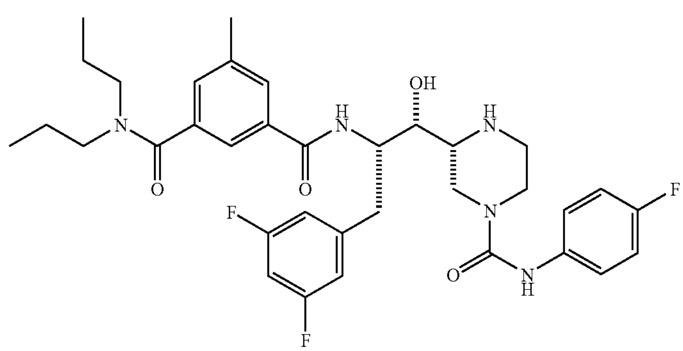 | 654.1 t_R = 6.26 |

-continued

| Example | Structure | LCMS (Conditions E) m/e MH⁺; t$_R$ (min) |
|---|---|---|
| 38L | 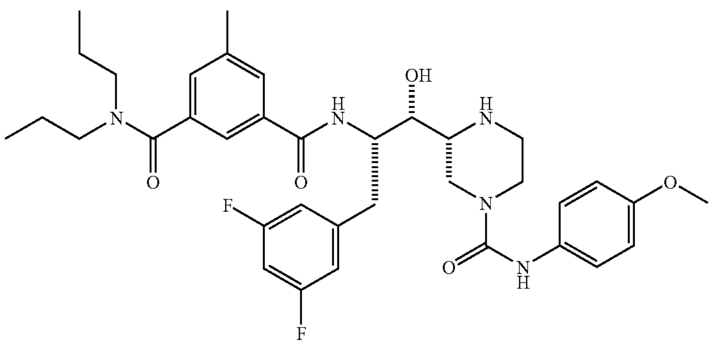 | 666.2 t$_R$ = 6.06 |
| 38M | 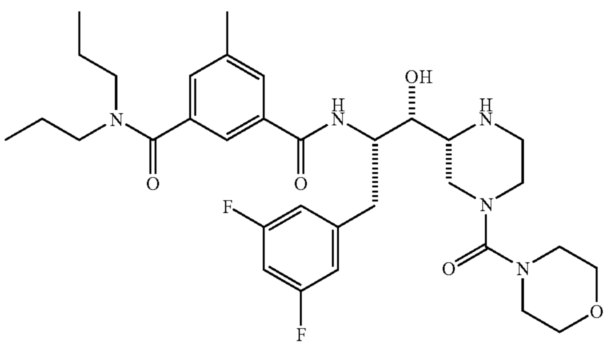 | 630.3 t$_R$ = 5.56 |
| 38N | 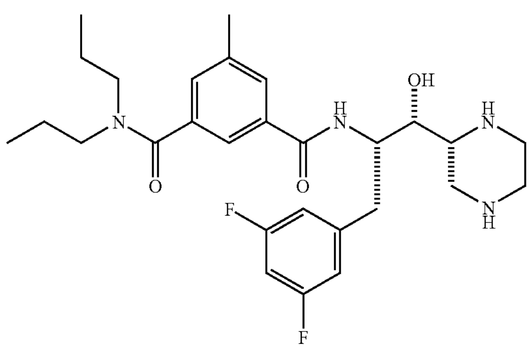 | 517.2 tR = 5.07 |
| 38O | 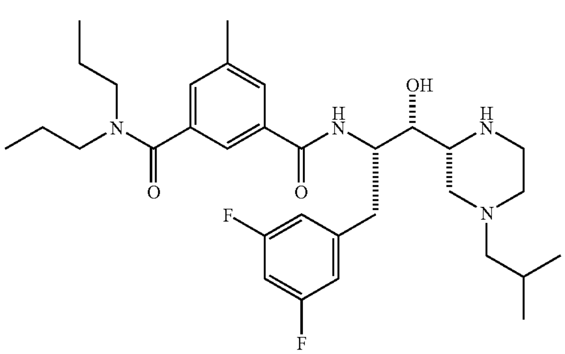 | 573.2 tR = 5.49 |

| Example | Structure | LCMS (Conditions E) m/e MH+; $t_R$ (min) |
|---|---|---|
| 38P | 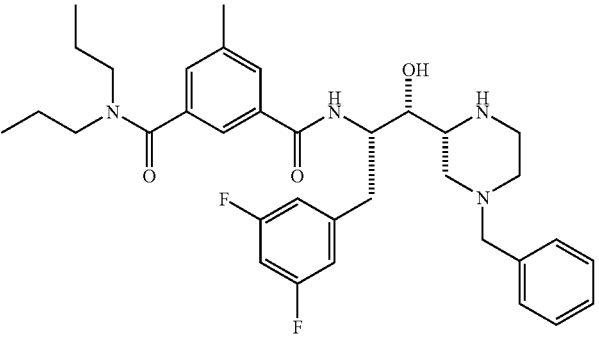 | 607.2 tR = 5.46 |

Example 39

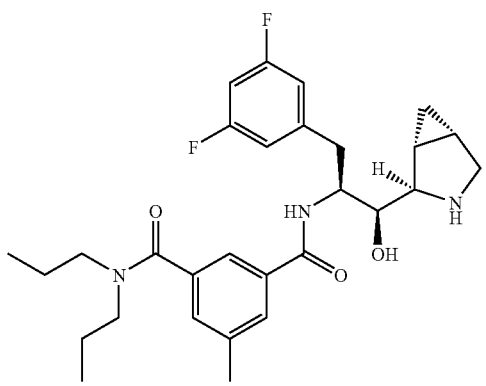

Step 1

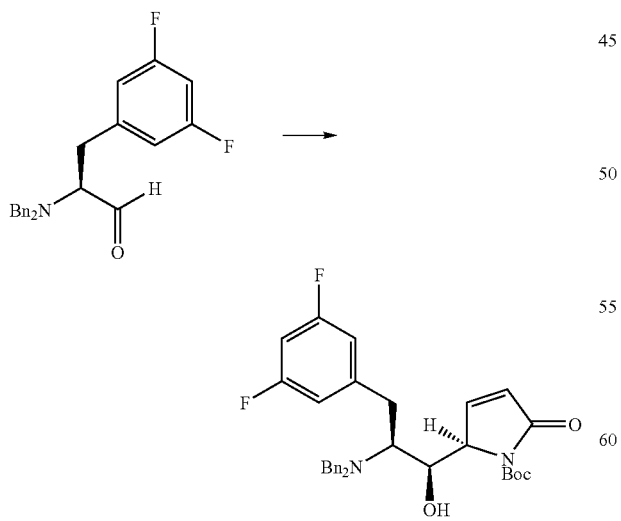

A solution of Preparation 10 (395 mg, 1.08 mmol) in Et₂O (5 ml) was cooled to −78° C., and borontrifluoride-etherate (270 μl, 2.15 mmol) was added. After adding N-Boc-2-tert-butyldimethylsiloxypyrrole (Tian, et al., *J. Org. Proc. Res. Dev.* (2002), 6, 416-418) (960 mg, 3.24 mmol), the reaction was stirred for 4 h at −78° C., diluted at −78° C. with sat. aq. NaHCO₃ (5 ml) and warmed to 23° C. The mixture was diluted with Et₂O, and the organic layer washed with NaHCO₃ (2×), water (1×) and brine (1×), followed by drying over MgSO₄ and concentration in vacuo. The residue was purified by chromatography over silica gel (5→50% EtOAc/hexanes) to give the product as a single diastereomer (228 mg, 416 μmol, 39%). ¹H NMR (400 MHz, CDCl₃) δ=7.28-7.16 (m, 10H), 6.81 (m, 2H), 6.65 (m, 1H), 5.90 (m, 1H), 5.84 (m, 1H), 5.32 (m, 1H), 4.58 (m, 1H), 3.78 (d, J=13.2 Hz, 2H), 3.42 (d, J=13.2 Hz, 2H), 3.12 (m, 1H), 2.96 (m, 2H), 2.10 (bs, 1H), 1.42 (s, 9H).

Step 2

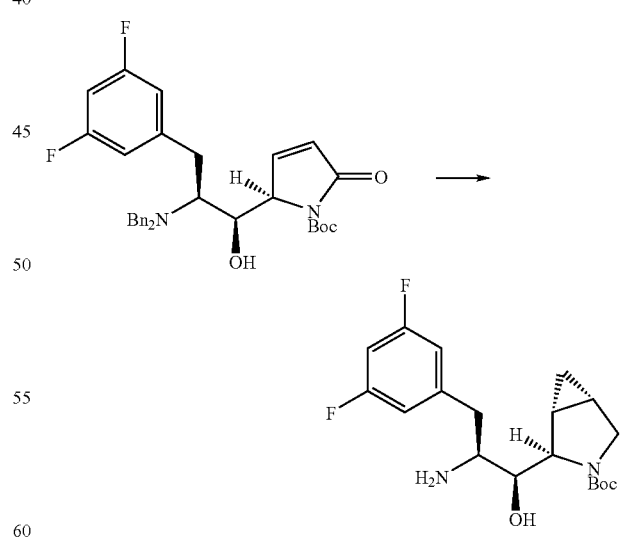

To a solution of the product of Step 1 (100 mg, 180 μmol) in Et₂O (3 ml) at 23° C. was added Pd(OAc)₂ (10 mg, 44 μmol) and diazomethane (~2 mmol in 7 ml Et₂O). After the initial foaming subsided, the reaction was stirred for 18 h at 23° C. After filtration, the filtrate was concentrated, then subjected to reverse-phase HPLC (Conditions D, 15 min ramp) to give the cyclopropane intermediate (67 mg, 120 μmol, 66%); LCMS (Conditions B): $t_R$=3.71 min, m/e 563 (M+H)⁺; 463 (M−Boc+H)⁺. The above intermediate (67 mg, 120 μmol) was dissolved in THF (1.5 ml), and BH₃-THF (500 μl of 1 M solution, 500 μmol) was added at 23° C. After the gas evolution subsided, the reaction was heated at 72° C. for 60 min, cooled to 23° C., diluted with Et₂O and quenched with sat. NH₄Cl solution. The organic layer was washed with 5% aq. citric acid (1×), water (2×) and brine (1×), then dried over MgSO₄ and concentrated under reduced pressure to give the cyclopropanated pyrrolidine (92 mg, 109 μmol, 92%); LCMS (Conditions B): $t_R$=3.38 min, m/e 549 (M+H)⁺. To a solution of the cyclopropanated pyrrolidine (92 mg, 109 μmol) in MeOH (4 ml) at 23° C. was added palladium(II) hydroxide on carbon (20%, 50 mg). The reaction mixture was stirred under an atmosphere of H₂ (1 atm) for 6 h at 23° C., followed by filtration through a plug of celite. Concentration in vacuo afforded the product (40.5 mg, 110 μmol, 100%), which was directly used in the next step.

Step 3

To EDC-resin (216 mg, 330 μmol at 1.53 mmol/g loading) was added a solution of the product of Step 2 (40.5 mg, 110 μmol in 2 ml THF/CH₃CN, 1:1 v/v), followed by a solution of HOBt (27 mg, 180 μmol) and Preparation 1 (35 mg, 130 μmol) in 4 ml THF/CH₃CN, 1:1 v/v). After gently shaking the reaction for 18 h at 23° C., PS-trisamine resin (Argonaut Technologies, 195 mg, 660 μmol at 3.38 mmol/g loading) and PS-NCO resin (Argonaut Technologies, 224 mg, 330 μmol at 1.47 mmol/g loading) were added. After 6 h of further shaking, the reactions were filtered, the resin washed with THF (2×1 ml), and the volatiles removed under vacuum. The residue was purified by reverse-phase HPLC (Conditions D, 15 min ramp) to give the intermediate Boc-protected amide (24.8 mg, 40 μmol, 37%). LCMS (Conditions A): $t_R$=4.98 min, m/e 614 (M+H)⁺, 558 (M−tBu+H)⁺ and 514 (M−Boc+H)⁺. The amide (20 mg, 32 μmol) was deprotected using 20% TFA/CH₂Cl₂ (3 ml) for 6 h at 23° C., followed by removal of the volatiles under vacuum. The resulting residue was exposed to 1 M HCl/MeOH (300 μL) for 30 min at 23° C., then concentrated under vacuum to give the product (17.5 mg, 32 μmol, 100%). LCMS (Conditions A): $t_R$=4.26 min, m/e 514 (M+H−HCl)⁺.

Example 40

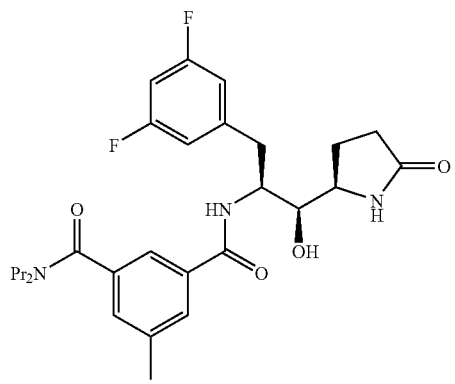

Step 1

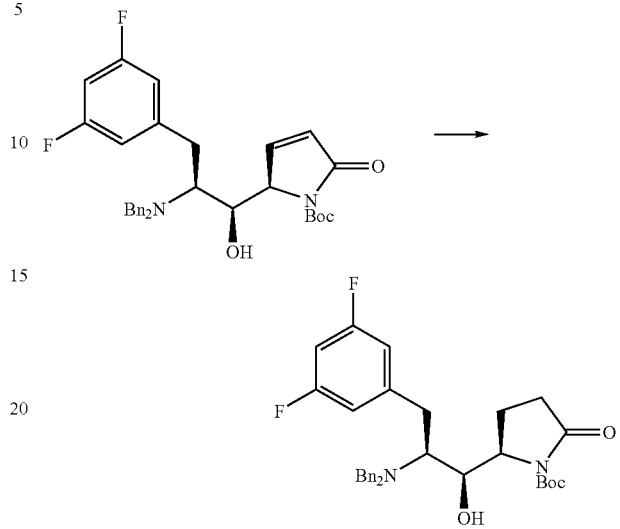

To a solution of the product from Example 39, Step 1 (111 mg, 0.2 mmol) in MeOH (1.5 ml) at 0° C. was carefully added NiCl₂-6H₂O (17 mg, 0.07 mmol) and NaBH₄ (8 mg, 0.2 mmol). After 90 min, the reaction mixture was diluted with sat. NH₄Cl and CH₂Cl₂. The aqueous layer was twice extracted with CH₂Cl₂, and the combined organic layers were dried (MgSO₄), concentrated and directly taken into the next step.

Step 2

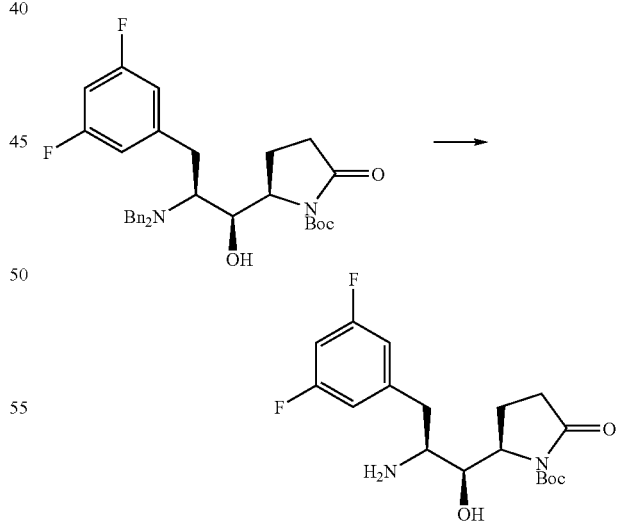

The product from step 1 (104 mg, 0.18 mmol) was stirred with 20% Pd(OH)₂/carbon (75 mg) in MeOH (3 ml) under a 50 psi atmosphere of H₂ at RT until TLC indicated the completion of the reaction. After filtering the reaction mixture over celite, the filtrate was concentrated to give the desired product in quantitative yield.

Step 3

The product of Step 2 and Preparation 1 were coupled and the resultant product deprotected in analogy to the method of Example 2, Step 6 to give the product. LCMS (Conditions A) 4.13 min: 516 (M+H)+

Example 41

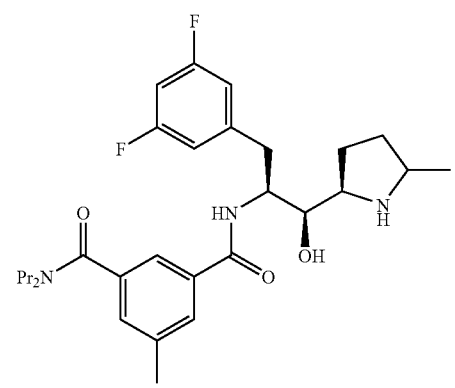

Step 1

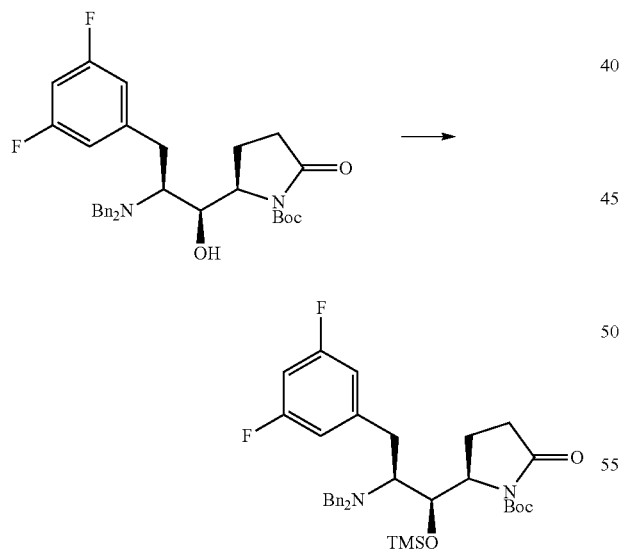

TMSCl (1.14 ml, 8.96 mmol) was added to a solution of the product from Example 39, step 1 (1.23 g, 2.24 mmol) in pyridine (10 ml) at 0° C. After 6 h, the reaction mixture was diluted with water and CH$_2$Cl$_2$. The aqueous layer was twice extracted with CH$_2$Cl$_2$, and the combined organic layers were dried (MgSO$_4$), concentrated and directly taken into the next step.

Step 2

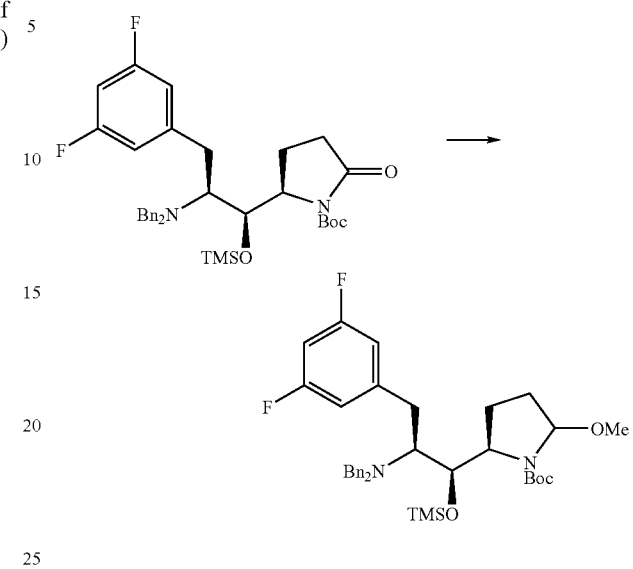

Step 2 and Step 3 of Example 41 were adapted from Hanessian et. al (*J. Org. Chem.* (2002), 4261-4274). DIBAL (1 M in toluene, 0.46 ml, 0.46 mmol) was added to a solution of the product from step 1 (145 mg, 0.23 mmol) in THF (2 ml) at −78° C. After 2.5 h, the reaction mixture was diluted with water, stirred for 40 min and concentrated. The residue was redissolved in 3 M NaOH, extracted with EtOAc (3×), and the organic layer dried (MgSO$_4$) and concentrated. The residue was treated with a catalytic amount of pTSA in MeOH at RT for 18 h, then concentrated. The residue was redissolved in EtOAc, washed with sat. NaHCO$_3$, and the organic layer was dried (MgSO$_4$), concentrated and directly taken into the next step.

Step 3

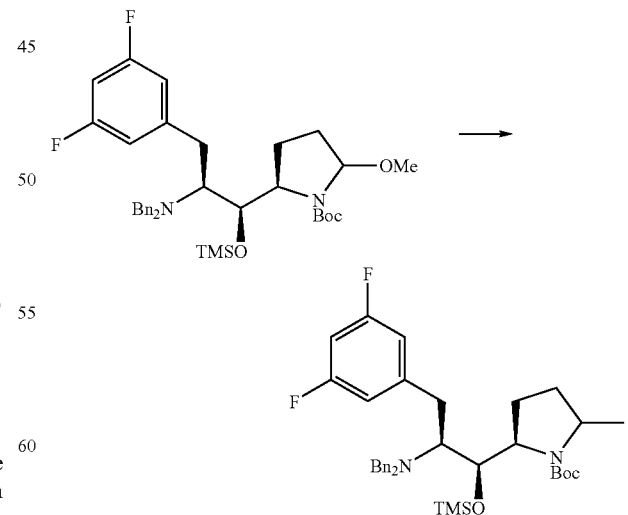

MeMgBr (1.4 M in THF, 0.67 ml, 0.93 mmol) was added to a suspension of CuBr-DMS (196 mg, 0.93 mmol) in THF (3 ml) at −40° C. After 60 min at −30° C., the yellow solution was cooled to −78° C., and BF$_3$—OEt$_2$ (0.115 ml, 0.93 mmol) was added. After 30 min, a solution of the product from step 2 (160 mg, 0.23 mmol) in THF (1.5 ml) was added, and the reaction was warmed to RT over 2 h. After an additional hour at RT, the reaction was diluted with sat. NH$_4$Cl/NH$_4$OH (pH 7) and Et$_2$O. Following extraction of the aqueous layer with Et$_2$O, the organic layers were washed (1×NH$_4$Cl, 1× water, 1× brine), dried (MgSO$_4$) and concentrated. The residue was subjected to reverse-phase HPLC (Conditions C) to give the desired product [LCMS (Conditions B: 4.71 min, 623 (M+H)$^+$], along with material without the TMS-protecting group [LCMS (Conditions B: 3.49 min; 551 (M+H)$^+$].

Step 4

The product from step 3 was converted into Example 41 by essentially the same procedures set forth in Example 40, step 2 and 3. LCMS (Conditions A) 4.62 min; 516 (M+H)$^+$ Example 42

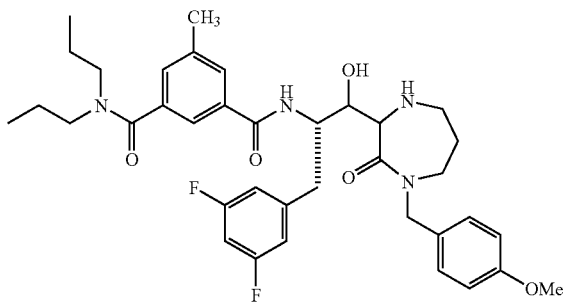

Step 1

To a solution of trifluoromethanesulfonic anhydride (22 ml, 131 mmol, 2 eq) in CH$_2$Cl$_2$ (100 ml) at 0° C. and was added dropwise a solution of 1,3-propanediol (5.0 g, 66 mmol, 1 eq) and pyridine (10.6 g, 131 mmol, 2 eq) in CH$_2$Cl$_2$ (100 ml) over 1 h. The precipitate formed was filtered off and the filtrate was washed with H$_2$O (3×100 ml), dried (MgSO$_4$), and concentrated in vacuo. The residue was chromatographed on silica gel by eluting with 70% EtOAc/hexanes to give the product (13.34 g, 61%) as a brown oil. $^1$H NMR (CDCl$_3$, 300 MHz) δ 4.67 (t, 4H), 2.36 (m, 2H).

Step 2

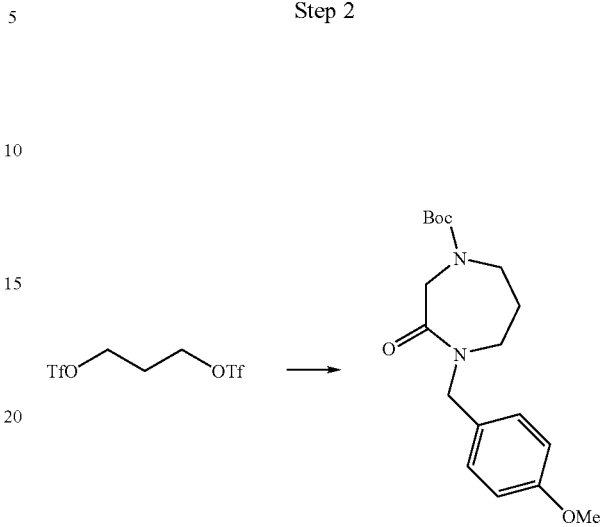

To a suspension of NaH (1.03 g, 11.8 mmol, 60% suspension in mineral oil) in Et$_2$O (20 ml) was added the product of Step 1 (3.46 g, 11.76 mmol, 1 eq) in Et$_2$O (20 ml). The reaction mixture was stirred at 0° C. for 30 min. Then a solution of [(4-methoxybenzylcarbamoyl)methyl]carbamic acid tert-butyl ester (4.0 g, 11.8 mmol, 1 eq) was added dropwise to the reaction mixture while the reaction temperature was kept at 0° C. After the mixture was stirred at RT for 1 h, a second portion of NaH (1.44 g, 16.44 mmol, 1.4 eq) was added and the reaction mixture was stirred at RT for 2 d. The reaction mixture was poured into a 1:1 mixture of 1N HC/and ice water (15 ml). The aqueous phase was extracted with Et$_2$O (3×100 ml). The organic layers were combined, dried (MgSO$_4$), and concentrated in vacuo. The residue was chromatographed (SiO$_2$, 5% MeOH/CH$_2$Cl$_2$) to give the product (1.5 g, 40%) as a yellow oil. $^1$H NMR (CDCl$_3$, 300 MHz) δ 7.18 (d, 2H), 6.83 (d, 2H), 4.50 (s, 2H), 4.13 (m, 2H), 3.78 (s, 3H), 3.49 (m, 2H), 3.30 (m, 2H), 1.68 (m, 2H), 1.47 (s, 9H).

Step 3

The product of Step 2 was condensed with Preparation 9 by essentially the procedure of Example 33, Step 1. The resultant product was subjected to the procedure of Example 33, Step 4. After purification (SiO$_2$, 80% EtOAc/hexanes then 10% MeOH/EtOAc) the product was obtained. $^1$H NMR (CDCl$_3$, 300 MHz) δ 7.54 (s, 1H), 7.41 (s, 1H), 7.24 (m, 2H), 7.11 (m, 2H), 6.82-6.25 (m, 3H), 6.59 (t, 1H), 4.76 (m, 1H), 4.57 (m, 2H), 3.92 (t, 1H), 3.79 (s, 3H), 3.51 (m, 3H), 3.26 (m, 3H), 2.99 (m, 1H), 2.47 (s, 3H), 1.69 (m, 2H), 1.84 (m, 2H), 1.50 (m, 2H), 0.99 (t, 3H), 0.85 (m, 3H). MS (ESI): MH$^+$=665.2.

Using the appropriate starting materials and essentially the same procedure the following Examples were prepared:

| Example | Structure | LCMS (Conditions E) m/e MH⁺; $t_R$ (min) |
|---|---|---|
| 42A | 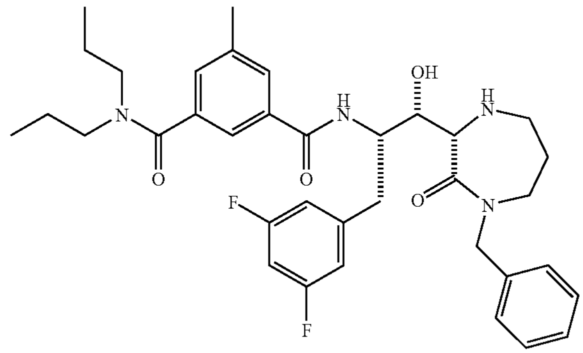 | 635.3 $t_R = 6.22$ |
| 42B | 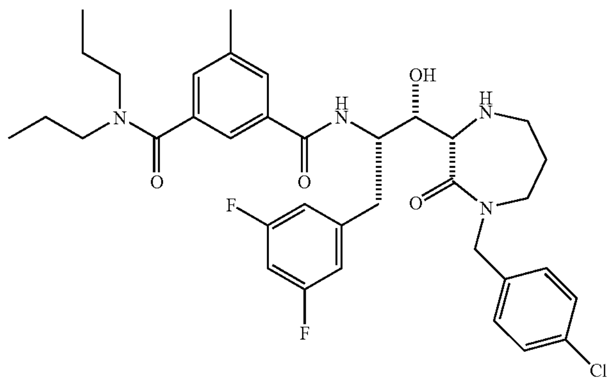 | 669.2 $t_R = 6.44$ |

BACE-1 Cloning, Protein Expression and Purification

A predicted soluble form of human BACE1 (sBACE1, corresponding to amino acids 1-454) was generated from the full length BACE1 cDNA (full length human BACE1 cDNA in pCDNA4/mycHisA construct; University of Toronto) by PCR using the advantage-GC cDNA PCR kit (Clontech, Palo Alto, Calif.). A HindIII/PmeI fragment from pcDNA4-sBACE1myc/His was blunt ended using Klenow and subcloned into the Stu I site of pFASTBACI(A) (Invitrogen). A sBACE1mycHis recombinant bacmid was generated by transposition in DH10Bac cells (GIBCO/BRL). Subsequently, the sBACE1mycHis bacmid construct was transfected into sf9 cells using CellFectin (Invitrogen, San Diego, Calif.) in order to generate recombinant baculovirus. Sf9 cells were grown in SF 900-II medium (Invitrogen) supplemented with 3% heat inactivated FBS and 0.5× penicillin/streptomycin solution (Invitrogen). Five milliliters of high titer plaque purified sBACEmyc/His virus was used to infect 1 L of logarithmically growing sf9 cells for 72 hours. Intact cells were pelleted by centrifugation at 3000×g for 15 minutes. The supernatant, containing secreted sBACE1, was collected and diluted 50% v/v with 100 mM HEPES, pH 8.0. The diluted medium was loaded onto a Q-sepharose column. The Q-sepharose column was washed with Buffer A (20 mM HEPES, pH 8.0, 50 mM NaCl).

Proteins, were eluted from the Q-sepharose column with Buffer B (20 mM HEPES, pH 8.0, 500 mM NaCl). The protein peaks from the Q-sepharose column were pooled and loaded onto a Ni-NTA agarose column. The Ni-NTA column was then washed with Buffer C (20 mM HEPES, pH 8.0, 500 mM NaCl). Bound proteins were then eluted with Buffer D (Buffer C+250 mM imidazole). Peak protein fractions as determined by the Bradford Assay (Biorad, Calif.) were concentrated using a Centricon 30 concentrator (Millipore). sBACE1 purity was estimated to be ~90% as assessed by SDS-PAGE and Commassie Blue staining. N-terminal sequencing indicated that greater than 90% of the purified sBACE1 contained the prodomain; hence this protein is referred to as sproBACE1.

Peptide Hydrolysis Assay

The inhibitor, 25 nM EuK-biotin labeled APPsw substrate (EuK-KTEEISEVNLDAEFRHDKC-biotin; CIS-Bio International, France), 5 µM unlabeled APPsw peptide (KTEEISEVNLDAEFRHDK; American Peptide Company, Sunnyvale, Calif.), 7 nM sproBACE1, 20 mM PIPES pH 5.0, 0.1% Brij-35 (protein grade, Calbiochem, San Diego, Calif.), and 10% glycerol were preincubated for 30 min at 30° C. Reactions were initiated by addition of substrate in a 5 µl aliquot resulting in a total volume of 25 µl. After 3 hr at 30° C. reactions were terminated by addition of an equal volume of 2× stop buffer containing 50 mM Tris-HCl pH 8.0, 0.5 M KF, 0.001% Brij-35, 20 µg/ml SA-XL665 (cross-linked allophycocyanin protein coupled to streptavidin; CIS-Bio International, France) (0.5 µg/well). Plates were shaken briefly and spun at 1200×g for 10 seconds to pellet all liquid to the bottom of the plate before the incubation. HTRF measurements were made on a Packard Discovery® HTRF plate reader using 337 nm laser light to excite the sample followed by a 50 µs delay and simultaneous measurements of both 620 nm and 665 nm emissions for 400 µs.

$IC_{50}$ determinations for inhibitors, (I), were determined by measuring the percent change of the relative fluorescence at 665 nm divided by the relative fluorescence at 620 nm, (665/620 ratio), in the presence of varying concentrations of I and a fixed concentration of enzyme and substrate. Nonlinear regression analysis of this data was performed using GraphPad Prism 3.0 software selecting four parameter logistic equation, that allows for a variable slope. Y=Bottom+(Top−Bottom)/(1+10^((LogEC50−X)*Hill Slope)); X is the logarithm of concentration of I, Y is the percent change in ratio and Y starts at bottom and goes to top with a sigmoid shape.

Compounds of the present invention have an $IC_{50}$ range from about 0.1 to about 30,000 nM, preferably about 0.1 to about 1000 nM, more preferably about 0.1 to about 100 nM. Compounds of the preferred stereochemistry have $IC_{50}$ values in a range of about 0.1 to about 500 nM, preferably about 0.1 to about 100 nM. Example 29D has an $IC_{50}$ of 1.4 nM.

For preparing pharmaceutical compositions from the compounds described by this invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g. magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), Remington's Pharmaceutical Sciences, 18th Edition, (1990), Mack Publishing Co., Easton, Pa.

Liquid form preparations include solutions, suspensions and emulsions. As an example may be mentioned water or water-propylene glycol solutions for parenteral injection or addition of sweeteners and ° pacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations which are intended to be converted, shortly before use, to liquid form preparations for either oral or parenteral administration. Such liquid forms include solutions, suspensions and emulsions.

The compounds of the invention may also be deliverable transdermally. The transdermal compositions can take the form of creams, lotions, aerosols and/or emulsions and can be included in a transdermal patch of the matrix or reservoir type as are conventional in the art for this purpose.

Preferably the compound is administered orally.

Preferably, the pharmaceutical preparation is in a unit dosage form. In such form, the preparation is subdivided into suitably sized unit doses containing appropriate quantities of the active component, e.g., an effective amount to achieve the desired purpose.

The quantity of active compound in a unit dose of preparation may be varied or adjusted from about 1 mg to about 100 mg, preferably from about 1 mg to about 50 mg, more preferably from about 1 mg to about 25 mg, according to the particular application.

The actual dosage employed may be varied depending upon the requirements of the patient and the severity of the condition being treated. Determination of the proper dosage regimen for a particular situation is within the skill of the art. For convenience, the total daily dosage may be divided and administered in portions during the day as required.

The amount and frequency of administration of the compounds of the invention and/or the pharmaceutically acceptable salts thereof will be regulated according to the judgment of the attending clinician considering such factors as age, condition and size of the patient as well as severity of the symptoms being treated. A typical recommended daily dosage regimen for oral administration can range from about 1 mg/day to about 300 mg/day, preferably 1 mg/day to 50 mg/day, in two to four divided doses.

When a compound of formula I is used in combination with a β-secretase inhibitors other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody to treat a cognitive disorder or neurodegenerative disorder, the active components may be co-administered simultaneously or sequentially, or a single pharmaceutical composition comprising a compound of formula I and one of the other agents in a pharmaceutically acceptable carrier can be administered. The components of the combination can be administered individually or together in any conventional oral or parenteral dosage form such as capsule, tablet, powder, cachet, suspension, solution, suppository, nasal spray, etc. The dosage of the β-secretase inhibitors other than those of formula I, HMG-CoA reductase inhibitor, gamma-secretase inhibitor, non-steroidal anti-inflammatory agent, N-methyl-D-aspartate receptor antagonist, cholinesterase inhibitor or anti-amyloid antibody can be determined from published material, and may range from 0.001 to 100 mg/kg body weight.

When separate pharmaceutical compositions of a compound of formula I and a β-secretase inhibitors other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody are to be administered, they can be provided in a kit comprising in a single package, one container comprising a compound of formula I in a pharmaceutically acceptable carrier, and a separate container comprising the other agent in a pharmaceutically acceptable carrier, with the compound of formula I and the other agent being present in amounts such that the combination is therapeutically effective. A kit is advantageous for administering a combination when, for example, the components must be administered at different time intervals or when they are in different dosage forms.

The invention also includes multi-agent compositions, kits and methods of treatment, e.g., a compound of formula I can be administered in combination with an HMG-CoA reductase inhibitor and a non-steroidal anti-inflammatory agent.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:
1. A compound having the structural formula

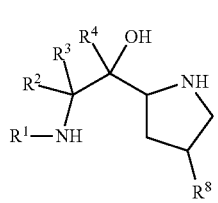
(I)

or a pharmaceutically acceptable salt thereof, wherein
R¹ is

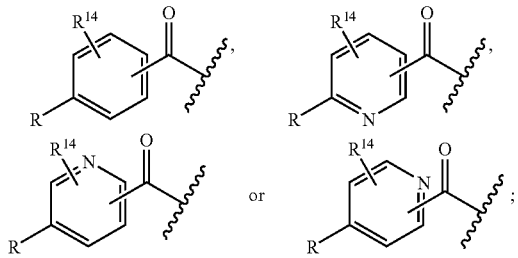

R is —C(O)—N(R²⁷)(R²⁸);
R² is difluorobenzyl;
R³ is H or alkyl;
R⁴ is H or alkyl;
R⁸ is selected from the group consisting of H, OH, alkoxy, phenoxy or benzyloxy, wherein said alkoxy, said phenoxy, and said benzyloxy are unsubstituted or substituted by 1 to 5 independently selected R³² groups;
R¹⁴ is 1 to 4 substituents independently selected from the group consisting of H, alkyl, halo, —CN, haloalkyl,
R²⁷ and R²⁸ are independently selected from alkyl, cycloalkyl, cycloalkylalkyl, aryl, arylalkyl, hydroxyalkyl, and alkoxyalkyl;
or R²⁷ and R²⁸ together with the nitrogen to which they are attached, form an unsubstituted 3-7 membered heterocycloalkyl ring, or a 3-7 membered heterocycloalkyl ring substituted by 1-3 substituents independently selected from the group consisting of alkyl, and alkoxyalkyl;
wherein each R³² group is independently selected from the group consisting of halo, alkyl, cycloalkyl, cycloalkylalkyl, and —OR³⁵;
each R³⁵ is independently selected from the group consisting of H and alkyl.

2. A compound of claim 1 wherein R³ and R⁴ are hydrogen.
3. A compound of claim 1 wherein R¹ is

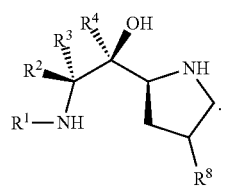

4. A compound of claim 1 having the stereochemical structure:

5. A compound of claim 1 selected from the group consisting of

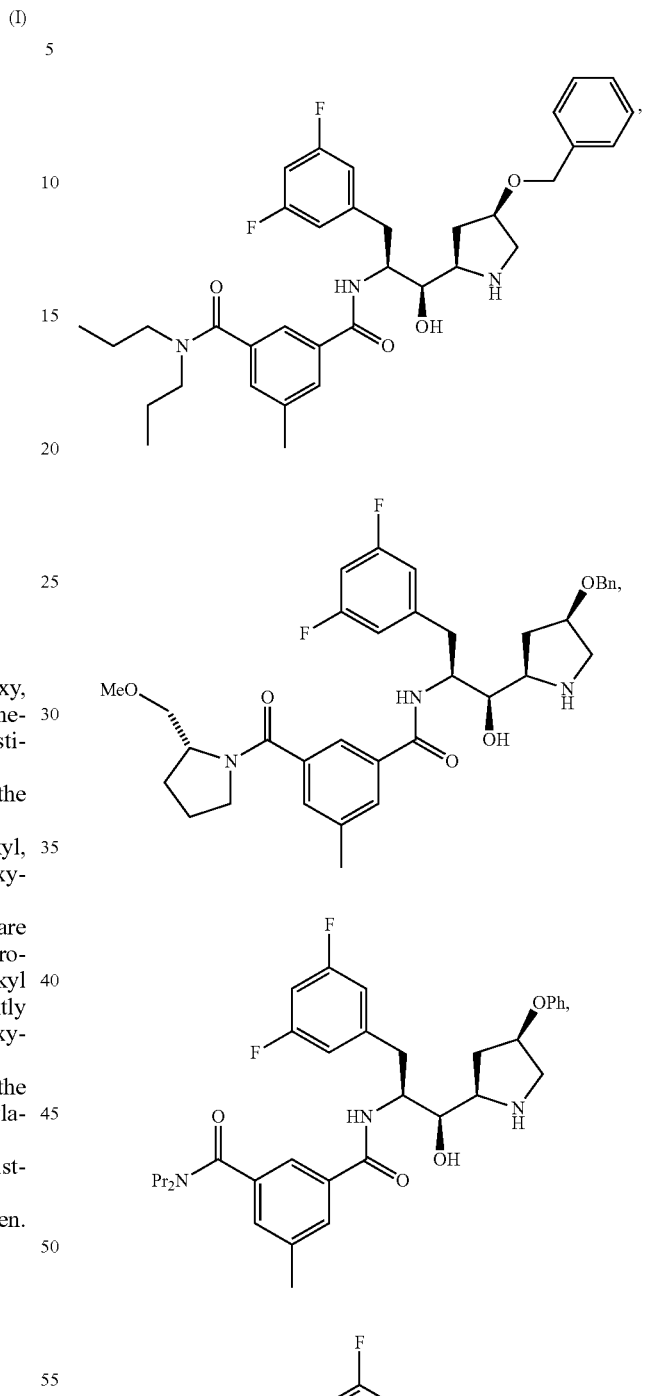

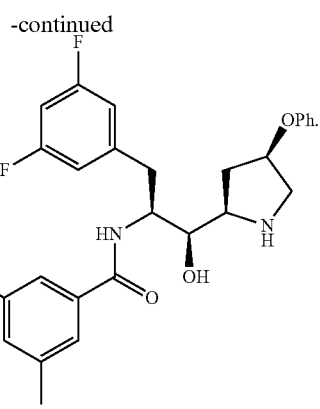

6. The compound of claim 1 which is

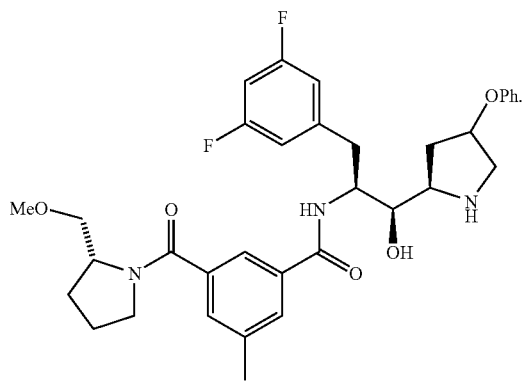

7. A pharmaceutical composition comprising an effective amount of a compound of claim 1 and a pharmaceutically effective carrier.

8. A pharmaceutical composition comprising an effective amount of a compound of claim 1, and an effective amount of a β-secretase inhibitor other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody in a pharmaceutically effective carrier.

9. A composition of claim 8 wherein the HMG-CoA reductase inhibitor is selected from the group consisting of atorvastatin, lovastatin, simvistatin, pravastatin, fluvastatin and rosuvastatin; the cholinesterase inhibitor is selected from the group consisting of atorvastatin, lovastatin, simvistatin, pravastatin, fluvastatin and rosuvastatin; the non-steroidal anti-inflammatory agent is selected from the group consisting of ibuprofen, naproxen, diclofenac, diflunisal, etodolac, flurbiprofen, indomethacin, ketoprofen, ketorolac, nabumetone, oxaprozin, piroxicam, sulindac, tolmetin, celecoxib and rofecoxib; and the N-methyl-D-aspartate receptor antagonist is memantine.

10. A kit comprising in separate containers in a single package pharmaceutical compositions for use in combination, in which one container comprises a compound of formula I in a pharmaceutically acceptable carrier and a second container comprises a β-secretase inhibitor other than those of formula I, an HMG-CoA reductase inhibitor, a gamma-secretase inhibitor, a non-steroidal anti-inflammatory agent, an N-methyl-D-aspartate receptor antagonist, a cholinesterase inhibitor or an anti-amyloid antibody in a pharmaceutically acceptable carrier.

* * * * *